United States Patent
Kreischer

(10) Patent No.: US 11,230,514 B1
(45) Date of Patent: Jan. 25, 2022

(54) METHODS FOR RECYCLING ETHYLENE IN AN ETHYLENE OLIGOMERIZATION REACTOR SYSTEM

(71) Applicant: Chevron Phillips Chemical Company LP, The Woodlands, TX (US)

(72) Inventor: Bruce E. Kreischer, Kingwood, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 17/329,287

(22) Filed: May 25, 2021

(51) Int. Cl.
C07C 7/04 (2006.01)
C07C 2/26 (2006.01)

(52) U.S. Cl.
CPC ............ *C07C 7/04* (2013.01); *C07C 2/26* (2013.01); *C07C 2531/14* (2013.01)

(58) Field of Classification Search
None
See application file for complete search history.

(56) References Cited

U.S. PATENT DOCUMENTS

| | | | |
|---|---|---|---|
| 7,476,776 B2 | 1/2009 | Han | |
| 9,017,522 B2 | 4/2015 | Gildenhuys | |
| 9,896,392 B2 | 2/2018 | Meiswinkel | |
| 2007/0185360 A1 | 8/2007 | Buchanan | |
| 2007/0185362 A1 | 8/2007 | Lattner | |
| 2015/0045603 A1* | 2/2015 | Han | B01J 31/143 585/511 |
| 2016/0207848 A1* | 7/2016 | Stochniol | C07C 2/10 |
| 2016/0207849 A1* | 7/2016 | Stochniol | C07C 2/10 |
| 2019/0010100 A1* | 1/2019 | Al-Dughaither | C10G 7/00 |
| 2019/0359745 A1* | 11/2019 | Chen | C07C 2/30 |
| 2020/0055798 A1* | 2/2020 | Miyamoto | C08F 6/12 |
| 2020/0262767 A1* | 8/2020 | Son | C07C 7/20 |
| 2020/0291140 A1* | 9/2020 | Nutt | B01J 31/143 |
| 2020/0308082 A1* | 10/2020 | Jung | B01J 31/22 |
| 2021/0122859 A1* | 4/2021 | Rapp | C08F 210/16 |

FOREIGN PATENT DOCUMENTS

| | | |
|---|---|---|
| WO | 2018208373 A1 | 11/2018 |
| WO | 2018208374 A1 | 11/2018 |
| WO | 2018208375 A1 | 11/2018 |
| WO | 2018208376 A1 | 11/2018 |
| WO | 2018208377 A1 | 11/2018 |

* cited by examiner

*Primary Examiner* — Ali Z Fadhel
(74) *Attorney, Agent, or Firm* — Merchant & Gould P.C.

(57) ABSTRACT

Methods for recycling ethylene from a reaction zone effluent stream from an oligomerization reaction zone, in which the reaction zone effluent stream contains an oligomer product effluent having at least 20 mass % octene(s), include a step of separating the reaction zone effluent stream into a first stream containing ethylene and less than 5 mass % $C_{4+}$ olefins, a second stream containing butene(s) and less than 10 mass % $C_{6+}$ olefins, a third stream containing at least 96 mass % hexene(s), and a fourth stream containing at least 96 mass % octene(s). The ethylene-rich first stream is recycled into the oligomerization reaction zone, while the recycle of 1-butene and other butenes is reduced significantly.

20 Claims, 2 Drawing Sheets

METHODS FOR RECYCLING ETHYLENE IN AN ETHYLENE OLIGOMERIZATION REACTOR SYSTEM

FIELD OF THE INVENTION

This disclosure relates generally to ethylene oligomerization processes and to downstream processes for recovering desirable hexene and octene products, and more particularly, relates to processes in which the amount of ethylene in the recycle stream of ethylene is increased while simultaneously decreasing the amount of butenes, such as 1-butene, in the ethylene recycle stream.

BACKGROUND OF THE INVENTION

Chromium-based catalyst systems often are used for the continuous oligomerization of ethylene in a reaction zone to produce hexenes and/or octenes. Generally, the recycle of unreacted ethylene to the reaction zone is desirably practiced. However, certain oligomerization reaction by-products, if recycled with the ethylene, can reduce the yield to and/or purity of desirable isolated 1-hexene and/or 1-octene products. Thus, it would be beneficial to increase the purity of the 1-hexene and/or 1-octene products and/or the production of 1-hexene and/or 1-octene in an ethylene oligomerization process in which ethylene is recycled, while reducing the recycle of certain undesirable reaction by-products. Accordingly, it is to this end that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Disclosed herein are methods for recycling ethylene from a reaction zone effluent stream from an oligomerization reaction zone, in which the reaction zone effluent stream contains an oligomer product effluent comprising at least 20 mass % octene(s). A first method can comprise a) separating the reaction zone effluent stream into a first stream comprising ethylene and less than or equal to 5 mass % $C_{4+}$ olefins, a second stream comprising butene(s) and hexene(s), and a third stream comprising at least 96 mass % octene(s); and b) recycling the first stream into the oligomerization reaction zone. A second method can comprise a) separating the reaction zone effluent stream into a first stream comprising ethylene and less than or equal to 5 mass % $C_{4+}$ olefins, a second stream comprising butene(s) and less than or equal to 10 mass % $C_{6+}$ olefins, a third stream comprising at least 96 mass % hexene(s), and a fourth stream comprising at least 96 mass % octene(s); and b) recycling the first stream into the oligomerization reaction zone.

Generally, in the first method, the second stream contains predominately butene(s) and hexene(s). Generally, in the second method, the third stream contains predominantly 1-hexene and the fourth stream contains predominantly 1-octene. In the first and second methods, the first stream—which is recycled to the oligomerization reaction zone—can be predominantly ethylene with less than or equal to 2 mass % butene(s). Overall, the amount of 1-butene in the oligomerization reaction zone often can be significantly less than 1 mass %, such as less than or equal to 0.5 mass % or less than or equal to 0.2 mass %.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The accompanying drawings, which are incorporated in and constitute a part of this disclosure, illustrate various aspects of the present invention. In the drawings.

DEFINITIONS

Figure 1:
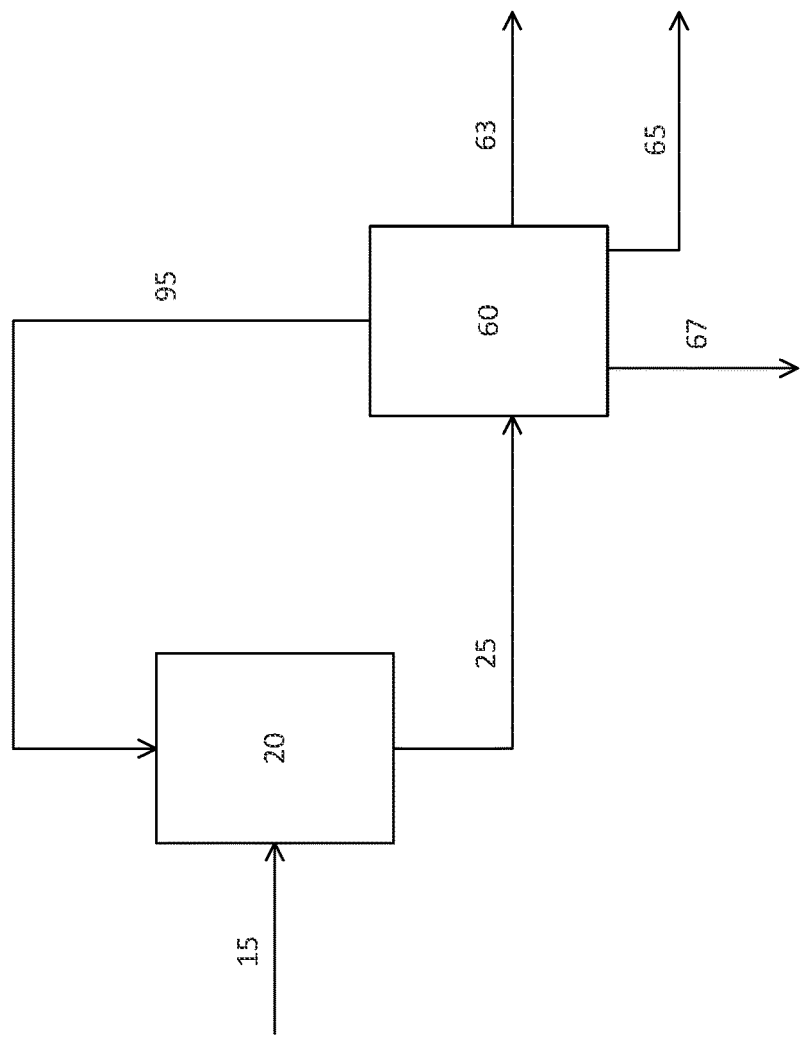
FIG. 1 illustrates an ethylene oligomerization reaction system consistent with an aspect of the present invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or statements, a combination of different features can be envisioned. For each and every aspect, and/or statement, and/or feature disclosed herein, all combinations that do not detrimentally affect the systems, compositions, processes, and/or methods described herein are contemplated with or without explicit description of the particular combination. Additionally, unless explicitly recited otherwise, any aspect, and/or statement, and/or feature disclosed herein can be combined to describe inventive processes and systems consistent with the present disclosure.

The terms "a," "an," and "the" are intended to include plural alternatives, e.g., at least one, unless otherwise specified. For instance, the disclosure of "a compressing stage" is meant to encompass one or more than one compressing stage, unless otherwise specified.

Generally, groups of elements are indicated using the numbering scheme indicated in the version of the periodic table of elements published in *Chemical and Engineering News,* 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; and a general reference to a butyl group includes an n-butyl group, a sec-butyl group, an iso-butyl group, and a t-butyl group.

Likewise, a general reference to hexene(s) includes all linear or branched, acyclic or cyclic, hydrocarbon compounds having six carbon atoms and 1 carbon-carbon double bond. Thus, hexene(s) encompasses, for instance, 1-hexene, 2-hexene, 3-hexene, neohexene, and cyclohexene. When a stream is indicated to contain a certain amount of hexene(s), this amount represents the total amount of hexene(s) present, whether only a single compound (e.g., 1-hexene) or a mixture of different compounds in any relative proportion. A similar interpretation applies for butene(s) and octene(s).

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. An "organyl group," "organylene group," or "organic group" can be aliphatic, (inclusive of being cyclic or acyclic, or linear or branched), or can be aromatic.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group can be an inert functional group because a single metal compound cannot complex with both the para ether group and the $N^2$-phosphinyl formamidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), and/or sulfidyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "reaction zone effluent," and it derivatives (e.g., oligomerization reaction zone effluent, trimerization reaction zone effluent, tetramerization reaction zone effluent, or trimerization and tetramerization reaction zone effluent) generally refers to all the material which exits the reaction zone through a reaction zone outlet/discharge which discharges a reaction mixture and can include reaction zone feed(s) (e.g., olefin, catalyst system or catalyst system components, and/or solvent), and/or reaction product (e.g., oligomer product including oligomers and non-oligomers, trimerization product including trimer and non-trimer, tetramerization product including tetramer and non-tetramer, or trimerization and tetramerization product including trimer and tetramer and non-trimer and tetramer). The term "reaction zone effluent" and its derivatives can be qualified to refer to certain portions by use of additional qualifying terms. For example, while reaction zone effluent refers to all material which exits the reaction zone through the reaction zone outlet/discharge, a reaction zone oligomer product effluent refers to only the oligomer product within the reaction zone effluent. Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" or "below" any recited maximum value for the feature disclosed herein.

Within this disclosure, the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4-position and hydrogens located at the 2, 3, 5, and 6 positions. References to compounds or groups having substitutions at positions in addition to the indicated position can be referenced using comprising or some other alternative language. For example, a reference to a phenyl group comprising a substituent at the 4-position refers to a group having a non-hydrogen substituent at the 4-position and hydrogen or any non-hydrogen substituent at the 2, 3, 5, and 6 positions.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the organoaluminum compound and the heteroatomic ligand transition metal compound complex after combining these components. Therefore, the terms "catalyst composition," "catalyst mixture," "catalyst system," and the like, encompass the initial starting components of the composition, as well as whatever product(s) may result from contacting these initial starting components. The terms "catalyst composition," "catalyst mixture," "catalyst system," and the like, may be used interchangeably throughout this disclosure.

The term oligomer refers to a product that contains from 2 to 20 monomer units. The terms "oligomer product" and "oligomer product effluent" include all oligomer products made by the "oligomerization" process, but exclude other non-oligomer components of the reaction zone effluent stream, such as unreacted monomer (ethylene), organic reaction medium, and hydrogen, amongst other components.

The term "oligomerization," and its derivatives, refers to processes which produce an oligomer product comprising at least 20 wt. %, 35 wt. %, 50 wt. %, or 60 wt. % products comprising from 2 to 20 monomer units. In an example, an "oligomerization" process using ethylene as the monomer produces a mixture of products comprising at least 20 wt. %, 35 wt. %, 50 wt. %, or 60 wt. % oligomers having from 4 to 40 carbon atoms.

The term "trimerization," and its derivatives, refers to a process which produces a mixture of products comprising at least 20 wt. %, 35 wt. %, 50 wt. %, or 60 wt. % products comprising three and only three monomer units. A "trimer" is a product which comprises three and only three monomer units. A "trimerization product" includes all products made by the trimerization process including trimer and products which are not trimer (e.g., dimers or tetramers, solid polymer). In an example, a "trimerization" process using ethylene as the monomer produces a mixture of products comprising at least 20 wt. %, 35 wt. %, 50 wt. %, or 60 wt. % hexenes.

The term "tetramerization," and its derivatives, refers to a process which produces a mixture of products comprising at least 20 wt. %, 35 wt. %, 50 wt. %, or 60 wt. % products comprising four and only four monomer units. A "tetramer" is a product which comprises four and only four monomer units. A "tetramerization product" includes all products made by the tetramerization process including tetramer and products which are not tetramer (e.g., dimers or trimers, solid polymer). In an example, a "tetramerization" process using ethylene as the monomer produces a mixture of products comprising at least 20 wt. %, 35 wt. %, 50 wt. %, or 60 wt. % octenes.

The term "trimerization and tetramerization," and its derivatives, refers to a process which produces a mixture of products comprising at least 20 wt. %, 35 wt. %, 50 wt. %, or 60 wt. % products comprising three and/or four and only three and/or four monomer units. A "trimerization and tetramerization product" includes all products made by the "trimerization and tetramerization" process including trimer, tetramer, and products which are not trimer and tetramer (e.g., dimers, solid polymer). In an example, a "trimerization and tetramerization" process using ethylene as the monomer produces a mixture of products comprising at least 20 wt. %, 35 wt. %, 50 wt. %, or 60 wt. % hexenes and octenes.

Within this specification, the word "reactor" refers to a single piece of equipment, such as, for example, a vessel, in which a reaction takes place, but excludes any associated equipment such as piping, pumps, and the like which is external to the vessel. Examples of reactors include stirred tank reactors (e.g., a continuous stirred tank reactor), plug flow reactors, or any other type of reactor. The terms "reactor" can be qualified to refer to more specific "reactors" by use of additional qualifying terms. For example, the use of the term "oligomerization reactor" indicates that the desired reaction within the reactor is an oligomerization.

Within this specification, term "reaction zone" refers to the portion of a reaction system where all the necessary reaction components and reaction conditions are present such that the reaction can occur at a desired rate. That is to say that the reaction zone begins where the necessary reaction components and reaction conditions are present to maintain the reaction within 25 percent of the average reaction rate and the reaction system ends where the conditions do not maintain a reaction rate within 25 percent of the average reaction rate (based upon a volume average of the reaction rate of the reaction zone). For example, in terms of an ethylene oligomerization process, the reaction zone begins at the point where sufficient ethylene and active catalyst system is present under the sufficient reaction conditions (e.g., temperature and/or pressure, among others) to maintain oligomer product production at the desired rate and the reaction zone ends at a point where either the catalyst system is deactivated, sufficient ethylene is not present to sustain oligomer product production, or other reaction conditions (e.g., temperature and/or pressure, among others) are not sufficient to maintain the oligomer product production or the desired oligomer product production rate. Within this specification the "reaction zone" can comprise one or more reactors. The term "reaction zone" can be qualified to refer to more specific "reaction zones" by use of additional qualifying terms. For example, the use of the term "oligomerization reaction zone" indicates that the desired reaction within the "reaction zone" is an oligomerization.

The term "reaction system" refers to all of the equipment to produce a product. The term "reaction system" includes reactors, reaction zones, and all the associated equipment, associated process lines, and control equipment which can bring the necessary component(s) into and out of the reaction system and control the reaction. Within this specification the "reaction system" can comprise one or more reactor zones, one or more reactors, and associated equipment to produce a product. The term "reaction system" can be qualified to refer to more specific "reaction systems" by use of additional qualifying terms. For example, the use of the term "oligomerization reaction system" indicates that the "reaction system" relates to an oligomerization.

Catalyst system productivity is defined herein in units of kilograms of a normal alpha olefin product produced per gram of transition metal (or chromium) of a heteroatomic ligand transition metal compound complex (or chromium compound) utilized in the catalyst system per hour-kg NAO/g transition metal/hr (or kg NAO/g Cr/hr).

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are methods for recycling ethylene from a reaction zone effluent stream from an oligomerization reaction zone, in which the effluent stream comprises an oligomer product effluent containing at least 20 mass %, and often at least 40 mass % octene(s). In these methods, a hexene product stream can be isolated in addition to the octene product stream, and an ethylene-rich stream is formed and subsequently recycled to the oligomerization reaction zone.

Beneficially, the disclosed methods increase the amount of ethylene in the ethylene recycle stream while simultaneously reducing the amount of butenes, such as 1-butene, recycled to the oligomerization reaction zone. The presence of 1-butene and other butenes in the oligomerization reaction zone can lead to significant amounts of by-product octenes—such as branched octenes—other than the desirable 1-octene product, thus greatly diminishing the purity of 1-octene in the octene product stream.

Recycling Ethylene in Oligomerizaton Reactor Systems

Aspects of this invention are directed to methods for recovering and recycling ethylene in oligomerization reactor systems. In some aspects, these methods for recovering and recycling ethylene in the oligomerization reaction system are performed to reduce the amount of $C_{4+}$ olefins and ethane in the recycle stream. A first representative method for recycling ethylene from a reaction zone effluent stream from an oligomerization reaction zone, in which the reaction zone effluent stream contains an oligomer product effluent comprising at least 20 mass % octene(s), can comprise a) separating the reaction zone effluent stream into a first stream comprising ethylene and less than or equal to 5 mass % $C_{4+}$ olefins, a second stream comprising butene(s) and hexene(s), and a third stream comprising any amount of octene(s) disclosed herein (e.g., at least 96 mass %); and b) recycling the first stream into the oligomerization reaction zone. Generally, the features of the first method for recovering ethylene (e.g., the amount of octene(s) in the oligomer product effluent, the amounts of ethylene and $C_{4+}$ olefins in the first stream, the amounts of butene(s) and hexene(s) in the second stream, the amount of octene(s) present in the third stream, and the techniques for separating the effluent stream into the respective streams, among others) are independently described herein and these features can be combined without limitation, and in any combination to further describe the disclosed methods for recycling ethylene. The second representative method for recycling ethylene from a reaction zone effluent stream from an oligomerization reaction zone, in which the reaction zone effluent stream contains an oligomer product effluent comprising at least 20 mass % octene(s), can comprise a) separating the reaction zone effluent stream into a first stream comprising ethylene and less than or equal to 5 mass % $C_{4+}$ olefins, a second stream comprising butene(s) and less than or equal to 10 mass % $C_{6+}$ olefins, a third stream comprising any amount of hexene(s) disclosed herein (e.g., at least 96 mass %), and a fourth stream comprising any amount of octene(s) disclosed herein (e.g., at least 96 mass %); and b) recycling the first stream into the oligomerization reaction zone. Generally, the features of the second method for recovering ethylene (e.g., the amount of octene(s) in the oligomer product effluent, the amounts of ethylene and $C_{4+}$ olefins in the first stream, the amounts of butene(s) and $C_{6+}$ olefins in the second stream, the amount of hexene(s) in the third stream, the amount of octene(s) in the fourth stream, and the techniques for separating the effluent stream into the respective streams, among others) are independently described herein and these features can be combined without limitation, and in any combination to further describe the disclosed methods for recycling ethylene. Moreover, additional process steps can be performed before, during, and/or after the steps of these methods, and can be utilized without limitation and in any combination to further describe the methods for recovering ethylene, unless stated otherwise. Further, and beneficially, the methods for recovering ethylene can be performed continuously.

In the disclosed methods, the amount of octene(s) in the oligomer product effluent typically can fall within a range from 20 to 99 mass %, based on the total amount of oligomers in the oligomer product effluent. In an aspect, the minimum amount of octene(s) in the oligomer product effluent can be 20, 30, or 40 mass %. In another aspect, the maximum amount of octene(s) in the oligomer product effluent can be 99, 95, 92.5, 90, 87.5, or 85 mass %. Generally, the amount of octene(s) in the oligomer product effluent can range from any minimum amount of octene(s) in the oligomer product effluent to any maximum amount of octene(s) in the oligomer product effluent described herein. For instance, the amount of octene(s)—based on the total mass of oligomers in the oligomer product effluent—can be from 20 to 99 mass %, from 30 to 95 mass %, from 40 to 95 mass %, from 40 to 90 mass %, from 20 to 90 mass %, from 30 to 87.5 mass %, from 30 to 85 mass %, from 40 to 87.5 mass %, from 40 to 85 mass %, from 20 to 60 mass %, from 30 to 55 mass %, or from 40 to 55 mass % octene(s). Other appropriate amounts of octene(s) in the oligomer product effluent are readily apparent from this disclosure.

In addition to octene(s), the oligomer product effluent can further comprise any suitable amount of hexene(s). In an aspect, the minimum amount of hexene(s) in the oligomer product effluent can be 5, 10, 15, 20, 25, 30, or 35 mass %. In another aspect, the maximum amount of hexene(s) in the oligomer product effluent can be 75, 65, 60, 55, or 50 mass %. Generally, the amount of hexene(s) in the oligomer product effluent can range from any minimum amount of hexene(s) in the oligomer product effluent to any maximum amount of hexene(s) in the oligomer product effluent described herein. For instance, the amount of hexene(s)—based on the total mass of oligomers in the oligomer product effluent—can be from 5 to 75 mass %, from 10 to 75 mass %, from 15 to 75 mass %, from 20 to 60 mass %, from 25 to 55 mass %, from 30 to 50 mass %, from 35 to 65 mass %, or from 35 to 50 mass % hexene(s). Other appropriate amounts of hexene(s) in the oligomer product effluent are readily apparent from this disclosure.

In addition to the oligomer product effluent (that contains octene(s) and/or hexene(s)), the reaction zone effluent stream also can contain the catalyst system, unreacted ethylene, other oligomer product olefins (e.g., butene(s) and/or $C_{10+}$ olefins), hydrogen, and organic reaction medium. In some aspects, the catalyst system can be deactivated in any typical manner, such as by contacting the reaction zone effluent stream with a suitable catalyst system deactivating agent. When the catalyst system is deactivated, the catalyst system can be deactivated at any point in the reaction zone effluent stream processing and/or product recovery processing that is advantageous for deactivating the catalyst system. As used herein, reaction zone effluent stream (or reaction zone effluent) refers to a general reaction effluent stream regardless of whether or not the reaction zone effluent or its subsequent streams have been processed to deactivate the catalyst system.

In step a) of the first method for recovering ethylene, the reaction zone effluent stream—which contains an oligomer product effluent comprising at least 20 mass % octene(s)—can be separated into a first stream, a second stream, and a third stream. In step a) of the second method for recovering ethylene, the reaction zone effluent stream—which contains an oligomer product effluent comprising at least 20 mass % octene(s)—can be separated into a first stream, a second stream, a third stream, and a fourth stream. Referring now to the first stream of the first and second methods, the first stream can comprise ethylene and less than or equal to 5 mass % $C_{4+}$ olefins. Since the first stream is recycled into the oligomerization reaction zone in step b), the vast majority of the first stream is ethylene, with the amount of ethylene generally exceeding 85 mass % of the first stream. In some aspects, the first stream can comprise at least 85, at least 86, at least 87, at least 88, at least 89, or at least 90 mass % ethylene, and often up to a maximum of 99, 97, 95, or 92.5 mass % ethylene. The amount of ethylene in the first stream can range from any minimum ethylene content to any maximum ethylene content described herein. Illustrative and non-limiting ranges for the amount of ethylene in the first stream can include from 85 to 99 mass %, from 85 to 95 mass %, from 87 to 97 mass %, from 88 to 92.5 mass %, from 90 to 99 mass %, from 90 to 97 mass %, or from 90 to 95 mass % ethylene. Other appropriate amounts of ethylene in the first stream are readily apparent from this disclosure.

The first stream of the first and second methods can also contain a maximum of 5 mass % $C_{4+}$ olefins, which is inclusive of $C_4$ olefins, $C_6$ olefins, $C_8$ olefins, and so forth. The amounts of any $C_{4+}$ olefins are reduced in the disclosed methods for recycling ethylene, and therefore, the total amount of $C_{4+}$ olefins in the first stream often can be less than or equal to 4 mass %; alternatively, less than or equal to 3 mass %; alternatively, less than or equal to 2 mass %; or alternatively, less than or equal to 1 mass % $C_{4+}$ olefins.

In addition to reducing the amount of $C_{4+}$ olefins in the first stream of the first and second methods, which is recycled to the oligomerization reaction zone, the amounts of butene(s) in particular also are reduced. The presence of butene(s) (e.g., 1-butene) in the reaction zone can lead to undesirable reactions that produce $C_8$'s other than 1-octene. Accordingly, consistent with this invention, the amount of butene(s) in the first stream can be less than or equal to 2 mass % or less than or equal to 1.5 mass % in one aspect, while the amount of butene(s) in the first stream can be less than or equal to 1 mass % or less than or equal to 0.75 mass % in another aspect, and in yet another aspect, the amount of butene(s) in the first stream can be less than or equal to 0.5 mass %, less than or equal to 0.35 mass %, or less than or equal to 0.2 mass %.

Stated another way, increasing ethylene and reducing 1-butene and other butenes in the first stream can be characterized by a mass ratio of ethylene:butene(s) of at least 100:1, 150:1, 200:1, 300:1, or 350:1, and often up to a maximum mass ratio of 5000:1, 1500:1, 1000:1, or 500:1. Illustrative and non-limiting ranges for the mass ratio of ethylene:butene(s) in the first stream (and recycled to the oligomerization reaction zone) can include from 100:1 to 5000:1, from 100:1 to 500:1 from 150:1 to 1500:1, from 200:1 to 500:1, from 300:1 to 1500:1, from 350:1 to 5000:1, from 350:1 to 1000:1, or from 350:1 to 500:1. Other appropriate mass ratios of ethylene:butene(s) in the first stream are readily apparent from this disclosure.

Additionally or alternatively, reducing butene(s) while increasing ethylene recycled to the oligomerization reaction zone can result in very low levels of butene(s) in the reaction zone. In an aspect, the minimum amount of butene(s) in the reaction zone can be 0.01, 0.02, 0.035, 0.05, or 0.1 mass %. In another aspect, the maximum amount of butene(s) in the reaction zone can be 1, 0.75, 0.5, 0.35, 0.25, or 0.2 mass %. Generally, the amount of butene(s) in the reaction zone can range from any minimum amount of butene(s) to any maximum amount of butene(s) described herein. For instance, the amount of butene(s) in the reaction zone can be from 0.01 to 0.75 mass %, from 0.02 to 0.5 mass %, from 0.05 to 0.35 mass %, or from 0.1 to 0.2 mass % butene(s). Other appropriate amounts of butene(s) in the oligomerization reaction zone are readily apparent from this disclosure.

Certain light compounds can be separated from the reaction zone effluent stream and ultimately become part of the first stream. Non-limiting examples of these light compounds can include hydrogen ($H_2$) and methane. While not limited thereto, the first stream can contain less than or equal to 5, 4, 3, 2, or 1 mass % of hydrogen; additionally or alternatively, less than or equal to 5, 4, 3, 2, or 1 mass % of methane. In some aspects, the first stream can contain (in total) less than or equal to 5, 4, 3, 2, or 1 mass % of hydrogen and methane.

Referring now the second stream of the first method that is separated from the reaction zone effluent stream, the second stream of the first method can comprise butene(s) and hexene(s) and less than or equal to 10 mass % $C_{8+}$ olefins (inclusive of $C_8$ olefins, $C_{10}$ olefins, and so forth). In aspects of this invention, the second stream of the first method can be a non-product stream, for instance, the second stream of the first method can be a heavy purge stream in which effluent butene(s) and hexene(s) are accumulated (in particular, butene(s)), such that they are not recycled along with ethylene into the oligomerization reaction zone. This is exemplified by the second stream of the first method containing, on a mass basis, more butene(s) than that present in the first stream of the first method. In some aspects, on a mass basis, the second stream of the first method can contain at least twice (2×) as much butene(s) as that in the first stream of the first method, or at least three times (3×) as much butene(s) as that in the first stream of the first method, and often the second stream of the first method can contain up to 5× or 10× the amount of butene(s) as that present in the first stream of the first method.

Since certain $C_{8+}$ olefin products such as 1-octene are desirable, the amounts of any $C_{8+}$ olefins are reduced in the second stream of the first method. A maximum of 10 mass % $C_{8+}$ olefins in the second stream of the first method is standard. In an aspect, the amounts of any $C_{8+}$ olefins in the second stream of the first method can be less than or equal to 8, 6, 5, 4, 3, or 2 mass %.

In the second stream of the first method, the amount of butene(s) and hexene(s) typically can fall within a range from 1 to 50 mass %, although not limited thereto. In an aspect, the minimum amount of butene(s) and hexene(s) in the second stream of the first method can be 1, 2, 3, 4, or 5 mass %. In another aspect, the maximum amount of butene(s) and hexene(s) in the second stream of the first method can be 50, 40, 35, 30 25, 20, 18, 15, or 12 mass %. Generally, the amount of butene(s) and hexene(s) in the second stream of the first method (based on the total mass of the second stream) can range from any minimum amount of butene(s) and hexene(s) to any maximum amount of butene(s) and hexene(s) described herein. For instance, the amount of butene(s) and hexene(s) in the second stream of the first method can be from 1 to 50 mass %, from 1 to 40 mass %, from 2 to 35 mass %, from 2 to 30 mass %, or from 3 to 25 mass % butene(s) and hexene(s). Other appropriate amounts of butene(s) (e.g., 1-butene) in the second stream of the first method are readily apparent from this disclosure. The second stream of the first method, in addition to butene(s) and hexene(s), can further comprises ethylene and ethane, and/or $C_{8+}$ olefin. In the second stream of the first method, the amount of ethylene and ethane can range from 40 to 90 mass %, from 50 to 87.5 mass %, or from 60 to 85 mass %. In the second stream of the first method, the amount of $C_{8+}$ olefins can be less than or equal to 10, 8, 7, 6, 5, 4, or 3 mass %.

Referring now the second stream of the second method that is separated from the reaction zone effluent stream, the second stream of the second method can comprise butene(s) and less than or equal to 10 mass % $C_{6+}$ olefins (inclusive of $C_6$ olefins, $C_8$ olefins, $C_{10}$ olefins, and so forth). In aspects of this invention, the second stream of the second method can be a non-product stream, for instance, the second stream of the second method can be a heavy gas purge stream in which effluent 1-butene and other butenes are accumulated, such that they are not recycled along with ethylene into the oligomerization reaction zone. This is exemplified by the second stream of the second method containing, on a mass basis, more butene(s) than that present in the first stream of the second method. In some aspects, on a mass basis, the second stream of the second method can contain at least twice (2×) as much butene(s) as that in the first stream of the second method, or at least three times (3×) as much butene(s) as that in the first stream of the second method, and often the second stream of the second method can contain up to 5× or 10× the amount of butene(s) as that present in the first stream of the second method.

Since certain $C_{6+}$ olefin products such as 1-hexene and 1-octene are desirable in the second method, the amounts of any $C_{6+}$ olefins are reduced in the second stream of the second method. A maximum of 10 mass % $C_{6+}$ olefins in the second stream of the second method is standard, but more often, the amounts of any $C_{6+}$ olefins in the second stream of the second method can be less than or equal to 8 mass % in one aspect, less than or equal to 7 mass % in another aspect, less than or equal to 6 mass % in yet another aspect, or less than or equal to 5 mass % $C_{6+}$ olefins in still another aspect.

In the second stream of the second method, the amount of butene(s) typically can fall within a range from 1 to 25 mass %, although not limited thereto. In an aspect, the minimum amount of butene(s) in the second stream of the second method can be 1, 2, 3, 4, or 5 mass %. In another aspect, the maximum amount of butene(s) in the second stream of the second method can be 25, 20, 18, 15, or 12 mass %. Generally, the amount of butene(s) in the second stream (based on the total mass of the second stream of the second method) can range from any minimum amount of butene(s) to any maximum amount of butene(s) described herein. For instance, the amount of butene(s) in the second stream of the second method can be from 1 to 25 mass %, from 1 to 12 mass %, from 2 to 20 mass %, from 2 to 18 mass %, from 3 to 25 mass %, from 4 to 15 mass %, or from 5 to 12 mass % butene(s). Other appropriate amounts of butene(s) in the second stream of the second method are readily apparent from this disclosure. The second stream of the second method, in addition to butene(s) and $C_{6+}$ olefins, can further comprise ethylene and/or ethane. In the second stream of the second method, the total amount of ethylene and ethane can range from 60 to 90 mass %, from 70 to 87.5 mass %, or from 70 to 85 mass %. In the second stream of the second method, the amount of $C_{6+}$ olefins can be less than or equal to 8, 7, 6, 5, 4, or 3 mass %.

The amount of 1-butene in the second stream of the first and second methods is typically very similar to the amount of butene(s) in the second stream of the respective first and second methods. In one aspect, for instance, the second stream of the first and second methods can contain at least 80 mass % or at least 85 mass % 1-butene, while in another aspect, the second stream of the first and second methods can contain at least 90 mass % or at least 95 mass % 1-butene, and in yet another aspect, the second stream of the first and second methods can contain at least 98 mass % or at least 99 mass % 1-butene, based on the total mass of the butene(s) in the second stream of the first and second methods. These representative levels of 1-butene in butene(s) in the second stream of the first and second methods also are applicable to any other streams described herein that contains butene(s) and can be used without limitation to describe the amount of 1-butene in the butene(s) of these other streams containing butene(s).

Referring now to the third stream of the second method that is separated from the reaction zone effluent stream, the third stream of the second method can comprise at least 96 mass % hexene(s). Certain hexenes, such as 1-hexene, are desirable oligomer products, so the amount of hexene(s) in the third stream is generally maximized. Thus, in further aspects, the third stream of the second method can comprise at least 97 mass % hexene(s); alternatively, at least 98 mass % hexene(s); or alternatively, at least 99 mass % hexene(s). In further aspects, the third stream of the second method that is separated from the reaction zone effluent stream can comprise less than 4, 3, 2, 1, 0.75, or 0.5 mass % $C_{4-}$ olefins (inclusive of $C_4$ olefins, $C_2$ olefins, and so forth). In yet further aspects, the third stream of the second method that is separated from the reaction zone effluent stream can comprise less than 2, 1, 0.75, or 0.5 mass % $C_{8+}$ olefins (inclusive of $C_8$ olefins, $C_{10}$ olefins, and so forth).

The purity of 1-hexene in the third stream of the second method can be at least 90 mass % of 1-hexene, based on the total mass of the hexene(s) in the third stream. In one aspect, for instance, the third stream of the second method can contain at least 92.5 mass % or at least 95 mass % 1-hexene, while in another aspect, the third stream of the second method can contain at least 97.5 mass % or at least 98 mass % 1-hexene, and in yet another aspect, the third stream of the second method can contain at least 98.5 mass % or at least 99 mass % 1-hexene, based on the total mass of the hexene(s) in the third stream of the second method. In further aspects, the third stream of the first method or the fourth stream of the second method that is separated from the reaction zone effluent stream can comprise less than 4, 3, 2, 1, 0.75, or 0.5 mass % $C_{6-}$ olefins (inclusive of $C_6$ olefins, $C_4$ olefins, $C_2$ olefins, and so forth). In yet further aspects, the third stream of the first method or the fourth stream of the second method that is separated from the reaction zone effluent stream can comprise less than 2, 1, 0.75, or 0.5 mass % $C_{10+}$ olefins (inclusive of $C_{10}$ olefins, $C_{12}$ olefins, and so forth).

Referring now the third stream of the first method and the fourth stream of the second method that is separated from the reaction zone effluent stream, the third stream of the first method and the fourth stream of the second method can comprise at least 96 mass % octene(s). Certain octenes, such as 1-octene, are desirable oligomer products. Thus, in further aspects, the third stream of the first method and the fourth stream of the second method can comprise at least 97 mass % octene(s); alternatively, at least 98 mass % octene(s); or alternatively, at least 99 mass % octene(s).

The purity of 1-octene in the third stream of the first method and the fourth stream of the second method also can be maximized, such that the third stream of the first method and the fourth stream of the second method can contain at least 95 mass % of 1-octene, based on the total mass of the octene(s). In one aspect, for instance, the third stream of the first method and the fourth stream of the second method can contain at least 96.5 mass % or at least 97 mass % 1-octene, while in another aspect, the third stream of the first method and the fourth stream of the second method can contain at least 97.5 mass % or at least 98 mass % 1-octene, and in yet another aspect, can contain at least 98.5 mass % or at least 99 mass % 1-octene, based on the total mass of the octene(s).

The overall ethylene recycle rate in the disclosed methods is generally very high. The amount of ethylene recycled—in mass %—is determined by dividing the amount of ethylene in the first stream (which is recycled to the oligomerization reaction zone) by the amount of ethylene in the reaction zone effluent stream. In an aspect, the minimum amount of ethylene recycled can be at least 86, 88, 89, 90, or 91 mass %. In another aspect, the maximum amount of ethylene recycled can be 99, 97, 96, 95, or 94 mass %. Generally, the amount of ethylene recycled can range from any minimum amount of recycled ethylene to any maximum amount of recycled ethylene described herein. For instance, the amount of recycled ethylene can be from 86 to 99 mass %, from 88 to 97 mass %, from 89 to 96 mass %, from 90 to 95 mass %, or from 91 to 94 mass %. Other appropriate ethylene recycle rates are readily apparent from this disclosure.

High levels of ethylene recycle are very important because ethylene conversion often does not exceed 90% in the oligomerization reaction zone. Determined based on the total amount of ethylene entering the reaction zone (fresh and recycle) and the amount of unreacted ethylene in the reaction zone effluent stream, the minimum ethylene conversion can be at least 20, 30, 35, 40, 45, or 50 mass %, while the maximum ethylene conversion can be 99, 95, 90, 80, 75, 70, or 65 mass %. Generally, the ethylene conversion in the reaction zone can range from any minimum conversion to any maximum conversion described herein. For instance, the ethylene conversion can be from 20 to 100 mass %, from 35 to 99 mass %, from 30 to 90 mass %, from 40 to 80 mass %, from 50 to 70 mass %, or from 55 to 65 mass %. Other appropriate ethylene conversions are readily apparent from this disclosure.

The disclosed methods for recycling ethylene include a step of separation the reaction zone effluent stream into the first stream, the second stream, and the third stream for the first method, or the first stream, the second stream, the third stream, and the fourth stream for the second method. While not limited thereto, the step of separating the reaction zone effluent stream into the first stream of the first and second methods can include at least two separating stages, or at least two compressing stages, or both at least two separating stages and at least two compressing stages. Any suitable separations techniques can be used, such as flashing, heating, evaporating, cooling/quenching, distilling, and the like, as well as combinations of more than one separation technique. Compressing stages can performed with a compressor, although not limited thereto. It should be noted, that while the disclosed methods can include at least two separating stages, or at least two compressing stages, or at least two separating stages and at least two compressing stages, for separating the reaction zone effluent stream into the first stream, depending upon the actual design not all of the ethylene, butene(s), or other components of the first stream of the first and second methods may pass through the at least two separating stages, or the at least two compressing stages, or the at least two separating stages and the at least two compressing stages.

In an aspect, separating the reaction zone effluent stream into the first stream of the first and second methods can comprise (a) separating the reaction zone effluent stream into a first vapor stream and a first liquid stream, (b) separating the first liquid stream into a second vapor stream and a second liquid stream, (c) separating the second vapor stream into a light fraction and a first oligomer fraction, and (d) combining the first vapor stream with the light fraction and forming the first stream and a light gas purge stream. The light gas purge stream can contain lights such as hydrogen ($H_2$) and/or methane, and in this aspect, the light gas purge stream can contain (on a mass % basis) more hydrogen than that in the first stream and/or more methane than that in the first stream.

While not limited thereto, the light gas purge stream can contain less than or equal to 5, 4, 3, 2, or 1 mass % of hydrogen; additionally or alternatively, less than or equal to 5, 4, 3, 2, or 1 mass % of methane. In some aspects, the light gas purge stream can contain (in total) less than or equal to 5, 4, 3, 2, or 1 mass % of hydrogen and methane. Generally, the total amount of the light gas purge stream is significantly less than that of the second stream (the heavy gas purge stream, which contains a large amount of butene(s)). Also while not being limited thereto, the mass ratio of the light gas purge stream to the second stream (the heavy gas purge stream) can be from 1:5 to 1:20; alternatively, from 1:6 to 1:15; or alternatively, from 1:7 to 1:12. In a further aspect, the light gas purge stream can contain at least 80, 85, 90, 92, 94, or 96 mass % ethylene.

In a further aspect of the first method, the second liquid stream can be separated into an overhead stream, the second stream, and the third stream. Any suitable number of separating stages can be used to form the overhead stream, the second stream, and the third stream of the first method and any suitable separations techniques can be used, such as flashing, evaporating, cooling/quenching, distilling, and the like, as well as combinations of more than one separation technique. In a further aspect of the second method, the second liquid stream can be separated into an overhead stream, the second stream, the third stream, and the fourth stream. Any suitable number of separating stages can be used to form the overhead stream, the second stream, the third stream, and the fourth stream, and any suitable separations techniques can be used, such as flashing, evaporating, cooling/quenching, distilling, and the like, as well as combinations of more than one separation technique.

Consistent with aspects of this invention, the methods for recycling ethylene that are described herein can further comprise the steps of introducing (1) ethylene, (2) a catalyst system or catalyst system components, (3) optionally, an organic reaction medium, and (4) optionally, hydrogen, into the oligomerization reaction zone; forming the oligomer product effluent; and discharging the oligomerization reaction zone effluent stream from the oligomerization reaction zone. Ethylene, the catalyst system or catalyst system components, the organic reaction medium, and hydrogen are independently described herein and these independent descriptions can be utilized without limitation, and in any combination, to further describe the methods for recycling ethylene described herein.

Ethylene, the catalyst system or catalyst system components, the organic reaction medium, and hydrogen can be combined in any order or sequence and introduced into the oligomerization reaction zone separately or in any combination. For instance, hydrogen and ethylene can be combined and fed to the reaction zone separately from the catalyst system or catalyst system components. This invention is not limited by the manner in which the respective feed streams are introduced into the reaction zone.

When employed, any suitable organic reaction medium can be used in the disclosed methods, such as a hydrocarbon. Illustrative hydrocarbons can include, for example, aliphatic hydrocarbons, aromatic hydrocarbons, petroleum distillates, or combinations thereof; alternatively, aliphatic hydrocarbons; or alternatively, aromatic hydrocarbons. Aliphatic hydrocarbons which can be used as the first organic reaction medium include $C_3$ to $C_{20}$ aliphatic hydrocarbons; alternatively, $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified. In some aspects, the aliphatic hydrocarbon which can be utilized as the first organic reaction medium can be a hydrocarbon olefin (linear or branched, or terminal or internal). Non-limiting examples of suitable acyclic aliphatic hydrocarbon reaction medium that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or a mixture of linear and branched $C_6$ acyclic aliphatic hydrocarbons); alternatively, heptane (n-heptane or a mixture of linear and branched $C_7$ acyclic aliphatic hydrocarbons); or alternatively, octane (n-octane or a mixture of linear and branched $C_8$ acyclic aliphatic hydrocarbons). In other aspects, the acyclic aliphatic reaction medium can be a product of the oligomerization (e.g., 1-hexene and/or 1-octene). Non-limiting examples of suitable cyclic aliphatic hydrocarbon reaction medium include cyclohexane and methyl cyclohexane; alternatively, cyclohexane; or alternatively, methylcyclohexane. Aromatic hydrocarbons which can be useful as an organic reaction medium include $C_6$ to $C_{20}$ aromatic hydrocarbons, or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene. In a particular aspect of this invention, the organic reaction medium can comprise, or consist essentially of, or consist of, cyclohexane.

The catalyst system or catalyst system components can comprise (i) a heteroatomic ligand transition metal compound complex (or a heteroatomic ligand chromium compound complex) and an organoaluminum compound, or (ii) a heteroatomic ligand, a transition metal compound (or a chromium compound), and an organoaluminum compound. The catalyst system and catalyst system components are disclosed in greater detail herein.

Forming the oligomer product effluent in the oligomerization reaction zone can be performed at any suitable oligomerization temperatures and pressure. Often, the oligomer product can be formed at a minimum temperature of 0° C., 20° C., 30° C., 40° C., 45° C., or 50° C.; additionally or alternatively, at a maximum temperature of 165° C., 160° C., 150° C., 140° C., 130° C., 115° C., 100° C., or 90° C.

Generally, the oligomerization temperature at which the oligomer product is formed can be in a range from any minimum temperature disclosed herein to any maximum temperature disclosed herein. Accordingly, suitable non-limiting ranges can include the following: from 0° C. to 165° C., from 20° C. to 160° C., from 20° C. to 115° C., from 40° C. to 160° C., from 40° C. to 140° C., from 50° C. to 150° C., from 50° C. to 140° C., from 50° C. to 130° C., from 50° C. to 100° C., from 60° C. to 115° C., from 70° C. to 100° C., or from 75° C. to 95° C. Other appropriate oligomerization temperatures and temperature ranges are readily apparent from this disclosure.

The oligomer product can be formed at a minimum pressure (or ethylene partial pressure) of 50 psig (344 kPa), 100 psig (689 kPa), 200 psig (1.4 MPa), or 250 psig (1.5 MPa); additionally or alternatively, at a maximum pressure (or ethylene partial pressure) of 4,000 psig (27.6 MPa), 3,000 psig (20.9 MPa), 2,000 psig (13.8 MPa), or 1,500 psig (10.3 MPa). Generally, the oligomerization pressure (or ethylene partial pressure) at which the oligomer product is formed can be in a range from any minimum pressure disclosed herein to any maximum pressure disclosed herein. Accordingly, suitable non-limiting ranges can include the following: from 50 psig (344 kPa) to 4,000 psig (27.6 MPa), from 100 psig (689 kPa) to 3,000 psig (20.9 MPa), from 100 psig (689 kPa) to 2,000 psig (13.8 MPa), from 200 psig (1.4 MPa) to 2,000 psig (13.8 MPa), from 200 psig (1.4 MPa) to 1,500 psig (10.3 MPa), or from 250 psig (1.5 MPa) to 1,500 psig (10.3 MPa). Other appropriate oligomerization pressures (or ethylene partial pressures) are readily apparent from this disclosure.

When used, hydrogen can be fed directly to the reaction zone, or hydrogen can be combined with an ethylene feed prior to the reaction zone. In the reaction zone, the hydrogen partial pressure can be at least 1 psig (6.9 kPa), 5 psig (34 kPa), 10 psig (69 kPa), 25 psig (172 kPa), or 50 psig (345 kPa); additionally or alternatively, a maximum hydrogen partial pressure of 2000 psig (13.8 MPa), 1750 psig (12.1 MPa), 1500 psig (10.3 MPa), 1250 psig (8.6 MPa), 1000 psig (6.9 MPa), 750 psig (5.2 MPa), 500 psig (3.4 MPa), or 400 psig (2.8 MPa). Generally, the hydrogen partial pressure can range from any minimum hydrogen partial pressure disclosed herein to any maximum hydrogen partial pressure disclosed herein. Therefore, suitable non-limiting ranges for the hydrogen partial pressure can include the following ranges: from 1 psig (6.9 kPa) to 2000 psig (13.8 MPa), from 1 psig (6.9 kPa) to 1750 psig (12.1 MPa), from 5 psig (34 kPa) to 1500 psig (10.3 MPa), from 5 psig (34 kPa) to 1250 psig (8.6 MPa), from 10 psig (69 kPa) to 1000 psig (6.9 MPa), from 10 psig (69 kPa) to 750 psig (5.2 MPa), from 10 psig (69 kPa) to 500 psig (3.5 MPa), from 25 psig (172 kPa) to 750 psig (5.2 MPa), from 25 psig (172 kPa) to 500 psig (3.4 MPa), from 25 psig (172 kPa) to 400 psig (2.8 MPa), or from 50 psig (345 kPa) to 500 psig (3.4 MPa). Other appropriate hydrogen partial pressures in the reaction zone for the formation of the oligomer product are readily apparent from this disclosure.

The oligomerization reaction zone in which the oligomer product is formed can comprise any suitable reactor. Non-limiting examples of reactor types can include a stirred tank reactor, a plug flow reactor, or any combination thereof; alternatively, a fixed bed reactor, a continuous stirred tank reactor, a loop slurry reactor, a solution reactor, a tubular reactor, a recycle reactor, or any combination thereof. In an aspect, the reaction zone can have more than one reactor in series or in parallel, and including any combination of reactor types and arrangements. Moreover, the oligomerization process used to form the oligomer product can be a continuous process or a batch process, or any reactor or vessel within the oligomerization reaction system can be operated continuously or batchwise.

FIG. 1 illustrates an ethylene oligomerization reaction system 10 consistent with an aspect of the present invention. The system 10 can include an oligomerization reaction zone 20 and a separations system 60. Feed streams 15 (representing one or more feed streams) to the oligomerization reaction zone can include, for instance, a catalyst system feed stream, an organic reaction medium feed stream, an ethylene feed stream, and a hydrogen feed stream (if hydrogen is used), and these feed streams can be fed directly into the oligomerization reaction zone 20, or any of these feed streams can be combined prior to the oligomerization reaction zone 20 and the resulting mixture fed to the oligomerization reaction zone 20. It is understood that there are many different options in which the feed components can be introduced into oligomerization reaction zone 20, and this invention is not limited by the specific configuration of the feed streams 15 entering the oligomerization reaction zone. Additionally, it should be noted that while FIG. 1 illustrates feed stream 15 being introduced directly to the oligomerization reaction zone 20, it is further contemplated that some of the oligomerization reaction zone 20 feeds can be introduced into the ethylene recycle stream, i.e., first stream 95, prior to entry to the oligomerization reaction zone 20. For example, all or a portion of ethylene, all or a portion of the organic reaction medium, or a combination thereof, can be introduced into the ethylene recycle stream before it enters the oligomerization reaction zone. U.S. patent publication 2017/0342000 describes potential methods for introducing feed streams into an oligomerization reaction zone, among other methods, which can be utilized to introduce the feed streams 15 to the oligomerization reaction zone 20.

Ethylene oligomerization occurs in the oligomerization reaction zone 20, and exiting the reaction zone is a reaction zone effluent stream 25, which enters a separations system 60 for isolation of desired oligomers products, such as 1-hexene and 1-octene, and recovery of ethylene. The separations system 60 also can be configured for catalyst deactivation. The main streams that exit the separations system 60 are the first stream 95, the second stream 63, the third stream 65, and the fourth stream 67. The first stream 95 contains predominantly ethylene along with less than 5 mass % $C_{4+}$ oligomers, and can have any other first stream of the first or second methods compositional properties disclosed herein. The first stream is recycled to reaction zone 20. The second stream 63 contains butene(s) such as 1-butene along with less than 10 mass % $C_{6+}$ oligomers (also referred to as a heavy gas purge stream), and can have any other second stream of the second method compositional properties disclosed herein. The third stream 65 contains at least 96 mass % hexene(s), the vast majority of which is 1-hexene, and can have any other third stream of the second method compositional properties disclosed herein. The fourth stream 67 contains at least 96 mass % octene(s), the vast majority of which is 1-octene, and can have any other fourth stream of the second method compositional properties disclosed herein.

Figure 2:
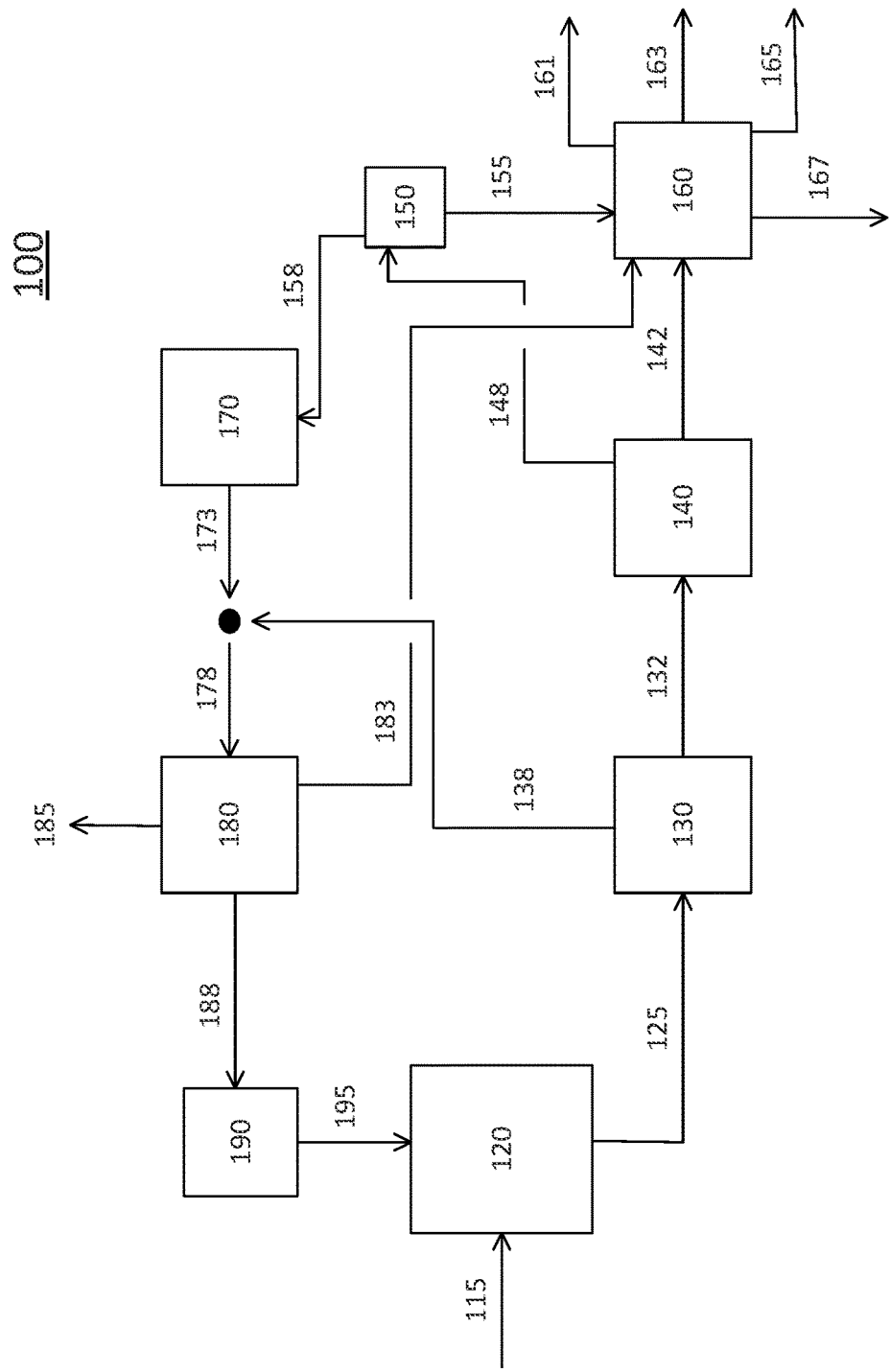
FIG. 2 illustrates an ethylene oligomerization reaction system consistent with another aspect of the present invention.

Referring now to FIG. 2, which illustrates another ethylene oligomerization reaction system 100 consistent with an aspect of the present invention. The system 100 can include an oligomerization reaction zone 120, a first stage separator 130, a second stage separator 140, a knock out pot 150, a liquid oligomer separations system 160, a first stage compressor 170, a knock out pot 180, and a second stage compressor 190. Feed streams 115 (representing one or more feed streams), oligomerization reaction zone 120, reaction zone effluent stream 125, second stream 163 (butene(s) and less than 10 mass % $C_{6+}$ oligomers), third stream 165 (at least 96 mass % hexene(s)), fourth stream 167 (at least 96 mass % octene(s)), and first stream 195 (ethylene and less than 5 mass % $C_{4+}$ oligomers) in FIG. 2 are generally the same as described for the similarly numbered components in FIG. 1. The separations system 60 in FIG. 1 has been significantly expanded to provide a separations scheme of FIG. 2 having additional, but not all potential, separation scheme details.

The reaction zone effluent stream 125 in FIG. 2 enters first stage separator 130, and a first liquid stream 132 and a first vapor stream 138 exit the first stage separator 130. The first liquid stream enters second stage separator 140, and a second liquid stream 142 and a second vapor stream 148 exits the second stage separator 140. The second liquid stream 142 is fed to the liquid oligomer separations system 160.

The second vapor stream 148 is fed to knock out pot 150, where first oligomer fraction 155 exits and is fed to the liquid oligomer separations system 160, whereas vapor stream 158 exits and is fed to first stage compressor 170. The light fraction 173 from compressor 170 is combined with the first vapor stream 138 to form combined light stream 178, which enters knock out pot 180. Exiting the knock out pot 180 are liquid stream 183, which is fed to the liquid oligomer separations system 160, light gas purge stream 185, and a lower pressure ethylene stream 188 that enters second stage compressor 190 to form the first stream 195, which is recycled to the reaction zone 120. In the liquid oligomer separations system 160 of FIG. 2, the main oligomer product streams are formed and isolated: third stream 165 (at least 96 mass % hexene(s)) and fourth stream 167 (at least 96 mass % octene(s)). The heavy gas purge stream containing butene(s) and less than 10 mass % $C_{6+}$ oligomers (second stream 163) and overhead light stream 161 also exit the liquid oligomer separations system 160.

In an aspect, the octene(s) stream (the third stream of the first method and the fourth stream of the second method) produced by methods described herein can comprise at least 95 mass %, 96 mass %, 96.5 mass %, 97 mass %, 97.5 mass %, 98.5 mass %, or 99 mass % 1-octene, based on total octene(s) in the third stream of the first method and the fourth stream of the second method. In other aspects, the octene(s) stream (the third stream of the first method and the fourth stream of the second method) produced by methods described herein can contain from 95 mass % to 99.9 mass %, from 96 mass % to 99.9 mass %, from 96.5 mass % to 99.9 mass %, from 97 mass % to 99.9 mass %, from 97.5 mass % to 99.9 mass %, from 98 mass % to 99.9 mass %, or from 98.5 mass % to 99.9 mass % 1-octene, based on total octene(s) in the third stream of the first method and the fourth stream of the second method.

In an aspect, the hexene(s) stream (the third stream of the second method) produced by methods described herein can comprise at least 90 mass %, 92.5 mass, 95 mass %, 97 mass %, 98 mass %, 98.5 mass %, or 99 mass % 1-hexene based on total hexene(s) in the third stream of the second method. In other aspects, the hexene(s) stream (the third stream of the second method) can contain from 90 mass % to 99.9 mass %, from 92.5 mass % to 99.9 mass %, from 95 mass % to 99.9 mass %, from 97 mass % to 99.9 mass %, from 98 mass % to 99.9 mass %, from 98.5 mass % to 99.9 mass %, or from 99 mass % to 99.9 mass % 1-hexene, based on total hexene(s) in the third stream of the second method.

Catalyst Systems

The methods disclosed herein can utilize a catalyst system (or catalyst system mixture) comprising i) a heteroatomic ligand transition metal compound complex and an organoaluminum compound or ii) a heteroatomic ligand, a transition metal compound, and an organoaluminum compound; alternatively, a heteroatomic ligand transition metal compound complex and an organoaluminum compound; or alternatively, a heteroatomic ligand, a transition metal compound, and an organoaluminum compound. In an aspect, the catalyst system (or catalyst system mixture) can further comprise (optionally) a catalyst system organic medium. In some aspects, the catalyst system (or catalyst system mixture) comprising i) a heteroatomic ligand transition metal compound complex and an organoaluminum compound or ii) a heteroatomic ligand, a transition metal compound, and an organoaluminum compound) can be introduced into the reaction mixture within the reaction zone. In other aspects, at least one of i) a heteroatomic ligand transition metal compound complex and an organoaluminum compound or ii) a heteroatomic ligand, a transition metal compound, and an organoaluminum compound) can be separately introduced into the reaction mixture within the reaction zone from other components of the catalyst system (or catalyst system mixture). The heteroatomic ligand, the transition metal compound, the heteroatomic ligand transition metal compound complex, the heteroatomic ligand of the heteroatomic ligand transition metal compound complex, the transition metal compound of the heteroatomic ligand transition metal compound, the organoaluminum compound, and the optional catalyst system organic medium are independent elements of the processes and reaction systems described herein and are independently described herein. These independently described catalyst system (or catalyst system mixture) elements can be utilized in any combination, and without limitation, to further describe the processes and reaction systems provided herein.

In an aspect, the transition metal atom of the heteroatomic ligand transition metal compound complex or the transition metal compound, $MX_p$, can be any transition metal atom. In an embodiment, the transition metal atom of the transition metal compound can comprise, or consist essentially of, a Group 3-12, a Group 4-10, a Group 6-9, or a Group 7-8 transition metal. In some embodiments, the transition metal atom of the transition metal compound can comprise, or consist essentially of, a Group 4 transition metal; alternatively, a Group 5 transition metal; alternatively, a Group 6 transition metal; alternatively, a Group 7 transition metal; alternatively, a Group 8 transition metal; alternatively, a Group 9 transition metal; or alternatively, a Group 10 transition metal. In an embodiment, the transition metal atom of the transition metal compound can comprise, or consist essentially of, titanium, zirconium, hafnium, vanadium, niobium, tantalum, chromium, molybdenum, tungsten, manganese, iron, cobalt, nickel, palladium, platinum, copper, or zinc; alternatively, titanium, zirconium, vanadium, chromium, molybdenum, tungsten, iron, cobalt, nickel, palladium, or platinum; alternatively, chromium, iron, cobalt, or nickel; alternatively, titanium, zirconium, or hafnium; alternatively, vanadium or niobium; alternatively, chromium, molybdenum, or tungsten; alternatively, iron or cobalt; or alternatively, nickel, palladium, platinum, copper, or zinc. In other embodiments, the metal salt can comprise titanium; alternatively, zirconium; alternatively, hafnium; alternatively, vanadium; alternatively, niobium; alternatively, tantalum; alternatively, chromium; alternatively, molybdenum; alternatively, tungsten; alternatively, manganese; alternatively, iron; alternatively, cobalt; alternatively, nickel; alternatively, palladium; alternatively, platinum; alternatively, copper; or alternatively, zinc. Generally, the transition metal atom of the heteroatomic ligand transition metal compound complex or the transition metal compound, $MX_p$, can have any positive oxidation state available to the transition metal atom. In an embodiment, the transition metal atom can have an oxidation state of from +2 to +6; alternatively, from +2 to +4; or alternatively, from +2 to +3. In some embodiments, the transition metal atom of the transition metal compound, $MX_p$, can have an oxidation state of +1; alternatively, +2; alternatively, +3; or alternatively, +4.

The methods disclosed herein can utilize a catalyst system (or catalyst system mixture) comprising i) a heteroatomic ligand chromium compound complex and an organoaluminum compound or ii) a heteroatomic ligand, a chromium compound, and an organoaluminum compound; alternatively, a heteroatomic ligand chromium compound complex and an organoaluminum compound; or alternatively, a heteroatomic ligand, a chromium compound, and an organoaluminum compound. In an aspect, the catalyst system (or catalyst system mixture) can further comprise (optionally) a catalyst system organic medium. In some aspects, the catalyst system (or catalyst system mixture) comprising i) a heteroatomic ligand chromium compound complex and an organoaluminum compound or ii) a heteroatomic ligand, a chromium compound, and an organoaluminum compound) can be introduced into the reaction mixture within the reaction zone. In other aspects, at least one of i) a heteroatomic ligand chromium compound complex and an organoaluminum compound or ii) a heteroatomic ligand, a chromium compound, and an organoaluminum compound) can be separately introduced into the reaction mixture within the reaction zone from other components of the catalyst system (or catalyst system mixture). The heteroatomic ligand, the chromium compound, the heteroatomic ligand chromium compound complex, the heteroatomic ligand of the heteroatomic ligand chromium compound complex, the chromium compound of the heteroatomic ligand chromium compound, the organoaluminum compound, and the optional catalyst system organic medium are independent elements of the processes and reaction systems described herein and are independently described herein. These independently described catalyst system (or catalyst system mixture) elements can be utilized in any combination, and without limitation, to further describe the processes and reaction systems provided herein.

Non-limiting examples of suitable catalyst system organic mediums include hydrocarbons, such as aromatic hydrocarbons. Aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene. In a particular aspect of this invention, the catalyst system organic medium can comprise, or consist essentially of, or consist of, ethylbenzene.

Generally, the heteroatomic ligand or the heteroatomic ligand of the heteroatomic ligand chromium compound complex can be any heteroatomic ligand, which when utilized in the catalyst systems (or catalyst system mixtures) described herein for the processes and/or reaction systems described herein, can form an oligomer product in the reaction zone. In an aspect, the heteroatomic ligand or the heteroatomic ligand of the heteroatomic ligand chromium compound complex can be a neutral heteroatomic ligand or an anionic heteroatomic ligand; alternatively, a neutral heteroatomic ligand; or alternatively, an anionic heteroatomic ligand. In an aspect, the neutral heteroatomic ligand can comprise one or more heteroatomic complexing moieties; alternatively, two heteroatomic complexing; or alternatively, three heteroatomic complexing moieties. In an aspect, the anionic heteroatomic ligand can also comprise one or more neutral heteroatomic complexing moieties; alternatively, two heteroatomic complexing; or alternatively, three heteroatomic complexing moieties. In an aspect, the each neutral heteroatomic complexing moiety of the neutral ligand or the anionic ligand comprising a neutral heteroatomic complexing moiety independently can be an ether group, a sulfide group, an amine group, an imine group, a phosphine group, a phosphinite group, a phosphonite group, or a phosphite group; alternatively, an ether group, a sulfide group, an amine group, an imine group, or a phosphine group; alternatively, an ether group; alternatively, a sulfide group; alternatively, an amine group; alternatively, an imine group; or alternatively, a phosphine group. In an aspect, the anion atom of the anionic heteroatomic ligand (which forms a covalent or ionic bond with the chromium of the chromium compound) can be an anionic carbon atom, an anionic oxygen atom, or an anion nitrogen atom; alternatively, an anionic carbon atom; alternatively, an anionic oxygen atom; or alternatively, an anion nitrogen atom.

In any aspect, the heteroatomic ligand or the heteroatomic ligand of the heteroatomic ligand chromium compound complex can comprise, can consist essentially of, or can be, an $N^2$-phosphinyl formamidine, an $N^2$-phosphinyl amidine, an $N^2$-phosphinyl guanidine, a heterocyclic 2-[(phosphinyl)aminyl]imine, or any combination thereof; alternatively, an $N^2$-phosphinyl formamidine; alternatively, an $N^2$-phosphinyl amidine; alternatively, an $N^2$-phosphinyl guanidine; or alternatively, a heterocyclic 2-[(phosphinyl)aminyl]imine Generally, the an $N^2$-phosphinyl formamidine can have Structure NPF1, the $N^2$-phosphinyl amidine can have Structure NPA1, the $N^2$-phosphinyl guanidine can have Structure Gu1, Structure Gu2, Structure Gu3, Structure Gu4, or Structure Gu5, and the heterocyclic 2-[(phosphinyl)aminyl]imine can have structure HCPA1. In some aspects, the $N^2$-phosphinyl guanidine have Structure Gu2, Structure Gu3, or Structure Gu4; alternatively, Structure Gu1; alternatively, Structure Gu2; alternatively, Structure Gu3; alternatively, Structure Gu4; or alternatively Structure Gu5.

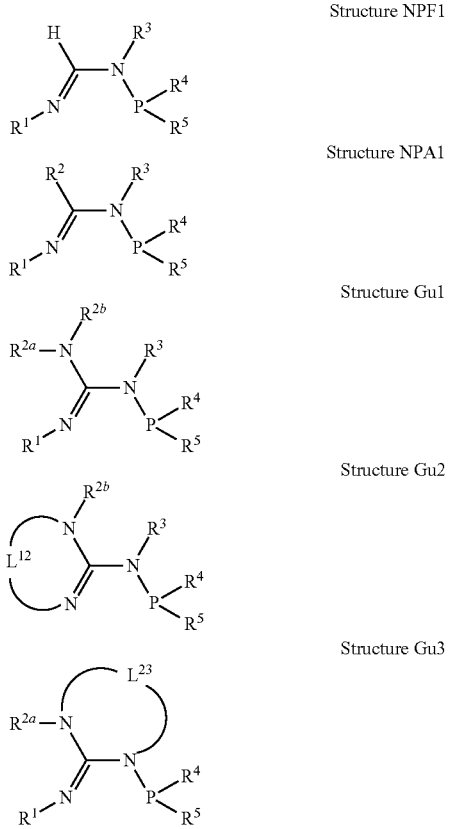

Structure NPF1

Structure NPA1

Structure Gu1

Structure Gu2

Structure Gu3

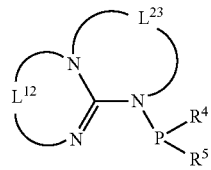

Structure Gu4

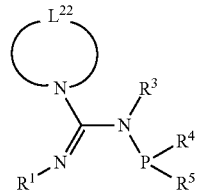

Structure Gu5

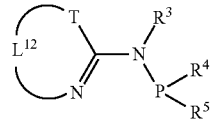

Structure HCPA1

In any aspect, the heteroatomic ligand chromium compound complex can comprise, can consist essentially of, or can be, an $N^2$-phosphinyl formamidine chromium compound complex, an $N^2$-phosphinyl amidine chromium compound complex, an $N^2$-phosphinyl guanidine chromium compound complex, a heterocyclic 2-[(phosphinyl)aminyl] imine chromium compound complex, or any combination thereof; alternatively, an $N^2$-phosphinyl formamidine chromium compound complex; alternatively, an $N^2$-phosphinyl amidine chromium compound complex; alternatively, an $N^2$-phosphinyl guanidine chromium compound complex; alternatively, an $N^2$-phosphinyl guanidine chromium compound complex; or alternatively, a heterocyclic 2-[(phosphinyl)aminyl]imine chromium compound complex. Generally, the an $N^2$-phosphinyl formamidine chromium compound complex can have Structure NPFCr1, the $N^2$-phosphinyl amidine chromium compound complex can have Structure NPACr1, the $N^2$-phosphinyl guanidine chromium compound complex can have Structure GuCr1, Structure GuCr2, Structure GuCr3, Structure GuCr4, or Structure GuCr5, and the heterocyclic 2-[(phosphinyl)aminyl]imine chromium compound complex can have Structure HCPACr1. In some aspects, the $N^2$-phosphinyl guanidine chromium compound complex have Structure GuCr2, Structure GuCr3, or Structure GuCr4; alternatively, Structure GuCr1; alternatively, Structure GuCr2; alternatively, Structure GuCr3; alternatively, Structure GuCr4; or alternatively Structure GuCr5.

Structure NPFCr1

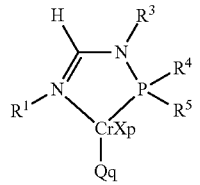

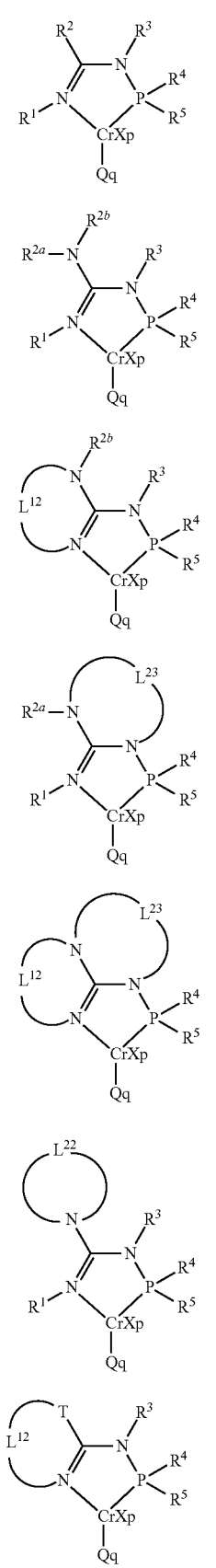

Structure NPACr1

Structure GuCr1

Structure GuCr2

Structure GuCr3

Structure GuCr4

Structure GuCr5

Structure HCPACr2

Within the $N^2$-phosphinyl formamidines, the $N^2$-phosphinyl formamidine chromium compound complexes, the $N^2$-phosphinyl amidines, the $N^2$-phosphinyl amidine chromium compound complexes, and the heterocyclic 2-[(phosphinyl)aminyl]imine chromium compound complexes the nitrogen participating in a double bond with the central carbon atom is referred to as the N' nitrogen and the nitrogen atom participating in a single bond with the central carbon atom is referred to as the $N^2$ nitrogen. Similarly, within the $N^2$-phosphinyl guanidines and the $N^2$-phosphinyl guanidine chromium compound complexes, the nitrogen participating in a double bond with the central carbon atom of the guanidine core is referred to as the N' nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that the guanidine group of the guanidine in the $N^2$-phosphinyl guanidines and the $N^2$-phosphinyl guanidine chromium complexes can be a portion of a larger group which does not contain guanidine in it name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an guanidine group) since it contains the defined general structure of the guanidine compound.

$R^1$, $R^3$, $R^4$, and $R^5$ within the $N^2$-phosphinyl formamidine structures and the $N^2$-phosphinyl formamidine chromium compound complex structures, $R^1$, $R^2$, $R^3$, $R^4$, and $R^5$ within the $N^2$-phosphinyl amidine structures and the $N^2$-phosphinyl amidine chromium compound complex structures, $R^1$, $R^{2a}$, $R^{2b}$, $R^3$, $R^4$, $R^5$, $L^{12}$, $L^{22}$, and $L^{23}$ within the $N^2$-phosphinyl guanidine structures and the $N^2$-phosphinyl guanidine chromium compound complex structures, and $L^{12}$, T, $R^3$, $R^4$, and $R^5$ within the heterocyclic 2-[(phosphinyl)aminyl]imine structures and heterocyclic 2-[(phosphinyl)aminyl]imine chromium compound complex structures are independently described herein and can be utilized in any combination and without limitation to further describe the $N^2$-phosphinyl formamidine structures, the $N^2$-phosphinyl formamidine chromium compound complex structures, the $N^2$-phosphinyl amidine structures, the $N^2$-phosphinyl amidine chromium compound complex structures, the $N^2$-phosphinyl guanidine structures, the $N^2$-phosphinyl guanidine chromium compound complex structures, the heterocyclic 2-[(phosphinyl)aminyl]imine structures, and the heterocyclic 2-[(phosphinyl)aminyl]imine chromium compound complex structures disclosed herein. $X_p$, Q, and q of the $N^2$-phosphinyl formamidine chromium compound complex structures, the $N^2$-phosphinyl amidine chromium compound complex structures, the $N^2$-phosphinyl guanidine chromium compound complex structures, and the heterocyclic 2-[(phosphinyl)aminyl]imine chromium compound complex structures are independently described herein and can be utilized in any combination, and without limitation, to further describe the $N^2$-phosphinyl formamidine chromium compound complex structures, the $N^2$-phosphinyl amidine chromium compound complex structures, the $N^2$-phosphinyl guanidine chromium compound complex structures, and the heterocyclic 2-[(phosphinyl)aminyl]imine chromium compound complex structures disclosed herein. Additionally, the independent descriptions of $X_p$, Q, and q can be combined, without limitation, with the independently described $R^1$, $R^2$, $R^{2a}$, $R^{2b}$, $R^3$, $R^4$, $R^5$, $L^{12}$, $L^{22}$, and $L^{23}$ to further describe the appropriate $N^2$-phosphinyl formamidine chromium compound complex structures, the $N^2$-phosphinyl amidine chromium compound complex structures, the $N^2$-phosphinyl guanidine chromium compound complex structures, and the heterocyclic 2-[(phosphinyl)aminyl] imine chromium compound complex structures contemplated herein.

Generally, $R^1$ of the $N^2$-phosphinyl formamidines, the $N^2$-phosphinyl formamidine chromium compound complexes, the $N^2$-phosphinyl amidines, the $N^2$-phosphinyl amidine chromium compound complexes, the $N^2$-phosphinyl guanidines, and/or the $N^2$-phosphinyl guanidine chromium compound complexes which have an $R^1$ group can be an organyl group; alternatively, an organyl group consisting of inert functional groups; or alternatively, a hydrocarbyl group. In an aspect, the $R^1$ organyl group can be a $C_1$ to $C_{20}$, a $C_1$ to $C_{15}$, a $C_1$ to $C_{10}$, or a $C_1$ to $C_5$ organyl group. In an aspect, the $R^1$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^1$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^1$ of the $N^2$-phosphinyl formamidines, the $N^2$-phosphinyl formamidine chromium compound complexes, the $N^2$-phosphinyl amidines, the $N^2$-phosphinyl amidine chromium compound complexes, the $N^2$-phosphinyl guanidines, and/or the $N^2$-phosphinyl guanidine chromium compound complexes which have an $R^1$ group can be an alkyl group, a substituted alkyl group, a cycloalkyl group, a substituted cycloalkyl group, an aryl group, a substituted aryl group, an aralkyl group, or a substituted aralkyl group; alternatively an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^1$ alkyl group can be a $C_1$ to $C_{20}$, a $C_1$ to $C_{10}$, or a $C_1$ to $C_5$ alkyl group. In any aspect disclosed herein, the $R^1$ substituted alkyl group can be a $C_1$ to $C_{20}$, a $C_1$ to $C_{10}$, or a $C_1$ to $C_5$ substituted alkyl group. In any aspect disclosed herein, the $R^1$ cycloalkyl group can be a $C_4$ to $C_{20}$, a $C_4$ to $C_{15}$, or a $C_4$ to $C_{10}$ cycloalkyl group. In any aspect disclosed herein, the $R^1$ substituted cycloalkyl group can be a $C_4$ to $C_{20}$, a $C_4$ to $C_{15}$, or a $C_4$ to $C_{10}$ substituted cycloalkyl group. In any aspect disclosed herein, the $R^1$ aryl group can be a $C_6$ to $C_{20}$, a $C_6$ to $C_{15}$, or a $C_6$ to $C_{10}$ aryl group. In any aspect disclosed herein, the $R^1$ substituted aryl group can be a $C_6$ to $C_{20}$, a $C_6$ to $C_{15}$, or a $C_6$ to $C_{10}$ substituted aryl group. In any aspect disclosed herein, the $R^1$ aralkyl group can be a $C_7$ to $C_{20}$, a $C_7$ to $C_{15}$, or a $C_7$ to $C_{10}$ aralkyl group. In any aspect disclosed herein, the $R^1$ substituted aralkyl group can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted $R^1$ group.

In an aspect, $R^1$ can be a methyl group, an ethyl group, a propyl group, a butyl group, a pentyl group, a hexyl group, a heptyl group, or an octyl group; or alternatively, a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group. In some aspects, the alkyl groups which can be utilized as $R^1$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^1$.

In an aspect, $R^1$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized as $R^1$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^1$ can be the same or different; alternatively, all the substituents of a multi-substituted cycloalkyl group can be the same; or alternatively, all the substituents of a multi-substituted cycloalkyl group can be different. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group (general or specific) which can be utilized as $R^1$.

In a non-limiting aspect, $R^1$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general and specific), dialkylcyclohexyl groups (general and specific), alkylcyclopentyl groups (general or specific), and/or dialkylcyclopentyl groups (general and specific) which can be utilized as $R^1$. Generally, the alkyl substituents of a dialkylcyclohexyl group or a dialkylcyclopentyl group can be the same; or alternatively, the alkyl substituents of a dialkylcyclohexyl group or a dialkylcyclopentyl group can be different. In some non-limiting aspects, $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^1$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^1$ can be a phenyl group, a substituted phenyl group; alternatively, a phenyl group; or alternatively, a substituted phenyl group. In an aspect, the substituted phenyl group, which can be utilized as $R^1$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^1$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^1$.

In a non-limiting aspect, $R^1$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^1$. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. In some non-limiting aspects, $R^1$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In an aspect, $R^1$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^1$.

Generally, $R^2$ of the $N^2$-phosphinyl amidines and/or the $N^2$-phosphinyl amidine chromium compound complexes can be an organyl group; alternatively, an organyl group consisting of inert functional groups; or alternatively, a hydrocarbyl group. In an aspect, the $R^2$ organyl group can be a $C_1$ to $C_{20}$, a $C_1$ to $C_{15}$, a $C_1$ to $C_{10}$, or a $C_1$ to $C_5$ organyl group. In an aspect, $R^2$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, $R^2$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^2$ of the $N^2$-phosphinyl amidines and/or the $N^2$-phosphinyl amidine chromium compound complexes can be an acyl group or a substituted acyl group; an acyl group; or alternatively, a substituted acyl group. In an aspect, the acyl group can be a $C_1$ to $C_{20}$, a $C_1$ to $C_{15}$, a $C_1$ to $C_{10}$, or a $C_1$ to $C_5$ acyl group. In an aspect, the substituted acyl group can be a $C_1$ to $C_{20}$, a $C_1$ to $C_{15}$, a $C_1$ to $C_{10}$, or a $C_1$ to $C_5$ a substituted acyl group. In some aspects, $R^2$ of the $N^2$-phosphinyl amidines and/or the $N^2$-phosphinyl amidine chromium compound complexes can be an alkanoyl group, a substituted alkanoyl group, a benzoyl group, or a substituted benzoyl group; alternatively, an alkanoyl group or a substituted alkanoyl group; alternatively, a benzoyl group, or a substituted benzoyl group; alternatively, an alkanoyl group; alternatively, a substituted alkanoyl group; alternatively, a benzoyl group; or alternatively, a substituted benzoyl group. In any aspect disclosed herein, the $R^2$ alkanoyl group can be a $C_1$ to $C_{20}$, a $C_1$ to $C_{10}$, or a $C_1$ to $C_5$ alkanoyl group. In any aspect disclosed herein, the $R^2$ substituted alkanoyl group can be a $C_1$ to $C_{20}$, a $C_1$ to $C_{10}$, or a $C_1$ to $C_5$ substituted $R^2$ alkanoyl group. In any aspect disclosed herein, the $R^2$ benzoyl group can be a $C_7$ to $C_{20}$, a $C_7$ to $C_{15}$, or a $C_7$ to $C_{10}$ benzoyl group. In any aspect disclosed herein, the $R^2$ substituted benzoyl group can be a $C_7$ to $C_{20}$, a $C_1$ to $C_{15}$, or a $C_1$ to $C_{10}$ substituted $R^2$ benzoyl group. Each substituent of a substituted alkanoyl group (general or specific), and/or substituted benzoyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe substituted alkanoyl groups and/or substituted benzoyl group which can be utilized as $R^2$.

In an aspect, $R^2$ of the $N^2$-phosphinyl amidines and/or the $N^2$-phosphinyl amidine chromium compound complexes can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^2$ of the $N^2$-phosphinyl amidine and/or the $N^2$-phosphinyl amidine chromium compound complexes can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^2$ alkyl group can be a $C_1$ to $C_{20}$, a $C_1$ to $C_{10}$, or a $C_1$ to $C_5$ alkyl group. In any aspect disclosed herein, the $R^2$ substituted alkyl group can be a $C_1$ to $C_{20}$, a $C_1$ to $C_{10}$, or a $C_1$ to $C_5$ substituted alkyl group. In any aspect disclosed herein, the $R^2$ cycloalkyl group can be a $C_4$ to $C_{20}$, a $C_4$ to $C_{15}$, or a $C_4$ to $C_{10}$ cycloalkyl group. In any aspect disclosed herein, the $R^2$ substituted cycloalkyl group can be a $C_4$ to $C_{20}$, a $C_4$ to $C_{15}$, or a $C_4$ to $C_{10}$ substituted cycloalkyl group. In any aspect disclosed herein, the $R^2$ aryl group can be a $C_6$ to $C_{20}$, a $C_6$ to $C_{15}$, or a $C_6$ to $C_{10}$ aryl group. In any aspect disclosed herein, the $R^2$ substituted aryl group can be a $C_6$ to $C_{20}$, a $C_6$ to $C_{15}$, or a $C_6$ to $C_{10}$ substituted aryl group. In any aspect disclosed herein, the $R^2$ aralkyl group can be a $C_7$ to $C_{20}$, a $C_7$ to $C_{15}$, or a $C_7$ to $C_{10}$ aralkyl group. In any aspect disclosed herein, the $R^2$ substituted aryl group can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^2$.

In an aspect, $R^2$ can be a methyl group, an ethyl group, a propyl group, a butyl group, a pentyl group, a hexyl group, a heptyl group, or an octyl group; or alternatively, a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group. In some aspects, the alkyl groups which can be utilized as $R^2$ can be substituted. Each substituent of a substituted alkyl group independently can be a halogen or a hydrocarboxy group; alternatively, a halogen; or alternatively, a hydrocarboxy group.

Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^2$.

In an aspect, $R^2$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized as $R^2$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^2$ can be the same or different; alternatively, all the substituents of a multi-substituted cycloalkyl group can be the same; or alternatively, all the substituents of a multi-substituted cycloalkyl group can be different. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^2$.

In a non-limiting aspect, $R^2$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^2$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects, $R^2$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^2$ can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^2$ can be a phenyl group, a substituted phenyl group; alternatively, a phenyl group; or alternatively, a substituted phenyl group. In an aspect, the substituted phenyl group, which can be utilized as $R^2$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^2$ can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^2$.

In a non-limiting aspect, $R^2$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^2$. Generally, the alkyl substituents of a dialkylphenyl group (general or specific) or trialkylphenyl group (general or specific) can be the same; or alternatively, the alkyl substituents of a dialkylphenyl group or trialkylphenyl group can be different. In some non-limiting aspects, $R^2$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^2$ can be a phenyl group, a 2-alkoxyphenyl group, or a 4-alkoxyphenyl group. In some non-limiting aspects, $R^2$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In another non-limiting aspect, $R^2$ can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some aspects, $R^2$ can be a phenyl group, a 2-fluorophenyl group, a 4-fluorophenyl group, or a 2,6-difluorophenyl group.

In an aspect, $R^2$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group which can be utilized as $R^2$.

In further aspects, $R^1$ and $R^2$ can be joined to form a ring or a ring system containing the carbon-nitrogen double bond of the $N^2$-phosphinyl amidines and/or the $N^2$-phosphinyl amidine chromium compound complexes. The joining of $R^1$ and $R^2$ can be designated as $L^{12r}$ and can be an organylene group; alternatively, an organylene group consisting of inert functional groups; alternatively, a hydrocarbylene group; or alternatively, an alkylene group. In an aspect, the $L^{12r}$ organylene group, when present, can be a $C_3$ to $C_{30}$, a $C_3$ to $C_{20}$, a $C_3$ to $C_{15}$, or a $C_3$ to $C_{10}$ organylene group. In some aspects, the $L^{12r}$ organylene group consisting of inert functional groups, when present, can be a $C_3$ to $C_{30}$, a $C_3$ to $C_{20}$, a $C_3$ to $C_{15}$, or a $C_3$ to $C_{10}$ organylene group consisting of inert functional groups. In other aspects, the $L^{12r}$ hydrocarbyl group, when present, independently can be a $C_3$ to $C_{30}$, a $C_3$ to $C_{20}$, a $C_3$ to $C_{15}$, or a $C_3$ to $C_{10}$ hydrocarbylene group.

In a further aspect, the $L^{12r}$ alkylene group, when present, independently can be a $C_3$ to $C_{30}$, a $C_3$ to $C_{20}$, a $C_3$ to $C_{15}$, or a $C_3$ to $C_{10}$ alkylene group. In an aspect, $L^{12}$, can be prop-1,3-ylene group, a but-1,3-ylene group, a 3-methylbut-1,3-ylene group (—$CH_2CH_2C(CH_3)_2$—), a but-1,4-ylene group, a 1,4-pent-1,4-ylene group.

Generally, T of the heterocyclic 2-[(phosphinyl)aminyl] imines and/or the heterocyclic 2-[(phosphinyl)aminyl]imine chromium compound complexes can be oxygen or sulfur. In and aspect, T of the heterocyclic 2-[(phosphinyl)aminyl] imines and/or the heterocyclic 2-[(phosphinyl)aminyl]imine chromium compound complexes can be oxygen; or alternatively, sulfur.

Generally, $R^{2a}$ and/or $R^{2b}$, of the $N^2$-phosphinyl guanidines and/or the $N^2$-phosphinyl guanidine chromium compound complexes which have an $R^{2a}$ and/or $R^{2b}$ group, independently can be hydrogen or an organyl group; alternatively, hydrogen or an organyl group consisting of inert functional groups; alternatively, hydrogen or a hydrocarbyl group; alternatively, hydrogen; alternatively, an organyl group; alternatively, an organyl group consisting of inert functional groups; or alternatively, a hydrocarbyl group. In an aspect, the $R^{2a}$ and/or $R^{2b}$ organyl groups independently can be a $C_1$ to $C_{20}$, a $C_1$ to $C_{15}$, a $C_1$ to $C_{10}$, or a $C_1$ to $C_5$ organyl group. In some aspects, the $R^{2a}$ and/or $R^{2b}$ organyl groups consisting of inert functional groups independently can be a $C_1$ to $C_{20}$, a $C_1$ to $C_{15}$, a $C_1$ to $C_{10}$, or a $C_1$ to $C_5$ organyl group consisting of inert functional groups. In other aspects, the $R^{2a}$ and/or $R^{2b}$ hydrocarbyl groups independently can be a $C_1$ to $C_{20}$, a $C_1$ to $C_{15}$, a $C_1$ to $C_{10}$, or a $C_1$ to $C_5$ hydrocarbyl group.

In an aspect, $R^{2a}$ and $R^{2b}$, of the $N^2$-phosphinyl guanidines and/or the $N^2$-phosphinyl guanidine chromium compound complexes which have an $R^{2a}$ and/or $R^{2b}$ organyl group, independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^{2a}$ and/or $R^{2b}$ alkyl group independently can be $C_1$ to $C_{20}$, a $C_1$ to $C_{10}$, or a $C_1$ to $C_5$ alkyl group. In any aspect disclosed herein, the $R^{2a}$ and/or $R^{2b}$ cycloalkyl group independently can be a $C_4$ to $C_{20}$, a $C_4$ to $C_{15}$, or a $C_4$ to $C_{10}$ cycloalkyl group. In any aspect disclosed herein, the $R^{2a}$ and/or $R^{2b}$ substituted cycloalkyl group independently can be a $C_4$ to $C_{20}$, a $C_4$ to $C_{15}$, or a $C_4$ to $C_{10}$ substituted cycloalkyl group. In any aspect disclosed herein, the $R^{2a}$ and/or $R^{2b}$ aryl group independently can be a $C_6$ to $C_{20}$, a $C_6$ to $C_{15}$, or a $C_6$ to $C_{10}$ aryl group. In any aspect disclosed herein, the $R^{2a}$ and/or $R^{2b}$ substituted aryl group independently can be a $C_6$ to $C_{20}$, a $C_6$ to $C_{15}$, or a $C_6$ to $C_{10}$ substituted aryl group. Each substituent of a substituted cycloalkyl group (general or specific) and/or a substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^{2a}$ and/or $R^{2b}$.

In an aspect, $R^1$ and $R^{2a}$ of the $N^2$-phosphinyl guanidines and/or the $N^2$-phosphinyl guanidine chromium compound complexes can be joined to form a group, $L^{12}$, wherein $L^{12}$, the $N^1$ nitrogen atom, and the $N^3$ nitrogen atom form a ring or a ring system. In another aspect, $R^3$ and $R^{2b}$ of the $N^2$-phosphinyl guanidines and/or the $N^2$-phosphinyl guanidine chromium compound complexes can be joined to form a group, $L^{23}$, wherein $L^{23}$, the $N^2$ nitrogen atom, and the $N^3$ nitrogen atom form a ring or a ring system. In an aspect, $L^{12}$ and/or $L^{23}$, of the $N^2$-phosphinyl guanidines and/or the $N^2$-phosphinyl guanidine chromium compound complexes which have an $L^{12}$ group and/or an $L^{23}$ group, independently can be an organylene group; alternatively, an organylene group consisting of inert functional groups; or alternatively, a hydrocarbylene group. The $L^{12}$ and/or $L^{23}$ organylene groups independently can be a $C_2$ to $C_{20}$, a $C_2$ to $C_{15}$, a $C_2$ to $C_{10}$, or a $C_2$ to $C_5$ organylene group. The $L^{12}$ and/or $L^{23}$ organylene groups consisting of inert functional groups independently can be a $C_2$ to $C_{20}$, a $C_2$ to $C_{15}$, a $C_2$ to $C_{10}$, or a $C_2$ to $C_5$ organylene group consisting of inert functional groups. The $L^{12}$ and/or $L^{23}$ hydrocarbylene groups independently can be a $C_2$ to $C_{20}$, a $C_2$ to $C_{15}$, a $C_2$ to $C_{10}$, or a $C_2$ to $C_5$ hydrocarbylene group.

In an aspect, $L^{12}$ of the $N^2$-phosphinyl guanidines, the $N^2$-phosphinyl guanidine chromium compound complexes, the heterocyclic 2-[(phosphinyl)aminyl]imines and/or the heterocyclic 2-[(phosphinyl)aminyl]imine chromium compound complexes which have an $L^{12}$ and $L^{23}$ of the $N^2$-phosphinyl guanidines and/or the $N^2$-phosphinyl guanidine chromium compound complexes which have an $L^{23}$, can have any structure provided in Table 1. In some aspects, $L^{12}$ and/or $L^{23}$ can have Structure 1L, Structure 2L, Structure 3L, Structure 4L or Structure 5L. In some aspects, $L^{12}$ and/or $L^{23}$ can have Structure 2L or Structure 3L; alternatively, Structure 4L or Structure 5L. In other aspects, $L^{12}$ and/or $L^{23}$ can have Structure 1L; alternatively, Structure 2L; alternatively, Structure 3L; alternatively, Structure 4L; or alternatively, Structure 5L. In some $N^2$-phosphinyl guanidine and $N^2$-phosphinyl guanidine chromium compound complex aspects, $L^{12}$ and/or $L^{23}$ can have Structure 6L. It should be noted that when $L^{12}$ or $L^{23}$ has Structure 6L the corresponding $R^{2b}$ or $R^{2a}$ is null because of the double bond link with the $N^3$ nitrogen atom of the $N^2$-phosphinyl guanidine and/or the $N^2$-phosphinyl guanidine chromium compound complex.

TABLE 1

Structures for Linking Groups $L^{12}$ and/or $L^{23}$.

| —(CR$^{L1}$R$^{L2}$)$_m$— | —CR$^{L3}$R$^{L4}$—CR$^{L5}$R$^{L6}$— | —CR$^{L3}$R$^{L4}$—CR$^{L7}$R$^{L8}$—CR$^{L5}$R$^{L6}$— |
|---|---|---|
| Structure 1L | Structure 2L | Structure 3L |
| —CR$^{L11}$=CR$^{L12}$— | | =CR$^{L27}$—CR$^{L28}$=CR$^{L29}$— |
| Structure 4L | | Structure 6L |

Structure 5L: a benzene ring with substituents $R^{L23}$, $R^{L24}$, $R^{L25}$, $R^{L26}$.

Within the structures of Table 1, the undesignated valences of $L^{12}$ and/or $L^{23}$ represent the points at which $L^{12}$ and/or $L^{23}$, when present, attach to the respective nitrogen atoms of the $N^2$-phosphinyl guanidine, and the $N^2$-phosphinyl guanidine chromium compound complex. Additionally, with the structures of Table 1, undesignated valences of $L^{12}$ represent the points at which $L^{12}$ attach to T and the respective nitrogen atom of the heterocyclic 2-[(phosphinyl) aminyl]imine and/or the heterocyclic 2-[(phosphinyl)aminyl]imine chromium compound complex. Generally, m can be an integer ranging from 2 to 5. In further aspects, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^L$, $R^{L6}$, $R^{L7}$, and $R^{L8}$, of the linking group having Structure 3L, $R^{L11}$ and $R^{L12}$ of the linking group having Structure 4L, $R^{L23}$, $R^{L24}$, $R^{L25}$, and $R^{L26}$ of the linking group having Structure 5L, $R^{L27}$, $R^{L28}$, and $R^{L29}$ of the linking group having Structure 6L independently can be a hydrogen or a non-hydrogen substituent group; or alternatively, hydrogen.

Non-hydrogen substituent groups (general and specific) are independently disclosed herein and can be utilized without limitation to further describe the linking group having Structure 1L, Structure 2L, Structure 3L, Structure 4L, Structure 5L, and/or Structure 6L. In an aspect, $L^{12}$ and/or $L^{23}$ independently can be an eth-1,2-ylene group (—CH$_2$CH$_2$—), an ethen-1,2-ylene group (—CH=CH—), a prop-1,3-ylene group (—CH$_2$CH$_2$CH$_2$—), a 1-methylethen-1,2-ylene group (—C(CH$_3$)=CH—), a but-1,3-ylene group (—CH$_2$CH$_2$CH(CH$_3$)—), a 3-methylbut-1,3-ylene group (—CH$_2$CH$_2$C(CH$_3$)$_2$—), or a phen-1,2-ylene group. In some non-limiting aspects, $L^{12}$ and/or $L^{23}$ be an eth-1,2-ylene group (—CH$_2$CH$_2$—), a prop-1,3-ylene group (—CH$_2$CH$_2$CH$_2$—), a 1-methylethen-1,2-ylene group (—C(CH$_3$)=CH—), a but-1,3-ylene group (—CH$_2$CH$_2$CH(CH$_3$)—), or a 3-methylbut-1,3-ylene group (—CH$_2$CH$_2$C(CH$_3$)$_2$—); alternatively, an eth-1,2-ylene group (—CH$_2$CH$_2$—), an ethen-1,2-ylene group (—CH=CH—), a prop-1,3-ylene group (—CH$_2$CH$_2$CH$_2$—), or a phen-1,2-ylene group; alternatively, an eth-1,2-ylene group (—CH$_2$CH$_2$—) or a prop-1,3-ylene group (—CH$_2$CH$_2$CH$_2$—); alternatively, an ethen-1,2-ylene group (—CH=CH—) or a phen-1,2-ylene group.

In an aspect, $L^{12}$ can have a structure that can comprise at least one substituent located on the carbon atom attached to the $N^1$ nitrogen atom of the $N^2$-phosphinyl guanidine and/or the $N^2$-phosphinyl guanidine chromium compound complex; alternatively, can comprise only one substituent located on the carbon atom attached to the $N^1$ nitrogen atom of the $N^2$-phosphinyl guanidine and/or the $N^2$-phosphinyl guanidine chromium compound complex; or alternatively, can comprise two substituents located on the carbon atom attached to the $N^1$ nitrogen atom of the $N^2$-phosphinyl guanidine and/or the $N^2$-phosphinyl guanidine chromium compound complex. In another aspect, $L^{12}$ can have a structure that can consist of one substituent located on the carbon atom attached to the $N^1$ nitrogen atom the $N^2$-phosphinyl guanidine and/or the $N^2$-phosphinyl guanidine chromium compound complex; or alternatively, can consist of two substituents located on the carbon atom attached to the $N^1$ nitrogen atom of the $N^2$-phosphinyl guanidine and/or the $N^2$-phosphinyl guanidine chromium compound complex.

In an aspect, $R^{2a}$ and $R^{2b}$ of the $N^2$-phosphinyl guanidines and/or the $N^2$-phosphinyl guanidine chromium compound complexes can be joined to form a group, $L^{22}$, wherein $R^{2a}$, $R^{2b}$, and the $N^3$ nitrogen (or $L^{22}$ and the $N^3$ nitrogen) form a ring or ring system. In an aspect, $L^{22}$ of the $N^2$-phosphinyl guanidines and/or the $N^2$-phosphinyl guanidine chromium compound complexes having an $L^2$ group can be an organylene group; alternatively, an organylene group consisting of inert functional groups; or alternatively, a hydrocarbylene group. The $L^{22}$ organylene group can be a $C_3$ to $C_{20}$, a $C_3$ to $C_{15}$, or a $C_3$ to $C_{10}$ organylene group. The $L^{22}$ organylene group consisting of inert functional groups can be a $C_3$ to $C_{20}$, a $C_3$ to $C_{15}$, or a $C_3$ to $C_{10}$ organylene group consisting of inert functional groups. The $L^{22}$ hydrocarbylene group can be a $C_4$ to $C_{20}$, a $C_4$ to $C_{15}$, or a $C_4$ to $C_{10}$ hydrocarbylene group.

In an aspect, $L^{22}$ can have any structure provided in Table 2. In some aspects, $L^{22}$ can have Structure 11L, Structure 12L, Structure 13L, Structure 14L, Structure 15L, or Structure 16L. In other aspects, $L^{22}$ can have Structure 11L; alternatively, Structure 12L; alternatively, Structure 13L; alternatively, Structure 14L; or alternatively, Structure 15L.

TABLE 2

Structures for Linking Groups $L^{22}$.

—(CR$^{L31}$R$^{L32}$)$_n$—
Structure 11L
—CR$^{L41}$R$^{L42}$—CR$^{L45}$R$^{L46}$R$^{L47}$R$^{L48}$CR$^{L43}$R$^{L44}$—
Structure 12L
—CR$^{L41}$R$^{L42}$—CR$^{L45}$R$^{L46}$—CR$^{L49}$R$^{L50}$—CR$^{L47}$R$^{L48}$—CR$^{L43}$R$^{L44}$—
Structure 13L
—CR$^{L41}$R$^{L42}$—CR$^{L45}$R$^{L46}$—O—CR$^{L47}$R$^{L48}$—CR$^{L43}$R$^{L44}$—
Structure 14L
—C$^{L51}$=CR$^{L53}$—CR$^{L54}$=CR$^{L52}$—
Structure 15L Within the structures of Table 2, the undesignated valences represent the points at which $L^{22}$ of the $N^2$-phosphinyl guanidine and/or the $N^2$-phosphinyl guanidine chromium compound complex, when present, attach to the $N^3$ nitrogen atom of the $N^2$-phosphinyl guanidine and/or the $N^2$-phosphinyl guanidine chromium compound complex. Generally, n can be an integer ranging from 4 to 7. In further aspects, n can be 4 or 5; alternatively, n can be 4; or alternatively, n can be 5. $R^{L31}$ and $R^{L32}$ of the linking group having Structure 11L, $R^{L41}$, $R^{L42}$, $R^{L43}$, $R^{L44}$, $R^{L45}$, $R^{L46}$, $R^{L47}$, and $R^{L48}$ of the linking group having Structure 12L, $R^{L41}$, $R^{L42}$, $R^{L43}$, $R^{L44}$, $R^{L45}$, $R^{L46}$, $R^{L47}$, $R^{L48}$, $R^{L49}$, and $R^{L50}$ of the linking group having Structure 13L, $R^{L41}$, $R^{L42}$, $R^{L43}$, $R^{L44}$, $R^{L45}$, $R^{L46}$, $R^{L47}$, and $R^{L48}$ of the linking group having Structure 14L, and $R^{L41}$, $R^{L42}$, $R^{L43}$, $R^{L44}$, $R^{L45}$, $R^{L46}$, $R^{L47}$, and $R^{L48}$ of the linking group having Structure 15L independently can be a hydrogen or a non-hydrogen substituent group; alternatively, hydrogen. Non-hydrogen substituent groups are independently disclosed herein and can be utilized without limitation to further describe the linking group having Structure 11L, Structure 12L, Structure 13L, Structure 14L, and/or Structure 15L. In an aspect, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; or alternatively, a but-1,4-ylene group, a pent-1,5-ylene group, or a bis(eth-2-yl)ether group.

Generally, $R^3$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl]imine chromium compound complexes which have an $R^3$ group can be hydrogen or an organyl group; hydrogen or an organyl group consisting of inert functional group; alternatively, hydrogen or a hydrocarbyl group; alternatively, hydrogen; alternatively, an organyl group; alternatively, an organyl group consisting of inert functional group; or alternatively, a hydrocarbyl group. In an aspect, the $R^3$ organyl group can be a $C_1$ to $C_{20}$, a $C_1$ to $C_{15}$, a $C_1$ to $C_{10}$, or a $C_1$ to $C_5$ organyl group. In an aspect, the $R^3$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^3$ hydrocarbyl group can be a, a $C_1$ to $C_{20}$, a $C_1$ to $C_{15}$, a $C_1$ to $C_{10}$, or a $C_1$ to $C_8$ hydrocarbyl group. In other aspects, $R^3$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl]imine chromium compound complexes which have an $R^3$ group can be a $C_1$ to $C_{30}$, a $C_1$ to $C_{20}$, a $C_1$ to $C_{15}$, a $C_1$ to $C_{10}$, or a $C_1$ to $C_5$ alkyl group. In yet other aspects, $R^3$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl]imine chromium compound complexes can be a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these substituent groups can be utilized to further describe the substituted phenyl groups which can be utilized as $R^3$ the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, and/or the $N^2$-phosphinyl guanidine chromium compound complexes having a non-hydrogen $R^3$ group.

Generally, $R^4$ and/or $R^5$ of the $N^2$-phosphinyl formamidines, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl]imine chromium compound complexes independently can be an organyl group; alternatively, an organyl group consisting of inert functional groups; or alternatively, a hydrocarbyl group. In an aspect, the $R^4$ and/or $R^5$ organyl groups can be a $C_1$ to $C_{20}$, a $C_1$ to $C_{15}$, a $C_1$ to $C_{10}$, or a $C_1$ to $C_5$ organyl group. In an aspect, the $R^4$ and/or $R^5$ organyl groups consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^4$ and/or $R^5$ hydrocarbyl groups can be a, a $C_1$ to $C_{20}$, a $C_1$ to $C_{15}$, a $C_1$ to $C_{10}$, or a $C_1$ to $C_5$ hydrocarbyl group. In an aspect, $R^4$ and/or $R^5$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl]imine chromium compound complexes independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect disclosed herein, the $R^4$ and/or $R^5$ alkyl groups independently can be a $C_1$ to $C_{20}$, a $C_1$ to $C_{10}$, or a $C_1$ to $C_5$ alkyl group. In any aspect disclosed herein, the $R^4$ and/or $R^5$ substituted alkyl groups independently can be a $C_1$ to $C_{20}$, a $C_1$ to $C_{10}$, or $C_1$ to $C_5$ substituted alkyl group. In any aspect disclosed herein, the $R^4$ and/or $R^5$ cycloalkyl groups independently can be a $C_4$ to $C_{20}$, a $C_4$ to $C_{15}$, or a $C_4$ to $C_{10}$ cycloalkyl group. In any aspect disclosed herein, the $R^4$ and/or $R^5$ substituted cycloalkyl groups independently can be a $C_4$ to $C_{20}$, a $C_4$ to $C_{15}$, or a $C_4$ to $C_{10}$ substituted cycloalkyl group. In any aspect disclosed herein, the $R^4$ and/or $R^5$ aryl groups independently can be a $C_6$ to $C_{20}$, a $C_6$ to $C_{15}$, or a $C_6$ to $C_{10}$ aryl group. In any aspect disclosed herein, the $R^4$ and/or $R^5$ substituted aryl group independently can be a $C_6$ to $C_{20}$, a $C_6$ to $C_{15}$, or a $C_6$ to $C_{10}$ substituted aryl group. In any aspect disclosed herein, the $R^4$ and/or $R^5$ aralkyl groups independently can be a $C_7$ to $C_{20}$, a $C_7$ to $C_{15}$, or a $C_7$ to $C_{10}$ aralkyl group. In any aspect disclosed herein, the $R^4$ and/or $R^5$ substituted aryl groups independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^4$ and/or $R^5$.

In an aspect, $R^4$ and $R^5$ independently can be a methyl group, an ethyl group, a propyl group, a butyl group, a pentyl group, a hexyl group, a heptyl group, or an octyl group; or alternatively, a methyl group, an ethyl group, an n-propyl (1-propyl) group, an iso-propyl (2-propyl) group, a 2-methyl-1-propyl group, a tert-butyl (2-methyl-2-propyl) group, or a neopentyl (2,2-dimethyl-1-propyl) group. In some aspects, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Substituent halogens and substituent hydrocarboxy (general and specific) groups are independently disclosed herein. These substituent halogens and substituent hydrocarboxy groups can be utilized without limitation to further describe a substituted alkyl group which can be utilized as $R^4$ and/or $R^5$.

In an aspect, $R^4$ and $R^5$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized for $R^4$ and/or $R^5$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect where the substituted cycloalkyl group (general or specific) has more the one substituent, the substituents can be the same or different; alternatively, the same; or alternatively, different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^4$ and/or $R^5$.

In a non-limiting aspect, $R^4$ and $R^5$ independently can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further described alkylcyclohexyl groups (general or specific), dialkylcyclohexyl groups (general or specific), alkylcyclopentyl groups (general or specific), and/or dialkylcyclopentyl groups (general or specific) which can be utilized as $R^4$ and/or $R^5$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects, $R^4$ and $R^5$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^4$ and $R^5$ independently can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^4$ and $R^5$ independently can be a phenyl group, a substituted phenyl group; alternatively, a phenyl group; or alternatively, a substituted phenyl group. In an aspect, the substituted phenyl group, which can be utilized for $R^4$ and/or $R^5$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^4$ and/or $R^5$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^4$ and/or $R^5$.

In a non-limiting aspect, $R^4$ and $R^5$ independently can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^4$ and/or $R^5$. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting aspects, $R^4$ and $R^5$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^4$ and $R^5$ can be a phenyl group, a 2-alkoxyphenyl group, or a 4-alkoxyphenyl group. In some non-limiting aspects, $R^4$ and/or $R^5$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In a non-limiting aspect, $R^4$ and $R^5$ independently can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some aspects, $R^4$ and $R^5$ independently can be a phenyl group, a 2-fluorophenyl group, a 4-fluorophenyl group, or a 2,6-difluorophenyl group.

In an aspect, $R^4$ and $R^5$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^4$ and/or $R^5$.

In further aspects, $R^4$ and $R^5$ can be joined to form a ring or a ring system containing the phosphorus atom. The joining of $R^4$ and $R^5$ can be designated as $L^{45}$ and can be an organylene group; alternatively, an organylene group consisting of inert functional groups; alternatively, a hydrocarbylene group; or alternatively, an alkylene group. In an aspect, the $L^{45}$ organylene group, when present, can be a $C_4$ to $C_{30}$, a $C_4$ to $C_{20}$, a $C_4$ to $C_{15}$, or a $C_4$ to $C_{10}$ organylene group. In an aspect, the $L^{45}$ organylene group consisting of inert functional groups, when present, can be a $C_4$ to $C_{30}$, a $C_4$ to $C_{20}$, a $C_4$ to $C_{15}$, or a $C_4$ to $C_{10}$ organylene group consisting of inert functional groups. In an aspect, the $L^{45}$ hydrocarbyl group, when present, independently can be a $C_4$ to $C_{30}$, a $C_4$ to $C_{20}$, a $C_4$ to $C_{15}$, or a $C_4$ to $C_{10}$ hydrocarbylene group. In a further aspect, the $L^{45}$ alkylene group, when present, independently can be a $C_4$ to $C_{30}$, a $C_4$ to $C_{20}$, a $C_4$ to $C_{15}$, or a $C_4$ to $C_{10}$ alkylene group. In an aspect, $L^{45}$ can be a but-1,4-ylene group, a 1,4-diphenylbut-1,4-ylene group, a 1,4-di(2-methylphenyl)but-1,4-ylene group, 1,4-di(4-methylphenyl)but-1,4-ylene group, 1,4-di(4-t-butylphenyl)but-1,4-ylene group, a 1,4-di(3,5-dimethylphenyl)but-1,4-ylene group, a pent-1,4-ylene group, a 1-phenylpenta-1,4-ylene group, a 4-phenylpenta-1,4-ylene group, a hex-2,5-ylene group, a 2,2'-biphenylene group, a 2,2'-(methandiyl)diphenylene group, or a 2,2'-(1,2-ethandiyl)diphenylene group.

In an aspect, the heteroatomic ligand or the heteroatomic ligand of the heteroatomic ligand chromium compound complex can have the formula $(R^{1s})_m X^{1s}(L^{1s})X^{2s}(R^{2s})_n$ while the heteroatomic ligand chromium compound complex can have the formula:

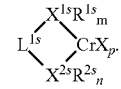

In some aspects, the heteroatomic ligand or the heteroatomic ligand of the heteroatomic ligand chromium compound complex can have two groups capable of being described by the formula $(R^{1s})_m X^{1s}(L^{1s})X^{2s}(R^{2s})_n$. In instances wherein the heteroatomic ligand can have two groups capable of being described by the formula $(R^{1s})_m X^{1s}(L^{1s})X^{2s}(R^{2s})_n$, the two $L^{1s}$ groups are linked and the heteroatomic ligand and the heteroatomic ligand chromium compound complex can have the formulas:

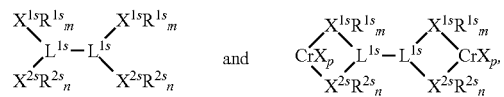

respectively.

In the heteroatomic ligand or the heteroatomic ligand of the heteroatomic ligand chromium compound complex having formula $(R^{1s})_m X^{1s}(L^{1s})X^{2s}(R^{2s})_n$ or having two linked $(R^{1s})_m X^{1s}(L^{1s})X^{2s}(R^{2s})_n$ groups, each $X^{1s}$ and each $X^{2s}$ independently can be selected from the group consisting of N, P, O, and S; each $L^{1s}$ can be an independent linking group between the respective $X^{1s}$s and $X^{2s}$s; each m and each n independently can be 1 or 2; and each $R^{1s}$ and each $R^{2s}$ independently can be a hydrogen, an organyl group (or alternatively, an organyl group consisting of inert functional group; or alternatively, a hydrocarbyl group), or a heterohydrocarbyl group, where when there are two or more $R^{1ss}$ and/or two $R^{2s}$s, each $R^{1s}$ can be the same or different (alternatively, the same; or alternatively, different) and/or each $R^{2s}$ can be the same or different (alternatively, the same; or alternatively, different). $L^{1s}$, $X^{1s}$, $X^{2s}$, $R^{1s}$, $R^{2s}$, m, and n are independent elements of any heteroatomic ligand or any heteroatomic ligand of the heteroatomic ligand chromium compound complex which have an $L^{1s}$, $X^{1s}$, $X^{2s}$, $R^{1s}$, $R^{2s}$, m, and/or n and are independently described herein. These independent descriptions of $L^{1s}$, $X^{1s}$, $X^{2s}$, $R^{1s}$, $R^{2s}$, m, and n can be utilized without limitation, and in any combination, to further describe any heteroatomic ligand or any heteroatomic ligand of the heteroatomic ligand chromium compound complex which have an $L^{1s}$, $X^{1s}$, $X^{2s}$, $R^{1s}$, $R^{2s}$, m, and/or n. Additionally, $CrX_p$, is an independent element of the heteroatomic ligand chromium compound complex, and is independently described herein, and can be utilized without limitation, and in any combination with $L^{1s}$, $X^{1s}$, $X^{2s}$, $R^{1s}$, $R^{2s}$, m, and n of the heteroatomic ligand to further describe the heteroatomic ligand chromium compound complexes contemplated herein.

In an aspect, each $X^{1s}$ and each $X^{2s}$ of any heteroatomic ligand or any heteroatomic ligand of any heteroatomic ligand chromium compound complex described herein having an $X^{1s}$ and/or $X^{2s}$ can be independently selected from N, P, O, and S; alternatively, independently selected from N and P; or alternatively, independently selected from O and S. In some aspects, each $X^{1s}$ and each $X^{2s}$ can be N; alternatively, P; alternatively, O; or alternatively, S. Each m and each n of any heteroatomic ligand or any heteroatomic ligand of any heteroatomic ligand chromium compound complex described herein having an m and/or n can be independently selected from 1 or 2; alternatively, 1; or alternatively, 2. Is some particular aspects, each m and/or each n can be 1 when $X^{1s}$ and/or $X^{2s}$, respectively, is O or S; alternatively, O; or alternatively, S. In some other particular aspects, each m and/or each n can be 2 when $X^{1s}$ and/or $X^{2s}$, respectively, is N or P; alternatively, N; or alternatively, P.

In a non-limiting aspect, the heteroatomic ligand can have the formula $R^{1s}S(L^{1s})SR^{2s}$, $(R^{1s})_2P(L^{1s})P(R^{2s})_2$, or $(R^{1s})_2N(L^{1s})N(R^{2s})_2$; alternatively, $R^{1s}S(L^{1s})SR^{2s}$; alternatively, $(R^{1s})_2P(L^{1s})P(R^{2s})_2$; or alternatively, $(R^{1s})_2N(L^{1s})N(R^{2s})_2$ while the heteroatomic ligand chromium compound complex can have any one of the formulas

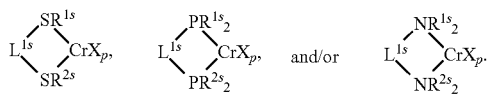

In non-limiting aspects where the heteroatomic ligand or the heteroatomic ligand of the heteroatomic ligand chromium compound complex has two linked heteroatomic groups, the heteroatomic ligand can have the formula selected from one or more of

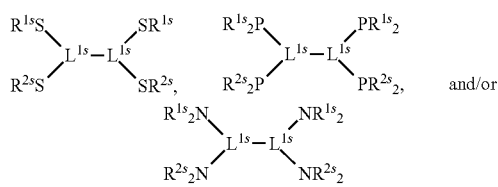

while the heteroatomic ligand chromium compound complex can have any one of the formulas

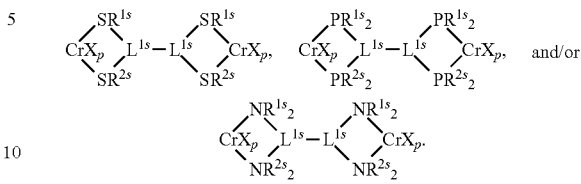

In an aspect, each $L^{1s}$ of any heteroatomic ligand or any heteroatomic ligand of the heteroatomic ligand chromium compound complex described herein independently can be any group capable of linking group $X^{1s}$ and $X^{2s}$ (and other $L^{1s}$ group when the heteroatomic ligand or heteroatomic ligand of the heteroatomic ligand chromium compound complex when there are more than one $L^{1s}$ group). In some aspects, each $L^{1s}$ independently can be an organylene group, an amin-di-yl group, or a phosphin-di-yl group; alternatively, an organylene group consisting of inert functional groups, an amin-di-yl group, or a phosphin-di-yl group; alternatively, a hydrocarbylene group, an amin-di-yl group, or a phosphin-di-yl group; alternatively an amin-di-yl group or a phosphin-di-yl group; alternatively, an organylene group; alternatively, an organylene group consisting of inert functional groups; alternatively, a hydrocarbylene group; alternatively, an amin-di-yl group; or alternatively, a phosphin-di-yl group. When there is more than one $L^{1s}$ group in the heteroatomic ligand or heteroatomic ligand of the heteroatomic ligand chromium compound complex, each $L^{1s}$ independently can be an organic, an amine group, or a phosphine group; alternatively, an organic group consisting of inert functional groups, an amine group, or a phosphine group; alternatively, a hydrocarbon group, an amine group, or a phosphine group; alternatively an amine group or a phosphine group; alternatively, an organic group; alternatively, an organic group consisting of inert functional groups; alternatively, a hydrocarbon group; alternatively, an amine group; or alternatively, a phosphine group. In an aspect, the $L^{1s}$ organylene group or organic group can be a $C_1$ to $C_{20}$, a $C_1$ to $C_{15}$, a $C_1$ to $C_{10}$, or, a $C_1$ to $C_5$ organylene group or organic group. In an aspect, the $L^{1s}$ organylene group consisting of inert functional groups can be a $C_1$ to $C_{20}$, a $C_1$ to $C_{15}$, a $C_1$ to $C_{10}$, or, a $C_1$ to $C_5$ organylene or organic group consisting of inert functional groups. In an aspect, the $L^{1s}$ hydrocarbylene group can be a $C_1$ to $C_{20}$, a $C_1$ to $C_{15}$, a $C_1$ to $C_{10}$, or a $C_1$ to $C_5$ hydrocarbylene group or hydrocarbon group. In an aspect, the amin-di-yl or amine group can be a $C_1$ to $C_{30}$, a $C_1$ to $C_{20}$, a $C_1$ to $C_{15}$, or a $C_1$ to $C_{10}$ amin-di-yl or amine group. In an aspect, the phosphin-di-yl or phosphine group can be a $C_1$ to $C_{30}$, a $C_1$ to $C_{20}$, a $C_1$ to $C_{15}$, or a $C_1$ to $C_{10}$ phosphin-di-yl or phosphine group.

In an aspect, each $L^{1s}$ organylene or organic group can have the formula $-(L^{3s})NR^{5s}(L^{4s})-$ or $-(L^{3s})PR^{5s}(L^{4s})-$; alternatively, $-(L^{3s})NR^{5s}(L^{4s})-$; or alternatively, $-(L^{3s})PR^{5s}(L^{4s})-$. In an aspect, the each amin-di-yl group can have the formula $-N(R^{5s})-$. In an aspect, each phosphin-di-yl group can have the formula $-P(R^{5s})-$. In these $L^{1s}$ group formulas, the dashes represent the undesignated valance to which the $X^{1s}$ and $X^{2s}$ of the heteroatomic ligand or the heteroatomic ligand of the heteroatomic ligand of the heteroatomic ligand chromium compound complex described herein attach. When there is more than one $L^{1s}$ group in the heteroatomic ligand or heteroatomic ligand of the heteroatomic ligand chromium compound complex, the $R^{5s}$ of each $L^{1s}$ group can be combined into a linking group designated as $L^{2s}$. In some non-limiting aspects, the heteroatomic ligand can have Structure PNP1, Structure PNP2, Structure NRN, Structure PRP, Structure SRN, Structure PRN, and Structure NRP; alternatively, Structure PNP1 or Structure PNP2; alternatively, Structure PRP, Structure SRN, or Structure PRN; alternatively, Structure PNP1; alternatively, Structure PNP2; alternatively, Structure NRN; alternatively, Structure PRP; alternatively, Structure SRN; alternatively, Structure PRN; or alternatively, Structure NRP. In some non-limiting aspects, the heteroatomic ligand chromium compound complex having a heteroatomic ligand $(R^{1s})_m X^{1s}(L^{1s})X^{2s}(R^{2s})_n$ which can be utilized in catalyst systems described herein can have Structure PNCr1, Structure PNPCr2, Structure NRNCr, Structure PRPCr, Structure SRNCr, Structure PRNCr, and Structure NRPCr; alternatively, Structure PNPCr1 or Structure PNPCr2; alternatively, Structure PRPCr, Structure SRNCr, or Structure PRNCr; alternatively, Structure PNPCr1; alternatively, Structure PNPCr2; alternatively, Structure NRNCr; alternatively, Structure PRPCr; alternatively, Structure SRNCr; alternatively, Structure PRNCr; or alternatively, Structure NRPCr.

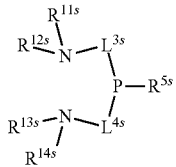

Structure PNP1

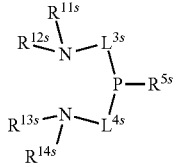

Structure PNP2

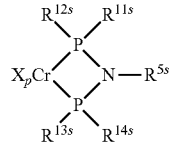

Structure NRN

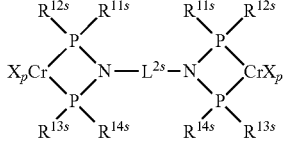

Structure PRP

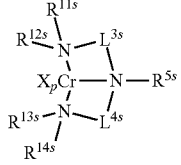

Structure SRN

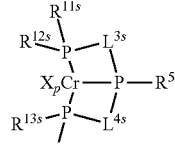

Structure PRN

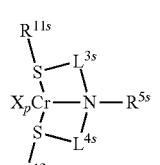

Structure NRP

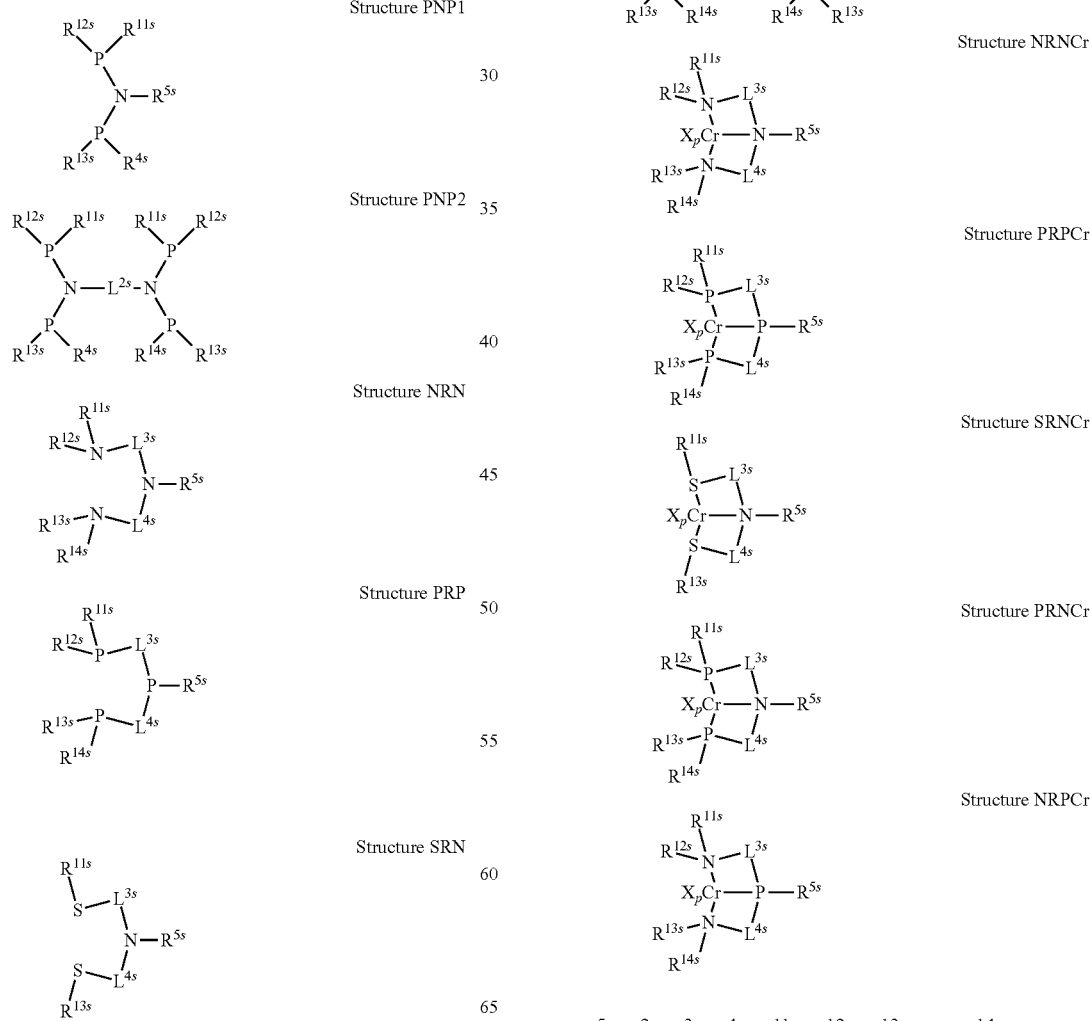

Structure PNPCr1

Structure PNPCr2

Structure NRNCr

Structure PRPCr

Structure SRNCr

Structure PRNCr

Structure NRPCr

The $R^{5s}$, $L^{2s}$, $L^{3s}$, $L^{4s}$, $R^{11s}$, $R^{12s}$, $R^{13s}$, and $R^{14s}$ are each independent elements of the heteroatomic ligands having Structure PNP1, Structure PNP2, Structure NRN, Structure PRP, Structure SRN, Structure PRN, or Structure NRP, and/or the heteroatomic ligand of the heteroatomic ligand chromium compound complexes having Structure PNPCr1, Structure PNPCr2, Structure NRNCr, Structure PRPCr, Structure SRNCr, Structure PRNCr, and Structure NRPCr in which they occur and are independently described herein. The independent descriptions of $R^{5s}$, $L^{2s}$, $L^{3s}$, $L^{4s}$, $R^{11s}$, $R^{12s}$, $R^{13s}$, and $R^{14s}$ can be utilized without limitation, and in any combination, to further describe the heteroatomic ligand structures and/or the heteroatomic ligand chromium compound complex structure in which they occur. Similarly, X and p are independent elements of the heteroatomic ligand chromium compound complexes having Structure PNCr1, Structure PNPCr2, Structure NRNCr, Structure PRPCr, Structure SRNCr, Structure PRNCr, and Structure NRPCr and are independently described herein. The independent description of X and p can be utilized without limitation, and in any combination, with the independently described $R^{5s}$, $L^{2s}$, $L^{3s}$, $L^{4s}$, $R^{11s}$, $R^{12s}$, $R^{13s}$, and $R^{14s}$ provided herein to further describe any heteroatomic ligand chromium compound complex having Structure PNPCr1, Structure PNPCr2, Structure NRNCr, Structure PRPCr, Structure SRNCr, Structure PRNCr, and/or Structure NRPCr.

Generally, $R^{1s}$, $R^{2s}$, $R^{11s}$, $R^{12s}$, $R^{13s}$, and/or $R^{14s}$, of any heteroatomic ligand structure depicted herein and/or any heteroatomic ligand chromium compound complex depicted herein having an $R^{1s}$, $R^{2s}$, $R^{11s}$, $R^{12s}$, $R^{13s}$, and/or $R^{14s}$ group, independently can be an organyl group; alternatively, an organyl group consisting of inert functional groups; or alternatively, a hydrocarbyl group. In an aspect, the organyl group which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C_5$ organyl group. In an aspect, the organyl group consisting of inert functional groups which can be utilized as $R^{1s}$, $R^{2s}$, $R^{11s}$, $R^{12s}$, $R^{1s3}$, and/or $R^{14s}$ independently can be a $C_1$ to $C_{20}$, a $C_1$ to $C_{15}$, a $C_1$ to $C_{10}$, or a $C_1$ to $C_5$ organyl group consisting of inert functional groups. In an aspect, the hydrocarbyl group which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C^5$ hydrocarbyl group.

In an aspect, each $R^{1s}$, $R^{2s}$, $R^{11s}$, $R^{12s}$, $R^{13s}$, and/or $R^{14s}$ of any heteroatomic ligand structure depicted herein and/or any heteroatomic ligand chromium compound complex depicted herein having an $R^{1s}$, $R^{2s}$, $R^{11s}$, $R^{12s}$, $R^{13s}$, and/or $R^{14s}$ group independently can an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, each $R^{1s}$, $R^{2s}$, $R^{11s}$, $R^{12s}$, $R^{13s}$, and/or $R^{14s}$ of any heteroatomic ligand structure depicted herein and/or any heteroatomic ligand chromium compound complex depicted herein having an $R^{1s}$, $R^{2s}$, $R^{11s}$, $R^{12s}$, $R^{13s}$, and/or $R^{14s}$ group independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect disclosed herein, each $R^{1s}$, $R^{2s}$, $R^{11s}$, $R^{12s}$, $R^{13s}$, and/or $R^{14s}$ alkyl group independently can be a $C_1$ to $C_{20}$, a $C_1$ to $C_{10}$, or a $C_1$ to $C_5$ alkyl group. In any aspect disclosed herein, each $R^{1s}$, $R^{2s}$, $R^{11s}$, $R^{12s}$, $R^{13s}$, and/or $R^{14s}$ substituted alkyl group independently can be a $C_1$ to $C_{20}$, a $C_1$ to $C_{10}$, or a $C_1$ to $C_5$ substituted alkyl group. In any aspect disclosed herein, each $R^{1s}$, $R^{2s}$, $R^{11s}$, $R^{12s}$, $R^{13s}$, and/or $R^{14s}$ cycloalkyl group independently can be a $C_4$ to $C_{20}$, a $C_4$ to $C_{15}$, or a $C_4$ to $C_{10}$ cycloalkyl group. In any aspect disclosed herein, each $R^{1s}$, $R^{2s}$, $R^{11s}$, $R^{12s}$, $R^{1s3}$, and/or $R^{14s}$ substituted cycloalkyl group independently can be a $C_4$ to $C_{20}$, a $C_4$ to $C_{15}$, or a $C_4$ to $C_{10}$ substituted cycloalkyl group. In any aspect disclosed herein, each $R^{1s}$, $R^{2s}$, $R^{11s}$, $R^{12s}$, $R^{13s}$, and/or $R^{14s}$ aryl group independently can be a $C_6$ to $C_{20}$, a $C_6$ to $C_{15}$, or a $C_6$ to $C_{10}$ aryl group. In any aspect disclosed herein, each $R^{1s}$, $R^{2s}$, $R^{11s}$, $R^{12s}$, $R^{13s}$, and/or $R^{14s}$ substituted aryl group independently can be a $C_6$ to $C_{20}$, a $C_6$ to $C_{15}$, or a $C_6$ to $C_{10}$ substituted aryl group. In any aspect disclosed herein, each $R^{1s}$, $R^{2s}$, $R^{11s}$, $R^{12s}$, $R^{13s}$, and/or $R^{14s}$ aralkyl group independently can be a $C_7$ to $C_{20}$, a $C_7$ to $C_{15}$, or a $C_7$ to $C_{10}$ aralkyl group. In any aspect disclosed herein, each $R^{1s}$, $R^{2s}$, $R^{11s}$, $R^{12s}$, $R^{13s}$, and/or $R^{14s}$ substituted aralkyl group independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarboxy groups, and substituent hydrocarboxy groups can be utilized without limitation to further describe a substituted group (general or specific) which can be utilized $R^{1s}$, $R^{2s}$, $R^{11s}$, $R^{12s}$, $R^{13s}$, and/or $R^{14s}$.

In an aspect, each $R^{1s}$, $R^{2s}$, $R^{11s}$, $R^{12s}$, $R^{13s}$, and/or $R^{14s}$ independently can be a methyl group, an ethyl group, a propyl group, a butyl group, a pentyl group, a hexyl group, a heptyl group, or an octyl group; or alternatively, a methyl group, an ethyl group, an iso-propyl (2-propyl) group, a tert-butyl (2-methyl-2-propyl) group, or a neopentyl (2,2-dimethyl-1-propyl) group. In some aspects, the alkyl groups which can be utilized as each $R^{1s}$, $R^{2s}$, $R^{11s}$, $R^{12s}$, $R^{13s}$, and/or $R^{14s}$ independently can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^{1s}$, $R^{2s}$, $R^{11s}$, $R^{12s}$, $R^{13s}$, and/or $R^{14s}$.

In an aspect, each $R^{1s}$, $R^{2s}$, $R^{11s}$, $R^{12s}$, $R^{13s}$, and/or $R^{14s}$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an aspect, the substituted cycloalkyl group, which can be utilized for any of $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^{1s}$, $R^{2s}$, $R^{11s}$, $R^{12s}$, $R^{13s}$, and/or $R^{14s}$ can be the same or different; alternatively, all the substituents of a multi-substituted cycloalkyl group can be the same; or alternatively, all the substituents of a multi-substituted cycloalkyl group can be different. Each substituent of a substituted cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^{1s}$, $R^{2s}$, $R^{11s}$, $R^{12s}$, $R^{13s}$, and/or $R^{14s}$.

In a non-limiting aspect, each $R^{1s}$, $R^{2s}$, $R^{11s}$, $R^{12s}$, $R^{13s}$, and/or $R^{14s}$ independently can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{1s}$, $R^{2s}$, $R^{11s}$, $R^{12s}$, $R^{13s}$, and/or $R^{14}$. Generally, the alkyl substituents of a disubstituted cyclohexyl or cyclopentyl group can be the same, or alternatively, the alkyl substituents can be different. In some non-limiting aspects, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, each $R^{1s}$, $R^{2s}$, $R^{11s}$, $R^{12s}$, $R^{13s}$, and/or $R^{14s}$ independently can be a phenyl group or a substituted phenyl group; alternatively, a phenyl group; or alternatively, a substituted phenyl group. In an aspect, the substituted phenyl group which can be utilized for each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an aspect, one or more substituents of a multi-substituted phenyl group utilized as $R^{1s}$, $R^{2s}$, $R^{11s}$, $R^{12s}$, $R^{13s}$, and/or $R^{14s}$ can be the same or different; alternatively, all the substituents can be the same; or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy group can be utilized without limitation to further describe a substituted phenyl group (general or specific) which can be utilized as $R^{1s}$, $R^{2s}$, $R^{11s}$, $R^{12s}$, $R^{13s}$, and/or $R^{14s}$.

In a non-limiting aspect, each $R^{1s}$, $R^{2s}$, $R^{11s}$, $R^{12s}$, $R^{13s}$, and/or $R^{14s}$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{1s}$, $R^{2s}$, $R^{11s}$, $R^{12s}$, $R^{13s}$, and/or $R^{14s}$. Generally, the alkyl substituents of dialkylphenyl groups (general or specific) or trialkylphenyl groups (general or specific) can be the same, or alternatively, the alkyl substituents can be different. In some non-limiting aspects, each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; or alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, each $R^{1s}$, $R^{2s}$, $R^{11s}$, $R^{12s}$, $R^{13s}$, and/or $R^{14s}$ independently can be a phenyl group, a 2-alkoxyphenyl group, or a 4-alkoxyphenyl group. In some non-limiting aspects, each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In a non-limiting aspect, each $R^{1s}$, $R^{2s}$, $R^{11s}$, $R^{12s}$, $R^{13s}$, and/or $R^{14s}$ independently can be a phenyl group, a 2-halophenyl group, a 4-halophenyl group, or a 2,6-dihalophenylgroup. Generally, the halides of a dihalophenyl group can be the same, or alternatively, the halides can be different. In some aspects, each $R^{1s}$, $R^{2s}$, $R^{11s}$, $R^{12s}$, $R^{13s}$, and/or $R^{14s}$ independently can be a phenyl group, a 2-fluorophenyl group, a 4-fluorophenyl group, or a 2,6-difluorophenyl group.

In an aspect, each $R^{1s}$, $R^{2s}$, $R^{11s}$, $R^{12s}$, $R^{13s}$, and/or $R^{14s}$ independently can be a benzyl group or a substituted benzyl group; alternatively, a benzyl group; or alternatively, a substituted benzyl group. Each substituent of a substituted benzyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^{1s}$, $R^{2s}$, $R^{11s}$, $R^{12s}$, $R^{13s}$, and/or $R^{14s}$.

In further aspects, two $R^{1s}$s attached to a single $X^{1s}$, two $R^{2s}$s attached to a single $X^{2s}$, $R^{11s}$ and $R^{12s}$, and/or $R^{13s}$ and $R^{14s}$ independently can be joined to form a ring or a ring system containing the heteroatom to which they are attached. The joining of two $R^{1s}$s attached to a single $X^{1s}$, can be designated $L^{11s}$. The joining of two $R^{2s}$s attached to a single $X^{2s}$, can be designated $L^{22s}$. The joining of $R^{11s}$ and $R^{12s}$ can be designated $L^{12s}$. The joining of $R^{13s}$ and $R^{14s}$ can be designated $L^{34}$. In an aspect, $L^{11s}$, $L^{22s}$, $L^{12s}$, and/or $L^{34s}$ independently can be an organylene group; alternatively, an organylene group consisting of inert functional groups; alternatively, a hydrocarbylene group; or alternatively, an alkylene group. In an aspect, the $L^{11s}$, $L^{22s}$, $L^{12s}$, and/or $L^{34s}$ organylene group, when present, independently can be a $C_4$ to $C_{30}$, a $C_4$ to $C_{20}$, a $C_4$ to $C_{15}$, or a $C_4$ to $C_{10}$ organylene group. In some aspects, the $L^{11s}$, $L^{22s}$, $L^{12s}$, and/or $L^{34s}$ organylene group consisting of inert functional groups, when present, independently can be a $C_4$ to $C_{30}$, a $C_4$ to $C_{20}$, a $C_4$ to $C_{15}$, or a $C_4$ to $C_{10}$ organylene group consisting of inert functional groups. In other aspects, the $L^{11s}$, $L^{22s}$, $L^{12s}$, and/or $L^{34s}$ hydrocarbyl group, when present, independently can be a $C_4$ to $C_{30}$, a $C_4$ to $C_{20}$, a $C_4$ to $C_{15}$, or a $C_4$ to $C_{10}$ hydrocarbylene group. In a further aspect, the $L^{11s}$, $L^{22s}$, $L^{12s}$, and/or $L^{34s}$ alkylene group, when present, independently can be a $C_4$ to $C_{30}$, a $C_4$ to $C_{20}$, a $C_4$ to $C_{15}$, or a $C_4$ to $C_{10}$ alkylene group. In an aspect, $L^{12s}$ and/or $L^{34s}$, when present, independently can be a can be but-1,4-ylene group, a 1,4-diphenylbut-1,4-ylene group, a 1,4-di(2-methylphenyl)but-1,4-ylene group, 1,4-di(4-methylphenyl)but-1,4-ylene group, 1,4-di(4-t-butylphenyl)but-1,4-ylene group, a 1,4-di(3,5-dimethylphenyl)but-1,4-ylene group, a pent-1,4-ylene group, a 1-phenylpenta-1,4-ylene group, a 4-phenylpenta-1,4-ylene group, a hex-2,5-ylene group, a 2,2'-biphenylene group, a 2,2'-(methandiyl)diphenylene group, or a 2,2'-(1,2-ethandiyl)diphenylene group.

Generally, $R^{5s}$, of any heteroatomic ligand structure depicted herein and any heteroatomic ligand chromium compound complex depicted herein having an $R^{5s}$ group, can be an organyl group; alternatively, an organyl group consisting of inert functional groups; or alternatively, a hydrocarbyl group. In an aspect, the $R^{5s}$ organyl group can be a $C_1$ to $C_{20}$, a $C_1$ to $C_{15}$, a $C_1$ to $C_{10}$, or a $C_1$ to $C_5$ organyl group. In an aspect, the $R^{5s}$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^{5s}$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^{5s}$, of any heteroatomic ligand structure depicted herein and any heteroatomic ligand chromium compound complex depicted herein having an $R^{5s}$ group, can be an alkyl group, a substituted alkyl group, a cycloalkyl group, a substituted cycloalkyl group, an aryl group, a substituted aryl group, an aralkyl group, or a substituted aralkyl group; can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^{5s}$ of any heteroatomic ligand structure depicted herein and any heteroatomic ligand chromium compound complex depicted herein having an $R^{5s}$ group, can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^{5s}$ alkyl group can be a $C_1$ to $C_{20}$, a $C_1$ to $C_{15}$, or a $C_1$ to $C_{10}$ alkyl group. In any aspect disclosed herein, the $R^{5s}$ substituted alkyl group can be a $C_1$ to $C_{20}$, a $C_1$ to $C_{15}$, or a $C_1$ to $C_{10}$ substituted alkyl group. In any aspect disclosed herein, the $R^{5s}$ cycloalkyl group can be a $C_4$ to $C_{20}$, a $C_4$ to $C_{15}$, or a $C_4$ to $C_{10}$ cycloalkyl group. In any aspect disclosed herein, the $R^{5s}$ substituted cycloalkyl group can be a $C_4$ to $C_{20}$, a $C_4$ to, or a $C_4$ to $C_{10}$ substituted cycloalkyl group. In any aspect disclosed herein, the $R^{5s}$ aryl group can be a $C_6$ to $C_{20}$, a $C_6$ to $C_{15}$, or a $C_6$ to $C_{10}$ aryl group. In any aspect disclosed herein, the $R^{5s}$ substituted aryl group can be a $C_6$ to $C_{20}$, a $C_6$ to $C_{15}$, or a $C_6$ to $C_{10}$ substituted aryl group. In any aspect disclosed herein, the $R^{5s}$ aralkyl group can be a $C_7$ to $C_{20}$, a $C_7$ to $C_{15}$, or a $C_7$ to $C_{10}$ aralkyl group. In any aspect disclosed herein, the $R^{5s}$ substituted aralkyl group can be a $C_7$ to $C_{20}$, a $C_7$ to $C_{15}$, or a $C_7$ to $C_{10}$ substituted aralkyl group. Each substituent of a substituted alkyl group (general or specific), substituted cycloalkyl group (general or specific), substituted aryl group (general or specific), and/or substituted aralkyl group (general or specific) can be a halogen, hydrocarbyl group, or a hydrocarboxy group; alternatively, a halogen or a hydrocarbyl group; alternatively, a halogen or a hydrocarboxyl group; alternatively, a hydrocarbyl group or a hydrocarboxy group; alternatively, a halogen; alternatively, a hydrocarbyl group; or alternatively, a hydrocarboxy group. Substituent halogens, hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted group (general or specific) which can be utilized $R^{5s}$.

In an aspect, $R^{5s}$ can be a methyl group, an ethyl group, a propyl group, a butyl group, a pentyl group, a hexyl group, a heptyl group, or an octyl group; alternatively, a methyl group, an ethyl group, an n-propyl (1-propyl) group, an isopropyl (2-propyl) group, an n-butyl (1-butyl) group, a sec-butyl (2-butyl) group, an isobutyl (2-methyl-1-propyl) group, a tert-butyl (2-methyl-2-propyl) group, an n-pentyl (1-pentyl) group, a 2-pentyl group, a 3-pentyl group, a 2-methyl-1-butyl group, a tert-pentyl (2-methyl-2-butyl) group, a 3-methyl-1-butyl group, a 3-methyl-2-butyl group, or a neo-pentyl (2,2-dimethyl-1-propyl) group; alternatively, a methyl group, an ethyl group, an iso-propyl (2-propyl) group, a tert-butyl (2-methyl-2-propyl) group, or a neopentyl (2,2-dimethyl-1-propyl) group. In some aspects, the $R^{5s}$ alkyl groups can be substituted. Each substituent of a $R^{5s}$ substituted alkyl group independently can be a halogen or a hydrocarboxy group; alternatively, a halogen; or alternatively, a hydrocarboxy group. Substituent halogens and substituent hydrocarboxy groups (general and specific) are independently described herein and these substituent groups can be utilized without limitation to further describe a substituted alkyl group (general or specific) which can be utilized as $R^{5s}$.

In an aspect, $R^{5s}$ can be a cyclopentyl group, a substituted cyclopentyl group, a cyclohexyl group, a substituted cyclohexyl group; alternatively, a cyclopentyl group or a substituted cyclopentyl group; or alternatively, a cyclohexyl group or a substituted cyclohexyl group. In further aspects, $R^{5s}$ can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^{5s}$ can be the same or different; alternatively, all the substituents of a multi-substituted cycloalkyl group can be the same; or alternatively, all the substituents of a multi-substituted cycloalkyl group can be different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted cycloalkyl group (general or specific) which can be utilized as $R^{5s}$.

In a non-limiting aspect, $R^{5s}$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{5s}$. Generally, the alkyl substituents of a disubstituted cyclohexyl or cyclopentyl group can be the same, or alternatively, the alkyl substituents can be different. In some non-limiting aspects, $R^{5s}$ heteroatomic ligand structure provided herein, and/or any heteroatomic ligand chromium compound complex structure provided herein can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^{5s}$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group. In an aspect, $R^{5s}$ heteroatomic ligand structure provided herein, and/or any heteroatomic ligand chromium compound complex structure provided herein can be a cyclopentyl group, a 2-methylcyclopentyl group, a cyclohexyl group, or a 2-methylcyclohexyl group; alternatively, a cyclopentyl group or a cyclohexyl group; or alternatively, a 2-methylcyclopentyl group or a 2-methylcyclohexyl group.

In an aspect, $R^{5s}$ can be a phenyl group or a substituted phenyl group; alternatively, a phenyl group; or alternatively, a substituted phenyl group. In some aspects, $R^{5s}$ can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group or a 4-substituted phenyl group;

alternatively, a 2,4-disubstituted phenyl group, a 2,6-disubstituted phenyl group, or a 2,4,6-trisubstituted phenyl group; alternatively, a 2,4-disubstituted phenyl group or a 2,6-disubstituted phenyl group; alternatively, a 2-substituted phenyl group; alternatively, a 4-substituted phenyl group; or alternatively, a 2,4-disubstituted phenyl group; alternatively, a 2,6-disubstituted phenyl group; or alternatively, a 2,4,6-trisubstituted phenyl group. In an aspect, one or more substituents of a multi-substituted phenyl group utilized as $R^{5s}$ can be the same or different; alternatively, all the substituents can be the same, or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted phenyl group (general or specific) which can be utilized as $R^{5s}$.

In a non-limiting aspect, $R^{5s}$ can be a phenyl group, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group, a 2,4-dialkylphenyl group, a 2,6-dialkylphenyl group, or a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{5S}$. Generally, the alkyl substituents of dialkylphenyl groups (general of specific) or trialkylphenyl groups (general or specific) can be the same, or alternatively, the alkyl substituents can be different. In some non-limiting aspects, $R^{5s}$ can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2,6-dimethylphenyl group, or a 2,4,6-trimethylphenyl group.

Generally, $L^{2s}$, of any heteroatomic ligand and/or any heteroatomic ligand chromium compound complex having an $L^{2s}$ group, can be an organylene group; alternatively, an organylene group consisting of inert functional groups; alternatively, a hydrocarbylene group; or alternatively, an alkylene group. In an aspect, the $L^{2s}$ organylene group can be a $C_1$ to $C_{20}$, a $C_1$ to $C_{15}$, or a $C_1$ to $C_{10}$ organylene group. In an aspect, the $L^{2s}$ organylene group consisting of inert functional groups can be a $C_1$ to $C_{20}$, a $C_1$ to $C_{15}$, or a $C_1$ to $C_{10}$ organylene group consisting of inert functional groups. In an aspect, the $L^{2s}$ alkylene group can be a $C_1$ to $C_{20}$, $C_1$ to $C_{15}$, or a $C_1$ to $C_{10}$ alkylene group.

In an aspect, $L^{2s}$ of any heteroatomic ligand and/or any heteroatomic ligand chromium compound complex having an $L^{2s}$ group can be —$(CR^{P}R^{P'})_m$— where each $R^{P}$ and $R^{P'}$ can independently be hydrogen, methyl, ethyl, propyl, isopropyl, or butyl groups and m can be an integer from 1 to 12.

In some aspects, $L^{2s}$ of any heteroatomic ligand and/or any heteroatomic ligand chromium compound complex having an $L^{2s}$ group can be a methylene group (—$CH_2$—), an ethyl-1,2-ene group (—$CH_2CH_2$—), a propyl-1,3-ene group (—$CH_2CH_2CH_2$—), a prop-1,2-ylene group (—$CH(CH_3)CH_2$—), a prop-2,2-ylene group (—$C(CH_3)_2$—), a butyl-1,4-ene group (—$CH_2CH_2CH_2CH_2$—), or a 2-methylprop-1,3-ylene group (—$CH_2CH(CH_3)$—$CH_2$—); or alternatively a methylene group (—$CH_2$—), an ethyl-1,2-ene group (—$CH_2CH_2$—), or a prop-1,2-ylene group (—$CH(CH_3)CH_2$—).

In an aspect, $L^{2s}$ of any heteroatomic ligand and/or any heteroatomic ligand chromium compound complex having an $L^{2s}$ group, can be 1,2-cyclohexylene, a substituted 1,2-cyclohexylene, 1,3-cyclohexylene, a substituted 1,3-cyclohexylene, 1,4-cyclohexylene, a substituted 1,4-cyclohexylene, 3,3'-bicyclohexylene, a substituted 3,3'-bicyclohexylene, 4,4'-bicyclohexylene, a substituted 4,4'-bicyclohexylene, bis(3-cyclohexylene)methane, a substituted bis(3-cyclohexylene)methane, bis(4-cyclohexylene)methane, a substituted bis(4-cyclohexylene)methane, 1,2-bis(3-cyclohexylene)ethane, a substituted 1,2-bis(3-cyclohexylene)ethane, 1,2-bis(4-cyclohexylene)ethane, a substituted 1,2-bis(4-cyclohexylene)ethane, 1,2-bis(3-cyclohexylene)-propane, a substituted 1,2-bis(3-cyclohexylene)propane, 1,2-bis(4-cyclohexylene)propane, a substituted 1,2-bis(4-cyclohexylene)propane, 2,2-bis(3-cyclohexylene)propane, a substituted 2,2-bis(3-cyclohexylene)propane, 2,2-bis(4-cyclohexylene)propane, or a substituted 2,2-bis(4-cyclohexylene)propane. In some aspects, $L^{2s}$ of any heteroatomic ligand and/or any heteroatomic ligand chromium compound complex having an $L^{2s}$ group can be a substituted 1,2-cyclohexylene, a substituted 1,3-cyclohexylene, a substituted 1,4-cyclohexylene, a substituted 3,3'-bicyclohexylene, a substituted 4,4'-bicyclohexylene, a substituted bis(3-cyclohexylene)methane, a substituted bis(4-cyclohexylene)methane, a substituted 1,2-bis(3-cyclohexylene)ethane, a substituted 1,2-bis(4-cyclohexylene)ethane, a substituted 1,2-bis(3-cyclohexylene)propane, a substituted 1,2-bis(4-cyclohexylene)propane, a substituted 2,2-bis(3-cyclohexylene)propane, or a substituted 2,2-bis(4-cyclohexylene)propane. In an aspect, each substituent of a substituted cyclohexylene, a substituted bis(cyclohexylene)methane, a substituted bis(cyclohexylene)ethane, or a substituted 1,2-bis(3-cyclohexylene)propane which can be utilized as $L^{2s}$ can be a hydrocarbyl group. Substituent groups (general and specific) are independently disclosed herein and can be utilized without limitation to further describe a substituted cyclohexylene (general or specific), a substituted bis(cyclohexylene)methane (general or specific), a substituted bis(cyclohexylene)ethane (general or specific), or a substituted 1,2-bis(3-cyclohexylene)propane (general or specific) which can be utilized as $L^{2s}$.

In an aspect, $L^{2s}$ of any heteroatomic ligand and/or any heteroatomic ligand chromium compound complex having an $L^{2s}$ group can be 1,2-phenylene, a substituted 1,2-phenylene, 1,3-phenylene, a substituted 1,3-phenylene, 1,4-phenylene, a substituted 1,4-phenylene, 3,3'-biphenylene, a substituted 3,3'-biphenylene, 4,4'-biphenylene, a substituted 4,4'-biphenylene, bis(3-phenylene)methane, a substituted bis(3-phenylene)methane, bis(4-phenylene)methane, a substituted bis(4-phenylene)methane, 1,2-bis(3-phenylene)ethane, a substituted 1,2-bis(3-phenylene)ethane, 1,2-bis(4-phenylene)ethane, a substituted 1,2-bis(4-phenylene)ethane, 1,2-bis(3-phenylene)propane, a substituted 1,2-bis(3-phenylene)propane, 1,2-bis(4-phenylene)propane, a substituted 1,2-bis(4-phenylene)propane, 2,2-bis(3-phenylene)propane, a substituted 2,2-bis(3-phenylene)propane, 2,2-bis(4-phenylene)propane, or a substituted 2,2-bis(4-phenylene)propane. In some aspects, $L^{2s}$ of any heteroatomic ligand and/or any heteroatomic ligand chromium compound complex having an $L^{2s}$ group can be a substituted 1,2-phenylene, a substituted 1,3-phenylene, a substituted 1,4-phenylene, a substituted 3,3'-biphenylene, a substituted 4,4'-biphenylene, a substituted bis(3-phenylene)methane, a substituted bis(4-phenylene)methane, a substituted 1,2-bis(3-phenylene)ethane, a substituted 1,2-bis(4-phenylene)ethane, a substituted 1,2-bis(3-phenylene)propane, a substituted 1,2-bis(4-phenylene)propane, a substituted 2,2-bis(3-phenylene)propane, or a substituted 2,2-bis(4-phenylene)propane. In an aspect, each substituent of a substituted phenylene (general or specific), a substituted biphenylene (general or specific), a substituted bis(phenylene)methane (general or specific), a substituted bis(phenylene)ethane (general or specific), and/or a substituted bis(phenylene)propane (general or specific) which can be utilized as $L^{2s}$ can be a hydrocarbyl group. Substituent hydrocarbyl groups (general and specific) are independently disclosed herein and can be utilized without limitation to further describe a substituted phenylene (general or specific), a substituted biphenylene (general or specific), a substituted bis(phenylene)methane (general or specific), a substituted bis(phenylene)ethane (general or specific), and/or a substituted bis(phenylene)propane (general or specific) which can be utilized as $L^{2s}$.

Generally, $L^{3s}$ and/or $L^{4s}$, of any heteroatomic ligand and/or any heteroatomic ligand chromium compound complex having an $L^{3s}$ and/or $L^{4s}$ group, independently can be an organylene group; alternatively, an organylene group consisting of inert functional groups; alternatively, a hydrocarbylene group; alternatively, an alkylene group. In an aspect, the $L^{3s}$ and/or $L^{4s}$ organylene group independently can be a $C_1$ to $C_{20}$, a $C_1$ to $C_{15}$, or a $C_1$ to $C_{10}$ organylene group. In an aspect, the $L^{3s}$ and/or $L^{4s}$ organylene group consisting of inert functional groups independently can be a $C_1$ to $C_{20}$, a $C_1$ to $C_{15}$, or a $C_1$ to $C_{10}$ organylene group consisting of inert functional groups. In an aspect, the $L^{3s}$ and/or $L^{4s}$ hydrocarbylene group independently can be a $C_1$ to $C_{20}$, a $C_1$ to $C_{15}$, or a $C_1$ to $C_{10}$ hydrocarbylene group. In an aspect, the $L^{3s}$ and/or $L^{4s}$ alkylene group independently can be a $C_1$ to $C_{20}$, $C_1$ to $C_{15}$, or a $C_1$ to $C_{10}$ alkylene group.

In an aspect, $L^{3s}$ and/or $L^{4s}$ of any heteroatomic ligand structure and/or any heteroatomic ligand chromium compound complex having an $L^{3s}$ and/or $L^{4s}$ group independently can be —$(CR^P R^{P'})_m$— where each $R^P$ and $R^{P'}$ can independently be hydrogen, methyl, ethyl, propyl, isopropyl, or butyl groups and m can be an integer from 1 to 12. In some aspects, $L^{3s}$ and/or $L^{4s}$ of any heteroatomic ligand structure and/or any heteroatomic ligand chromium compound complex having an $L^{3s}$ and/or $L^{4s}$ group independently can be a methylene group (—$CH_2$—), an eth-1,2-ylene group (—$CH_2CH_2$—), an ethen-1,2-ylene group (—CH=CH—), a prop-1,3-ylene group (—$CH_2CH_2CH_2$—), a prop-1,2-ylene group (—$CH(CH_3)CH_2$—), a prop-2,2-ylene group (—$C(CH_3)_2$—), a 1-methylethen-1,2-ylene group (—$C(CH_3)$=CH—), a but-1,4-ylene group (—$CH_2CH_2CH_2$—$CH_2$—), a but-1,3-ylene group (—$CH_2CH_2CH(CH_3)$—), a but-2,3-ylene group (—$CH(CH_3)CH(CH_3)$—), a but-2-en-2,3-ylene group (—$C(CH_3)$=$C(CH_3)$—), a 3-methylbut-1,3-ylene group (—$CH_2CH_2C(CH_3)_2$—), a 1,2-cyclopentylene group, a 1,2-cyclohexylene group, or a phen-1,2-ylene group; alternatively, a methylene group (—$CH_2$—), an eth-1,2-ylene group (—$CH_2CH_2$—), a prop-1,3-ylene group (—$CH_2CH_2CH_2$—), a prop-1,2-ylene group (—$CH(CH_3)CH_2$—), a prop-2,2-ylene group (—$C(CH_3)_2$—), a but-1,4-ylene group (—$CH_2CH_2CH_2$—$CH_2$—), a but-1,3-ylene group (—$CH_2CH_2CH(CH_3)$—), a but-2,3-ylene group (—$CH(CH_3)CH(CH_3)$—), a 1,2-cyclopentylene group, a 1,2-cyclohexylene group, or a phen-1,2-ylene group; or alternatively, an eth-1,2-ylene group (—$CH_2CH_2$—), a prop-1,3-ylene group (—$CH_2CH_2CH_2$—), a prop-1,2-ylene group (—$CH(CH_3)CH_2$—), a but-1,3-ylene group (—$CH_2CH_2CH(CH_3)$—), a but-2,3-ylene group (—$CH(CH_3)CH(CH_3)$—), a 1,2-cyclopentylene group, a 1,2-cyclohexylene group, or a phen-1,2-ylene group.

Various aspects described herein refer to non-hydrogen substituents such as halogen (or halo, halide), hydrocarbyl, hydrocarboxy, alkyl, and/or alkoxy substituents. In an embodiment, each non-hydrogen substituent of any aspect calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Each hydrocarbyl substituent independently can be a $C_1$ to $C_{10}$ hydrocarbyl group; or alternatively, a $C_1$ to $C_5$ hydrocarbyl group. Each hydrocarboxy substituent independently can be a $C_1$ to $C_{10}$ hydrocarboxy group; or alternatively, a $C_1$ to $C_5$ hydrocarboxy group. Each halide substituent independently can be a fluoride, chloride, bromide, or iodide; alternatively, a fluoride or chloride; alternatively, a fluoride; alternatively, a chloride; alternatively, a bromide; or alternatively, an iodide.

In an aspect, any hydrocarbyl substituent independently can be an alkyl group, an aryl group, or an aralkyl group; alternatively, an alkyl group; alternatively, an aryl group; or alternatively, an aralkyl group. In an aspect, any alkyl substituent independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an aspect, any aryl substituent independently can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an aspect, any aralkyl substituent independently can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an aspect, any hydrocarboxy substituent independently can be an alkoxy group, an aryloxy group, or an aralkoxy group; alternatively, an alkoxy group; alternatively, an aryloxy group, or an aralkoxy group. In an aspect, any alkoxy substituent independently can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an aspect, any aryloxy substituent independently can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an aspect, any aralkoxy substituent independently can be benzoxy group.

Generally, the chromium compound or the chromium compound of the heteroatomic ligand chromium compound complexes described herein can have formula $CrX_p$ where X represents a monoanionic ligand, and p represents the number of monoanionic ligands (and the oxidation state of the chromium in the chromium compound. The monoanionic ligand (X), and p are independent elements of the chromium compound or the chromium compound of the heteroatomic ligand chromium compound complexes described herein and are independently described herein. The independent descriptions of the monoanionic ligand (X), and p can be utilized without limitation, and in any combination, to further describe the chromium compound or the chromium compound of the heteroatomic ligand chromium compound complexes described herein.

Generally, the chromium atom of the chromium compound ($CrX_p$) can have any positive oxidation state available to a chromium atom. In an aspect, the chromium atom can have an oxidation state of from +2 to +6; alternatively, from +2 to +4; or alternatively, from +2 to +3. In some aspects, the chromium atom of the chromium compound ($CrX_p$) can have an oxidation state of +1; alternatively, +2; alternatively, +3; or alternatively, +4.

The monoanion (X) of the chromium compound can be any monoanion. In an aspect, the monoanion (X) can be a halide, a carboxylate, a β-diketonate, a hydrocarboxide, a nitrate, or a chlorate. In some aspects, the monoanion (X) can be a halide, a carboxylate, a β-diketonate, or a hydrocarboxide. In any aspect, the hydrocarboxide can be an alkoxide, an aryloxide, or an aralkoxide. Generally, hydrocarboxide (and subdivisions of hydrocarboxide) are the anion analogues of the hydrocarboxy group. In other aspects, the monoanion (X) can be a halide, a carboxylate, a β-diketonate, or an alkoxide; or alternatively, a halide or a β-diketonate. In other aspects, the monoanion (X) can be a halide; alternatively, a carboxylate; alternatively, a β-diketonate; alternatively, a hydrocarboxide; alternatively, an alkoxide; or alternatively, an aryloxide. Generally, when the heteroatomic ligand of the heteroatomic ligand chromium compound complex is a neutral heteroatomic ligand, the number of monoanions (p) can equal the oxidation state of the chromium atom. When the heteroatomic ligand of the heteroatomic ligand chromium compound complex is an anionic heteroatomic ligand, the number of monoanions (p) can equal one less than the oxidation state of the chromium atom. In an aspect, the number of monoanions can be from 2 to 6; alternatively, from 2 to 4; alternatively, from 2 to 3; alternatively, 1; alternatively, 2; alternatively, 3; or alternatively, 4.

Generally, each halide of the chromium compound independently can be fluorine, chlorine, bromine, or iodine; or alternatively, chlorine, bromine, or iodine. In an aspect, each halide monoanion of the chromium compound can be chlorine; alternatively, bromine; or alternatively, iodine.

Generally, each carboxylate of the chromium compound independently can be a $C_1$ to $C_{20}$ carboxylate; or alternatively, a $C_1$ to $C_{10}$ carboxylate. In an aspect, each carboxylate of the chromium compound independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some aspects, each carboxylate of the chromium compound independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some aspects, the carboxylate of the chromium compound can be triflate (trifluoroacetate).

Generally, each β-diketonate of the chromium compound independently can be any $C_1$ to $C_{20}$ a β-diketonate; or alternatively, any $C_1$ to $C_{10}$ β-diketonate. In an aspect, each β-diketonate of the chromium compound independently can be acetylacetonate (i.e., 2,4-pentanedionate), hexafluoroacetylacetonate (i.e., 1,1,1,5,5,5-hexafluoro-2,4-pentanedionate), or benzoylacetonate); alternatively, acetylacetonate; alternatively, hexafluoroacetylacetonate; or alternatively, benzoylacetonate.

Generally, each hydrocarboxide of the chromium compound independently can be any $C_1$ to $C_{20}$ hydrocarboxide; or alternatively, any $C_1$ to $C_{10}$ hydrocarboxide. In an aspect, each hydrocarboxide of the chromium compound independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an aspect, each alkoxide of the chromium compound independently can be methoxide, ethoxide, a propoxide, or a butoxide; alternatively, methoxide, ethoxide, isopropoxide, or tert-butoxide; alternatively, methoxide; alternatively, an ethoxide; alternatively, an isopropoxide; or alternatively, a tert-butoxide. In an aspect, the aryloxide can be phenoxide.

In some non-limiting aspects, the chromium compound and/or the chromium compound of the heteroatomic ligand chromium compound complex can comprise, can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting aspects, the chromium compound and/or the chromium compound of the heteroatomic ligand chromium compound complex can comprise, can consist essentially of, or consist of, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate. Halides, carboxylates, β-diketonates are independently described herein and these halides, carboxylates, β-diketonate and these independently described halides, carboxylates, β-diketonates can be utilized without limitation and in any combination to further described the chromium compound and/or the chromium compound of the heteroatomic ligand chromium compound complex. In further non-limiting aspects, the chromium compound and/or the chromium compound of the heteroatomic ligand chromium compound complex can comprise, can consist essentially of, or consist of, chromium(II) chloride, chromium(III) chloride, chromium(II) fluoride, chromium(III) fluoride, chromium(II) bromide, chromium(III) bromide, chromium (II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium(II) hexafluoracetylacetonate, chromium(III) hexafluoracetylacetonate, chromium(III) benzoylacetonate, or chromium(III) benzoylacetonate; alternatively, chromium(III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate; alternatively, chromium(III) chloride, or chromium(III) acetylacetonate; alternatively, chromium(III) chloride; or alternatively, chromium(III) acetylacetonate.

In a non-limiting aspect, the heteroatomic ligand chromium compound complex can be selected from any one or more of a heteroatomic ligand chromium compound complex having i) Structure NPFCr1 where $R^1$ is 2,6-dimethylphenyl, $R^3$ is H, $R^4$ and $R^5$ are isopropyl, and X is chlorine; $R^1$ is 2,6-dimethylphenyl, $R^3$ is H, $R^4$ and $R^5$ are phenyl, and X is chlorine; $R^1$ is 2,6-dimethylphenyl, $R^3$ is H, $R^4$ and $R^5$ are 4-methoxyphenyl, and X is chlorine; $R^1$ is 2,4,6-trimethylphenyl, $R^3$ is H, $R^4$ and $R^5$ are isopropyl, and X is chlorine; $R^1$ is 2,4,6-trimethylphenyl, $R^3$ is H, $R^4$ and $R^5$ are phenyl, and X is chlorine; and $R^1$ is 2,4,6-trimethylphenyl, $R^3$ is H, $R^4$ and $R^5$ are 4-methoxyphenyl, and X is chlorine: ii) Structure NPACr1 where $R^1$ is 2,6-dimethylphenyl, $R^2$ is phenyl, $R^3$ is H, $R^4$ and $R^5$ are isopropyl, and X is chlorine; $R^1$ is 2,4,6-trimethylphenyl, $R^2$ is phenyl, $R^3$ is H, $R^4$ and $R^5$ are isopropyl, and X is chlorine; $R^1$ is 2,6-dimethylphenyl, $R^2$ is phenyl, $R^3$ is H, $R^4$ and $R^5$ are phenyl, and X is chlorine; $R^1$ is 2,4,6-trimethylphenyl, $R^2$ is phenyl, $R^3$ is H, $R^4$ and $R^5$ are phenyl, and X is chlorine; $R^1$ is 2,6-dimethylphenyl, $R^2$ is 4-methylbenzyl, $R^3$ is H, $R^4$ and $R^5$ are phenyl, and X is chlorine; $R^1$ is 2,6-dimethylphenyl, $R^2$ is phenyl, $R^3$ is H, $R^4$ and $R^5$ are 4-methoxyphenyl, and X is chlorine; $R^1$ is 2,6-dimethylphenyl, $R^2$ is 4-t-butylphenyl, $R^3$ is H, $R^4$ and $R^5$ are methyl, and X is chlorine; $R^1$ is 2,4,6-trimethylphenyl, $R^2$ is 4-t-butylphenyl, $R^3$ is H, $R^4$ and $R^5$ are methyl, and X is chlorine; $R^1$ is 2,4,6-trimethylphenyl, $R^2$ is 4-methylbenzyl, $R^3$ is H, $R^4$ and $R^5$ are isopropyl, and X is chlorine; $R^1$ is 2,4,6-trimethylphenyl, $R^2$ is 4-methylbenzyl, $R^3$ is H, $R^4$ and $R^5$ are phenyl, and X is chlorine; $R^1$ is 3,5-dimethylphenyl, $R^2$ is phenyl, $R^3$ is H, $R^4$ and $R^5$ are isopropyl, and X is chlorine; $R^1$ is 2,4,6-trimethylphenyl, $R^2$ is 4-methylbenzyl, $R^3$ is H, $R^4$ and $R^5$ are 4-methoxyphenyl, and X is chlorine; $R^1$ is 2,4,6-trimethylphenyl, $R^2$ is 4-methylbenzyl, $R^3$ is H, $R^4$ is t-butyl, $R^5$ is phenyl, and X is chlorine; $R^1$ is 2,4,6-trimethylphenyl, $R^2$ is 4-methylbenzyl, $R^3$ is H, $R^4$ is methyl, $R^5$ is phenyl, and X is chlorine; $R^1$ and $R^2$ are joined to form a prop-1,3-ylene group, $R^3$ is H, $R^4$ and $R^5$ are isopropyl, and X is chlorine; $R^1$ and $R^2$ are joined to form a but-1,4-ylene group, $R^3$ is H, $R^4$ and $R^5$ are isopropyl, and X is chlorine; $R^1$ is 2,4,6-trimethylphenyl, $R^2$ is 4-methylbenzyl, $R^3$ is H, $R^4$ and $R^5$ are joined to form a but-1,4-ylene group, and X is chlorine; $R^1$ is 2,4,6-trimethylphenyl, $R^2$ is 4-methylbenzyl, $R^3$ is H, $R^4$ and $R^5$ are joined to form a 2,2'-dimethylbiphenylene group, and X is chlorine: iii) Structure GUCr1 where $R^1$ is 2-methylphenyl, $R^{2a}$ is 2-methylphenyl, $R^{2b}$ is H, $R^3$ is H, $R^4$ and $R^5$ are isopropyl, and X is chlorine; $R^1$ is 2,6-dimethylphenyl, $R^{2a}$ is phenyl, $R^{2b}$ is H, $R^3$ is H, $R^4$ and $R^5$ are isopropyl, and X is chlorine; $R^1$ is 2,6-dimethylphenyl, $R^{2a}$ is phenyl, $R^{2b}$ is H, $R^3$ is H, $R^4$ and $R^5$ are phenyl, and X is chlorine; $R^1$ is 2,6-dimethylphenyl, $R^{2a}$ and $R^{2b}$ are phenyl, $R^3$ is H, $R^4$ and $R^5$ are isopropyl, and X is chlorine: iv) Structure GUCr4 where $L^{12}$ is prop-1,3-ylene, $L^{23}$ is prop-1,3-ylene, $R^4$ and $R^5$ are isopropyl, and X is chlorine; $L^{12}$ is prop-1,3-ylene, $L^{23}$ is prop-1,3-ylene, $R^4$ and $R^5$ are cyclopentyl, and X is chlorine; $L^{12}$ is prop-1,3-ylene, $L^{23}$ is prop-1,3-ylene, $R^4$ and $R^5$ are cyclohexyl, and X is chlorine; $L^{12}$ is prop-1,3-ylene, $L^{23}$ is prop-1,3-ylene, $R^4$ and $R^5$ are phenyl, and X is chlorine; $L^{12}$ is but-1,3-ylene, $L^{23}$ is prop-1,3-ylene, $R^4$ and $R^5$ are isopropyl, and X is chlorine; $L^{12}$ is but-1,3-ylene, $L^{23}$ is prop-1,3-ylene, $R^4$ and $R^5$ are cyclopentyl, and X is chlorine; $L^{12}$ is but-1,3-ylene, $L^{23}$ is but-1,3-ylene, $R^4$ and $R^5$ are isopropyl, and X is chlorine; $L^{12}$ is but-1,3-ylene, $L^{23}$ is but-1,3-ylene, $R^4$ and $R^5$ are phenyl, and X is chlorine; $L^{12}$ is ethen-1,2-ylene, $L^{23}$ is prop-1,3-ylene, $R^4$ and $R^5$ are isopropyl, and X is chlorine; $L^{12}$ is ethen-1,2-ylene, $L^{23}$ is prop-1,3-ylene, $R^4$ and $R^5$ are cyclopentyl, and X is chlorine; $L^{12}$ is ethen-1,2-ylene, $L^{23}$ is prop-1,3-ylene, $R^4$ and $R^5$ are cyclohexyl, and X is chlorine; $L^{12}$ is phen-1,2-ylene, $L^{23}$ is eth-1,2-ylene, $R^4$ and $R^5$ are isopropyl, and X is chlorine: and v) Structure HCPACr2 where T is sulfur, $L^{12}$ is ethen-1,2-ylene, $R^3$ is H, $R^4$ and $R^5$ are isopropyl, and X is chlorine; and T is sulfur, $L^{12}$ is phen-1,2-ylene, $R^3$ is H, $R^4$ and $R^5$ are isopropyl, and X is chlorine.

In a non-limiting aspect, the heteroatomic ligand can be any one or more of HL 1, HL 2, HL 3, HL 4. HL 5, HL 6, HL 7, HL 7, and HL 9. In some non-limiting aspects, the diphosphino amine chromium compound complex can be a chromium compound complex of any one or more of HLCr 1, HLCr 2, HLCr 3, HLCr 4, HLCr 5, HLCr 6, HLCr 7, HLCr 8, and HLCr 9. In other non-limiting aspects, the diphosphino amine chromium compound complex can be a chromium(III) chloride or chromium(III) acetylacetonate complex of any one or more of HLCr 1, HLCr 2, HLCr 3, HLCr 4, HLCr 5 HLCr 6 HLCr 7 HLCr 8 and HLCr 9.

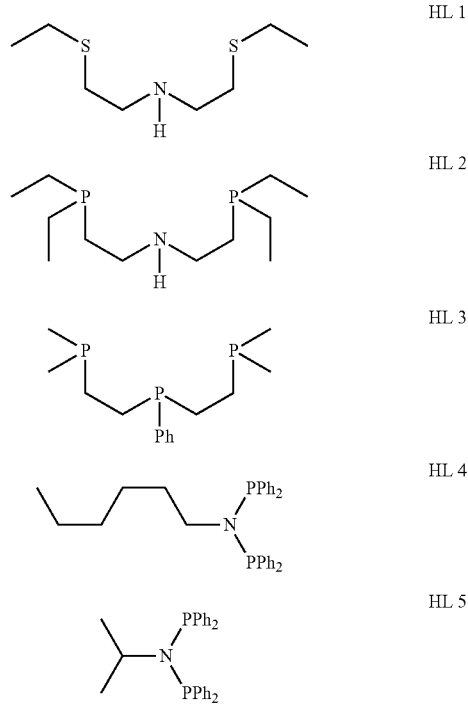

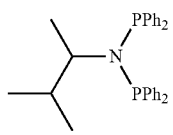

HL 6

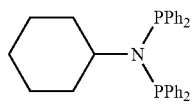

HL 7

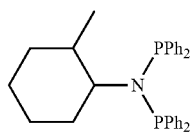

HL 8

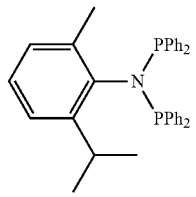

HL 9

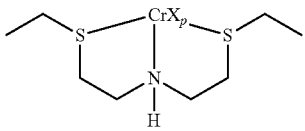

HLCr 1

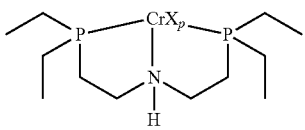

HLCr 2

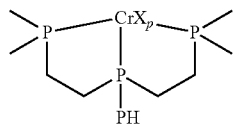

HLCr 3

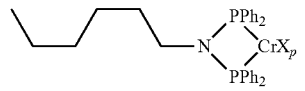

HLCr 4

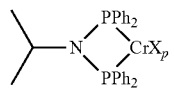

HLCr 5

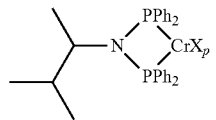

HLCr 6

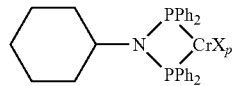

HLCr 7

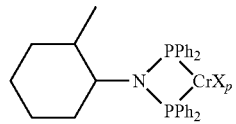

HLCr 8

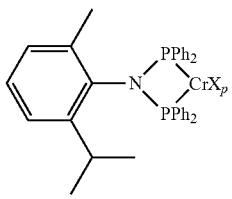

HLCr 9

While not shown in all of the chromium compound names and formulas and/or heteroatomic ligand chromium compound complex formulas and structures provided herein, one of ordinary skill in the art will recognize that a neutral ligand, Q, can be associated with the chromium compounds and/or the heteroatomic ligand chromium compound complexes described/depicted herein which do not explicitly disclose/depict a neutral ligand. Additionally it should be understood that while some of the chromium compounds and/or heteroatomic ligand chromium compound complexes described/depicted/provided herein do not formally show the presence of a neutral ligand, the chromium compounds and/or heteroatomic ligand chromium compound complexes having neural ligands (e.g., nitriles and ethers, among others) are implicitly and fully contemplated as potential the chromium compounds and/or heteroatomic ligand chromium compound complexes that can be utilized in the catalyst system used in aspects of the herein described inventions.

Generally, the neutral ligand of any chromium compound and/or heteroatomic ligand chromium compound complex, when present, independently can be any neutral ligand that forms an isolatable compound with the chromium compound and/or heteroatomic ligand chromium compound complex. In an aspect, each neutral ligand independently can be a nitrile or an ether; alternatively, a nitrile; or alternatively, an ether. The number of neutral ligands, q, can be any number that forms an isolatable compound with the chromium compound and/or heteroatomic ligand chromium compound complex. In an aspect, the number of neutral ligands can be from 0 to 6; alternatively, 0 to 3; alternatively, 0; alternatively, 1; alternatively, 2; alternatively, 3; or alternatively, 4.

Generally, each nitrile ligand independently can be a $C_2$ to $C_{20}$ nitrile; or alternatively, a $C_2$ to $C_{10}$ nitrile. In an aspect, each nitrile ligand independently can be a $C_2$ to $C_{20}$ aliphatic nitrile, a $C_7$ to $C_{20}$ aromatic nitrile, a $C_5$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_5$ to $C_{20}$ aralkane nitrile. In some aspects, each nitrile ligand independently can be a $C_2$ to $C_{10}$ aliphatic nitrile, a $C_7$ to $C_{10}$ aromatic nitrile, a $C_5$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_5$ to $C_{10}$ aralkane nitrile. In an aspect, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand independently can be a $C_2$ to $C_{40}$ ether; alternatively, a $C_2$ to $C_{30}$ ether; or alternatively, a $C_2$ to $C_{20}$ ether. In an aspect, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some aspects, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other aspects, each ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some aspects, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

Generally, the organoaluminum compound utilized in the catalyst systems disclosed herein can be any organoaluminum compound which in conjunction with the heteroatomic ligand chromium compound complex (or the chromium compound and heteroatomic ligand) can catalyze the formation of an oligomer product. In an aspect, the organoaluminum compound can be an aluminoxane, an alkylaluminum compound, or any combination thereof; alternatively, an aluminoxane; or alternatively, an alkylaluminum compound. In an aspect, the alkylaluminum compound can be a trialkylaluminum, an alkylaluminum halide, an alkylaluminum alkoxide, or any combination thereof. In some aspects, the alkylaluminum compound can be a trialkylaluminum, an alkylaluminum halide, or any combination thereof; alternatively, a trialkylaluminum, an alkylaluminum alkoxide, or any combination thereof; or alternatively, a trialkylaluminum. In other aspects, the alkylaluminum compound can be a trialkylaluminum; alternatively, an alkylaluminum halide; or alternatively, an alkylaluminum alkoxide. In an aspect, the aluminoxane utilized in the catalyst systems which are utilized in the processes and systems can be any aluminoxane which in conjunction with the heteroatomic ligand chromium compound complex (or the chromium compound and heteroatomic ligand), can catalyze the formation of an oligomer product. In a non-limiting aspect, the aluminoxane can have a repeating unit characterized by the Formula I:

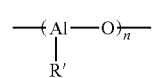

Formula I wherein R' is a linear or branched alkyl group. Alkyl groups of the aluminoxanes and alkylaluminum compounds are independently described herein and can be utilized without limitation to further describe the aluminoxanes having Formula I and/or the alkylaluminum compounds. Generally, n of Formula I can be greater than 1; or alternatively, greater than 2. In an aspect, n can range from 2 to 15; or alternatively, range from 3 to 10.

In an aspect, each halide of any alkylaluminum halide disclosed herein can independently be fluoride, chloride, bromide, or iodide; or alternatively, chloride, bromide, or iodide. In an aspect, each halide of any alkylaluminum halide disclosed herein can be fluoride; alternatively, chloride; alternatively, bromide; or alternatively, iodide.

In an aspect, each alkyl group of an aluminoxane and/or alkylaluminum compound independently can be a $C_1$ to $C_{20}$ alkyl group; alternatively, a $C_1$ to $C_{10}$ alkyl group; or alternatively, a $C_1$ to $C_6$ alkyl group. In an aspect, each alkyl group of an aluminoxane and/or alkylaluminum compound a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some aspects, each alkyl group of an aluminoxane and/or alkylaluminum compound can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each alkoxide group of any alkylaluminum alkoxide disclosed herein independently can be a $C_1$ to $C_{20}$ alkoxy group, a $C_1$ to $C_{10}$ alkoxy group, or a $C_1$ to $C_6$ alkoxy group. In an embodiment, each alkoxide group of any alkylaluminum alkoxide disclosed herein independently can be a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some embodiments, each alkoxide group of any alkylaluminum alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting aspect, useful trialkylaluminum compounds can include trimethylaluminum, triethylaluminum, tripropylaluminum, tributylaluminum, trihexylaluminum, trioctylaluminum, or mixtures thereof. In some non-limiting embodiments, useful trialkylaluminum compounds can include trimethylaluminum, triethylaluminum, tripropylaluminum, tri-n-butylaluminum, tri-isobutylaluminum, tri-hexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, useful trialkylaluminum compounds can include trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, useful alkylaluminum halides can include diethylaluminum chloride, diethylaluminum bromide, ethylaluminum dichloride, ethylaluminum sesquichloride, and mixtures thereof. In some non-limiting embodiments, useful alkylaluminum halides can include diethylaluminum chloride, ethylaluminum dichloride, ethylaluminum sesquichloride, and mixtures thereof. In other non-limiting embodiments, useful alkylaluminum halides can include diethylaluminum chloride; alternatively, diethylaluminum bromide; alternatively, ethylaluminum dichloride; or alternatively, ethylaluminum sesquichloride.

In a non-limiting aspect, the aluminoxane can be, comprise, or consist essentially of, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-entylaluminoxane, 3-pentyl-aluminoxane, iso-pentyl-aluminoxane, neopentylaluminoxane, or mixtures thereof. In some non-limiting aspects, the aluminoxane can be, comprise, or consist essentially of, methylaluminoxane (MAO), modified methylaluminoxane (MMAO), isobutyl aluminoxane, t-butyl aluminoxane, or mixtures thereof. In other non-limiting aspects, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentylaluminoxane.

The components of the catalyst system can be combined in any order, in any manner, and for any length of time (e.g., aging) to prepare the catalyst system. The catalyst system mixture can be aged for any suitable period of time (e.g., 5 sec to 48 hr, from 10 sec to 36 hr, from 30 sec to 24 hr, from 1 min to 18 hr, from 5 min to 6 hr, from 10 min to 4 hr, or from 20 min to 2 hr) in the substantial absence of ethylene prior to introducing the catalyst system mixture into the reaction zone. Herein, the substantial absence of ethylene means that the catalyst system mixture contains less than 1 wt. % ethylene, based on the total weight of the catalyst system mixture. In some instance, less than 0.5 wt. %, less than 0.1 wt. %, or less than 0.05 wt. % ethylene, based upon the total weight of the catalyst system mixture, is present in the catalyst system mixture prior to the reaction zone.

While not limited thereto, the catalyst system can be formed at a temperature in a range from 0° C. to 100° C., from 10° C. to 75° C., from 15° C. to 60° C., or from 20° C. to 40° C. In these and other aspects, these temperature ranges also are meant to encompass circumstances where the catalyst system is formed at a series of different temperatures, instead of at a single fixed temperature, falling within the respective ranges.

The Al to Cr molar ratio of the catalyst system (or in which the oligomer product is formed) can be in a range of 10:1 to 5,000:1, from 50:1 to 3,000:1, from 50:1 to 3,000:1, from 75:1 to 2,000:1, from 100:1 to 2,000:1, of from 100:1 to 1,000:1. If more than one complex and/or more than one organoaluminum are employed, the Al to Cr ratio is based on the total moles of chromium and/or aluminum.

Examples

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

For the ethylene oligomerization reaction system 100 of FIG. 2, a computer simulation was performed to determine the mass flow rate and respective composition of each stream at a particular set of pressure and temperature conditions. A summary of the results is shown in Table A. Note that not every piece of equipment and stream is shown in FIG. 2, and that only certain major components of each stream are summarized in Table A.

The vast majority of the reaction zone effluent stream 125 in FIG. 2 (stream 25 in FIG. 1) is the organic reaction medium (cyclohexane), but based only on the total oligomer product, octene(s) represent approximately 50 mass % and hexene(s) represent approximately 40 mass %. The reaction zone effluent stream 125, which can be heated prior to the first stage separator 130 (e.g., a flash chamber), is separated into 81 mass % of the first liquid stream 132 (which is predominantly cyclohexane and oligomer product) and 19 mass % of the first vapor stream 138 (which is predominantly ethylene). The liquid:vapor split of about 4:25:1 can be varied as needed.

The first liquid stream 132, which can be heated prior the second stage separator 140, is separated into 90 mass % of the second liquid stream 142 (which is predominantly cyclohexane and oligomer product) and 10 mass % of the second vapor stream 148 (which is predominantly ethylene and cyclohexane). The liquid:vapor split of about 9:1 can be varied as needed.

The second vapor stream 148, which can be cooled prior to the knock out pot 150, is separated into the first oligomer fraction 155 (which is predominantly cyclohexane and oligomer product) and vapor stream 158 (which is predominantly ethylene). Vapor stream 158 enters first stage compressor 170 and the light fraction 173 exiting compressor 170 is combined with the first vapor stream 138 to form combined light stream 178, which then can be cooled. Combined light stream 178 has a higher ethylene percentage than that of first vapor stream 138 due to the addition of the ethylene-rich light fraction 173.

Combined light stream 178 enters knock out pot 180. Exiting the knock out pot 180 are liquid stream 183 (which has a significant cyclohexane and oligomer product content, and is fed to the liquid oligomer separations system 160), the lower pressure ethylene stream 188 (which contains approximately 91 mass % ethylene and less than 0.25 mass % butene(s)), and the light gas purge stream 185 (which can have approximately the same composition as ethylene stream 188).

The liquid oligomer separations system 160 in FIG. 2 does not show all incoming and outgoing streams. As would be readily recognized, a $C_{10+}$ oligomer stream exiting the separations system 160 is not shown. Further, the separations system 160 can include more than one separating device to isolate and purify desired hexene and octene products. For instance, the separations system 160 can include two distillation columns. Thus, in Table A, certain precursor stream compositions are shown prior to the final streams in FIG. 2. In separations system 160, a precursor stream (pre-167) contains predominantly octene(s), but also has significant amounts of $C_{10+}$ oligomers and cyclohexane, but after further separations, the fourth stream 167 in FIG. 2 (stream 67 in FIG. 1) containing over 97 mass % octene(s) exits the separations system 160. For the catalyst systems disclosed herein, the amount of 1-octene in the octene(s) stream is independently described herein and can be utilized, without limitation, to describe the amount of 1-octene in the octene(s) stream (based on total octene(s) in the fourth stream).

Likewise, a precursor stream (pre-165) is predominantly cyclohexane, but is otherwise rich in hexene(s), and after further separations, the third stream 165 in FIG. 2 (stream 65 in FIG. 1) containing over 99 mass % hexene(s) exits the separations system 160. For the catalyst systems disclosed herein, the amount of 1-hexene in the hexene(s) stream is independently described herein and can be utilized, without limitation, to describe the amount of 1-hexene in the hexene(s) stream (based on total hexene(s) in the third stream).

Another precursor stream (pre-163) contains significant amounts of ethylene, desirable hexene(s), and undesirable butene(s). After further separations to recover the desirable hexene(s), the second stream 163 (heavy gas purge stream) in FIG. 2 (stream 63 in FIG. 1) containing 8-9 mass % butene(s) and less than 5 mass % $C_{6+}$ oligomers exits the separations system 160.

The overhead light stream 161, which is predominantly ethylene, also exits the liquid oligomer separations system 160. Optionally, and not shown in FIG. 2, some of the ethylene can be further concentrated from the light stream 161 (to over 90 mass % ethylene), and this ethylene-rich stream can be combined with lower pressure ethylene stream 188 at second stage compressor 190 to form the first stream 195 in FIG. 2 (stream 95 in FIG. 1), which is recycled to the reaction zone 120. The first stream 195 (ethylene recycle stream) contains approximately 91 mass % ethylene, less than 1 mass % $C_{4+}$ olefins, and less than 0.25 mass % butene(s) (mass ratio of ethylene:butene(s) is 380:1). The first stream 195 also contains only minor amounts of hydrogen (0.01 mass %) and methane (1.5 mass %). Since very little butene(s) are recycled, the amount of butene(s) in the reaction zone 120 is reduced significantly: the reaction zone effluent stream 125 surprisingly contains only 0.16 mass % butene(s). Also advantageously, the second stream 163 contains, on a mass basis, over three times as much butene(s) as that in the first stream 195.

Recycled ethylene from first stream 195 is combined with feed streams 115 in the oligomerization reaction zone 115. The feed streams can include, for instance, a catalyst system feed stream, an organic reaction medium feed stream, an ethylene feed stream, and a hydrogen feed stream (if hydrogen is used). The (fresh) ethylene feed stream, in some instances, can be combined with first stream 195 (ethylene recycle stream) and fed into the reaction zone separately from the other feed streams (e.g., the catalyst system feed stream).

From Table A and FIG. 2, the following additional results are apparent. The overall ethylene recycle rate is an unexpectedly high 91-92 mass %, and this is determined by dividing the amount of ethylene in the first stream 195 by the amount of ethylene in the effluent stream 125. This high level of recycle is very important because ethylene conversion in the reaction zone 120 is approximately 60 mass %, which is determined based on the total amount of ethylene entering the reaction zone (approximately 116,400 lb/hr, not shown in Table A) and the amount of unreacted ethylene in the reaction zone effluent stream 125.

On a mass % basis, the light gas purge stream 185 contains more hydrogen and more methane than that in the first stream 195. The light gas purge steam 185 contains 0.015 mass % hydrogen and 1.67 mass % methane. Further, the mass ratio of the light gas purge stream 185 to the second stream 163 (heavy gas purge stream)—ratio of light:heavy purge—is approximately 1:9.

The methods disclosed herein, as illustrated in Table A and FIGS. 1-2, demonstrate that the amount of ethylene being recycled to an oligomerization reaction zone can be increased significantly while concurrently significantly reducing the amount of butene(s) that are recycled to the oligomerization reaction zone.

TABLE A

| | Stream | | | | | | | | | |
|---|---|---|---|---|---|---|---|---|---|---|
| | 125 | 138 | 132 | 142 | 148 | 158 | 155 | 161 | 173 | 178 |
| Flow Rate (lb/hr) | 311287 | 58551 | 252736 | 227480 | 25256 | 9998 | 15258 | 10149 | 9998 | 68549 |
| Temperature (F.) | 195 | 240 | 240 | 240 | 240 | 100 | 100 | 100 | 251 | 60 |
| Pressure (psia) | 915 | 320 | 320 | 115 | 115 | 110 | 110 | 90 | 329 | 315 |
| Composition of Stream (mass %) | | | | | | | | | | |
| Hydrogen | 0.00% | 0.01% | 0.00% | 0.00% | 0.00% | 0.00% | 0.00% | 0.00% | 0.00% | 0.01% |
| Methane | 0.24% | 1.12% | 0.03% | 0.00% | 0.31% | 0.77% | 0.01% | 0.29% | 0.77% | 1.07% |
| Ethylene | 14.96% | 59.91% | 4.55% | 1.20% | 34.71% | 82.37% | 3.48% | 73.91% | 82.37% | 63.18% |
| Butene(s) | 0.16% | 0.31% | 0.13% | 0.09% | 0.44% | 0.58% | 0.34% | 3.34% | 0.58% | 0.35% |
| Hexene(s) | 8.44% | 5.54% | 9.11% | 9.05% | 9.64% | 2.68% | 14.20% | 5.92% | 2.68% | 5.12% |
| Octene(s) | 10.63% | 1.99% | 12.63% | 13.65% | 3.42% | 0.12% | 5.59% | 0.00% | 0.12% | 1.72% |
| C10+ | 1.94% | 0.05% | 2.37% | 2.63% | 0.07% | 0.00% | 0.12% | 0.00% | 0.00% | 0.04% |
| Cyclohexane | 59.96% | 26.17% | 67.79% | 70.16% | 46.44% | 7.20% | 72.15% | 6.60% | 7.20% | 23.40% |

TABLE A-continued

| | Stream | | | | | | | | | |
|---|---|---|---|---|---|---|---|---|---|---|
| | 183 | 188 | 195 | pre-165 | pre-163 | 163 | pre-167 | 185 | 165 | 167 |
| Flow Rate (lb/hr) | 25775 | 42273 | 46945 | 218901 | 7615 | 4694 | 42997 | 500 | 25772 | 33278 |
| Temperature (F.) | 60 | 60 | 218 | 304 | 105 | 20 | 400 | 60 | 100 | 100 |
| Pressure (psia) | 315 | 315 | 929 | 95 | 40 | 35 | 99 | 315 | 38 | 20 |
| | Composition of Stream (mass %) | | | | | | | | | |
| Hydrogen | 0.00% | 0.01% | 0.013% | 0.00% | 0.00% | 0.00% | 0.00% | 0.015% | 0.00% | 0.00% |
| Methane | 0.07% | 1.67% | 1.56% | 0.00% | 0.06% | 0.10% | 0.00% | 1.67% | 0.00% | 0.00% |
| Ethylene | 17.04% | 90.99% | 91.10% | 0.07% | 44.78% | 71.45% | 0.00% | 90.99% | 0.00% | 0.00% |
| Butene(s) | 0.58% | 0.21% | 0.24% | 0.03% | 8.20% | 8.27% | 0.00% | 0.21% | 0.01% | 0.00% |
| Hexene(s) | 12.73% | 0.54% | 0.50% | 11.62% | 33.08% | 4.53% | 0.01% | 0.54% | 99.10% | 0.00% |
| Octene(s) | 4.54% | 0.02% | 0.02% | 0.25% | 0.00% | 0.00% | 76.41% | 0.02% | 0.00% | 97.65% |
| C10+ | 0.11% | 0.00% | 0.00% | 0.00% | 0.00% | 0.00% | 14.02% | 0.00% | 0.00% | 0.01% |
| Cyclohexane | 60.09% | 1.29% | 1.16% | 84.70% | 0.04% | 0.00% | 7.44% | 1.29% | 0.30% | 0.05% |

The invention is described above with reference to numerous aspects and specific examples. Many variations will suggest themselves to those skilled in the art in light of the above detailed description. All such obvious variations are within the full intended scope of the appended claims. Other statements of the invention can include, but are not limited to, the following (statements are described as "comprising" but, alternatively, can "consist essentially of" or "consist of"):

Statement 1. A method for recycling ethylene from a reaction zone effluent stream from an oligomerization reaction zone, the reaction zone effluent stream containing an oligomer product effluent comprising at least 20 mass % octene(s), the method comprising:

a) separating the reaction zone effluent stream into i) a first stream comprising ethylene and less than or equal to 5 mass % $C_{4+}$ olefins, ii) a second stream comprising butene(s) and less than or equal to 10 mass % $C_{6+}$ olefins, iii) a third stream comprising any amount of hexene(s) disclosed herein, e.g., at least 96, 97, 98, or 99 mass % hexene(s), and iv) a fourth stream comprising any amount of octene(s) disclosed herein, e.g., at least 96, 97, 98, or 99 mass % octene(s); and b) recycling the first stream into the oligomerization reaction zone.

Statement 2. The method defined in statement 1, wherein the oligomer product effluent comprises any amount of octene(s) disclosed herein, e.g., at least 20, 30 or 40 mass %; a maximum of 99, 95, 92.5, 90, 87.5, or 85 mass %; or from 20 to 99 mass %, from 30 to 95 mass %, from 40 to 95 mass %, from 40 to 90 mass %, from 20 to 90 mass %, from 30 to 87.5 mass %, from 30 to 85 mass %, from 40 to 87.5 mass %, from 40 to 85 mass %, from 20 to 60 mass %, from 30 to 55 mass %, or from 40 to 55 mass % octene(s), based on the total amount of oligomers in the oligomer product effluent.

Statement 3. The method defined in statement 1 or 2, wherein the fourth stream comprises any amount of 1-octene disclosed herein, e.g., at least 95, 96, 96.5, 97, 97.5, 98, or 98.5 mass % 1-octene (among other amounts disclosed herein), based on the total mass of the octene(s).

Statement 4. The method defined in any one of the preceding statements, wherein the third stream comprises any amount of 1-hexene disclosed herein, e.g., at least 90, 92.5, 95, 97.5, 98, 98.5, or 99 mass % 1-hexene (among other amounts disclosed herein), based on the total mass of the hexene(s).

Statement 5. The method defined in any one of the preceding statements, wherein the second stream comprises any amount of $C_6$, olefins disclosed herein, e.g., less than or equal to 8, 7, 6, 5, 4, or 3 mass % $C_6$, olefins.

Statement 6. The method defined in any one of the preceding statements, wherein the second stream contains more butene(s) than, or at least twice as much butene(s) as, or at least three times as much butene(s) as, that in the first stream, on a mass basis.

Statement 7. The method defined in any one of the preceding statements, wherein the first stream comprises any amount of $C_{4+}$ olefins disclosed herein, e.g., less than or equal to 4, 3, 2, or 1 mass % $C_{4+}$ olefins.

Statement 8. The method defined in any one of the preceding statements, wherein the first stream comprises any amount of butene(s) disclosed herein, e.g., less than or equal to 2, 1.5, 1, 0.75, 0.5, 0.35, or 0.2 mass % butene(s) (among other amounts disclosed herein).

Statement 9. The method defined in any one of the preceding statements, wherein the first stream comprises any amount of ethylene disclosed herein, e.g., at least 85, 86, 87, 88, or 90 mass % ethylene (among other amounts disclosed herein).

Statement 10. The method defined in any one of the preceding statements, wherein the first stream further comprises any amount of hydrogen and/or methane disclosed herein, e.g., less than or equal to 5, 4, 3, 2, or 1 mass % hydrogen and/or methane.

Statement 11. The method defined in any one of the preceding statements, wherein the first stream is characterized by any mass ratio of ethylene:butene(s) disclosed herein, e.g., at least 100:1, 150:1, 200:1, 300:1, or 350:1 (among other amounts disclosed herein).

Statement 12. The method defined in any one of the preceding statements, wherein any amount of ethylene in the reaction zone effluent stream disclosed herein is recycled to the oligomerization reaction zone, e.g., at least 86, 88, 89, 90, or 91 mass %; a maximum of 99, 97, 96, 95, or 94 mass %; or from 86 to 99 mass %, from 88 to 97 mass %, from 89 to 96 mass %, from 90 to 95 mass %, or from 91 to 94 mass % (among other amounts disclosed herein).

Statement 13. The method defined in any one of the preceding statements, wherein the oligomer product effluent further comprises any amount of hexene(s) disclosed herein, e.g., at least 15, 20, 25, 30, or 35 mass %; a maximum of 75, 65, 60, 55, or 50 mass %; or from 20 to 60 mass from 25 to 55 mass %, or from 30 to 50 mass % hexene(s) (among other amounts disclosed herein).

Statement 14. The method defined in any one of the preceding statements, wherein separating the reaction zone effluent stream into the first stream comprises at least two separating stages.

Statement 15. The method defined in any one of the preceding statements, wherein separating the reaction zone effluent stream into the first stream comprises at least two compressing stages.

Statement 16. The method defined in any one of the preceding statements, wherein separating the reaction zone effluent stream into the first stream comprises:

(a) separating the reaction zone effluent stream into a first vapor stream and a first liquid stream;

(b) separating the first liquid stream into a second vapor stream and a second liquid stream;

(c) separating the second vapor stream into a light fraction and a first oligomer fraction; and (d) combining the first vapor stream with the light fraction and forming the first stream and a light gas purge stream.

Statement 17. The method defined in statement 16, wherein the light gas purge stream contains more hydrogen than that in the first stream, on a mass % basis.

Statement 18. The method defined in statement 16 or 17, wherein the light gas purge stream contains more methane than that in the first stream, on a mass % basis.

Statement 19. The method defined in any one of statements 16-18, wherein the light gas purge stream comprises an amount of hydrogen and/or methane in any range disclosed herein, e.g., less than or equal to 5, 4, 3, 2, or 1 mass % hydrogen and/or methane, based on the total mass of the light gas purge stream (among other amounts disclosed herein).

Statement 20. The method defined in any one of statements 16-19, further comprising separating the second liquid stream into an overhead stream, the second stream, the third stream, and the fourth stream.

Statement 21. The method defined in any one of the preceding statements, wherein the oligomerization reaction zone has any ethylene conversion disclosed herein, e.g., at least 20, 30, 35, 40, 45, or 50 mass %; a maximum of 99, 95, 90, 80, 75, 70, or 65 mass %; or from 20 to 100 mass %, from 30 to 90 mass %, from 40 to 80 mass %, from 50 to 70 mass %, or from 55 to 65 mass % conversion (among other conversions disclosed herein), based on the amount of ethylene entering the reaction zone and the amount of ethylene in the reaction zone effluent stream.

Statement 22. The method defined in any one of the preceding statements, wherein the oligomerization reaction zone has any amount of butene(s) disclosed herein, e.g., at least 0.01, 0.02, 0.035, 0.05, or 0.1 mass %; a maximum of 1, 0.75, 0.5, 0.35, 0.25, or 0.2 mass %; or from 0.02 to 0.5 mass %, from 0.05 to 0.35 mass %, or from 0.1 to 0.2 mass % butene(s) (among other amounts disclosed herein).

Statement 23. The method defined in any one of the preceding statements, wherein the second stream comprises an amount of butene(s) in any range disclosed herein, e.g., at least 1, 2, 3, 4, or 5 mass %; a maximum of 25, 20, 18, 15 or 12 mass %; or from 3 to 25 mass %, from 4 to 15 mass %, or from 5 to 12 mass % butene(s) (among other amounts disclosed herein), based on the total mass of the second stream.

Statement 24. The method defined in any one of statements 16-23, wherein the mass ratio of the light gas purge stream to the second stream is in any range disclosed herein, e.g., from 1:5 to 1:20, from 1:6 to 1:15, or from 1:7 to 1:12.

Statement 25. The method defined in any one of the preceding statements, where the amount of 1-butene in any stream containing butene(s) is any amount disclosed herein, e.g., at least 80, 85, 90, 95, or 98 mass % 1-butene, based on the total mass of the butene(s).

Statement 26. The method defined in any one of the preceding statements, further comprising the steps of:

introducing (1) ethylene, (2) a catalyst system or catalyst system components, (3) optionally, an organic reaction medium, and (4) optionally, hydrogen, into the oligomerization reaction zone;

forming the oligomer product effluent; and discharging the oligomerization reaction zone effluent stream from the oligomerization reaction zone.

Statement 27. The method defined in statement 26, wherein the catalyst system or catalyst system components comprise (i) a heteroatomic ligand transition metal compound complex and an organoaluminum compound, or (ii) a heteroatomic ligand, a transition metal compound, and an organoaluminum compound.

Statement 28. The method defined in any one of the preceding statements, wherein the method is performed continuously.

I claim:

1. A method for recycling ethylene from a reaction zone effluent stream from an oligomerization reaction zone, the reaction zone effluent stream containing an oligomer product effluent comprising at least 20 mass % octene(s), the method comprising:

a) separating the reaction zone effluent stream into
  i) a first stream comprising ethylene and less than or equal to 5 mass % $C_{4+}$ olefins,
  ii) a second stream comprising butene(s) and less than or equal to 10 mass % $C_{6+}$ olefins,
  iii) a third stream comprising at least 96 mass % hexene(s), and
  iv) a fourth stream comprising at least 96 mass % octene(s); and b) recycling the first stream into the oligomerization reaction zone.

2. The method of claim 1, wherein at least 88 mass % ethylene is recycled to the oligomerization reaction zone.

3. The method of claim 1, wherein the first stream comprises:
  less than or equal to 3 mass % $C_{4+}$ olefins;
  less than or equal to 1 mass % butene(s); and
  at least 88 mass % ethylene.

4. The method of claim 1, wherein the first stream is characterized by a mass ratio of ethylene:butene(s) of at least 200:1.

5. The method of claim 1, wherein separating the reaction zone effluent stream into the first stream comprises at least two separating stages.

6. The method of claim 5, wherein separating the reaction zone effluent stream into the first stream comprises at least two compressing stages.

7. The method of claim 1, wherein the oligomerization reaction zone has an ethylene conversion in a range from 30 to 90 mass %.

8. The method of claim 1, wherein the oligomerization reaction zone contains less than or equal to 0.5 mass % butene(s).

9. The method of claim 1, wherein:
  the third stream comprises at least 98 mass % hexene(s); and
  the fourth stream comprises at least 97 mass % octene(s).

10. The method of claim 9, wherein the fourth stream comprises at least 97 mass % 1-octene, based on the total mass of the octene(s).

11. The method of claim 1, wherein the oligomer product effluent comprises at least 30 mass % octene(s) and at least 30 mass % hexene(s), based on the total amount of oligomers in the oligomer product effluent.

12. The method of claim 1, wherein:
the second stream comprises from 3 to 25 mass % butene(s) and less than or equal to 7 mass % $C_{6+}$ olefins; and
the second stream contains at least twice as much butene(s) as that in the first stream, on a mass basis.

13. The method of claim 1, wherein separating the reaction zone effluent stream into the first stream comprises:
(a) separating the reaction zone effluent stream into a first vapor stream and a first liquid stream;
(b) separating the first liquid stream into a second vapor stream and a second liquid stream;
(c) separating the second vapor stream into a light fraction and a first oligomer fraction; and
(d) combining the first vapor stream with the light fraction and forming the first stream and a light gas purge stream.

14. The method of claim 13, further comprising separating the second liquid stream into an overhead stream, the second stream, the third stream, and the fourth stream.

15. The method of claim 14, wherein a mass ratio of the light gas purge stream to the second stream is in a range from 1:5 to 1:20.

16. A process comprising:
A) introducing ethylene, a catalyst system or catalyst system components, optionally, an organic reaction medium, and optionally, hydrogen, into an oligomerization reaction zone;
B) forming an oligomer product effluent in the oligomerization reaction zone, the oligomer product effluent comprising at least 20 mass % octene(s);
C) discharging a reaction zone effluent stream from the oligomerization reaction zone, the reaction zone effluent stream containing the oligomer product effluent stream;
D) separating the reaction zone effluent stream into
i) a first stream comprising ethylene and less than or equal to 5 mass % $C_{4+}$ olefins,
ii) a second stream comprising butene(s) and less than or equal to 10 mass % $C_{6+}$ olefins,
iii) a third stream comprising at least 96 mass % hexene(s), and
iv) a fourth stream comprising at least 96 mass % octene(s); and
E) recycling the first stream into the oligomerization reaction zone.

17. The process of claim 16, wherein the catalyst system or catalyst system components comprise (i) a heteroatomic ligand transition metal compound complex and an organoaluminum compound, or (ii) a heteroatomic ligand, a transition metal compound, and an organoaluminum compound.

18. The process of claim 16, wherein the first stream comprises:
less than or equal to 4 mass % $C_{4+}$ olefins;
less than or equal to 0.75 mass % butene(s); and
at least 87 mass % ethylene.

19. The process of claim 18, wherein the first stream is further characterized by a mass ratio of ethylene:butene(s) of at least 150:1.

20. The process of claim 19, wherein the oligomerization reaction zone contains less than or equal to 0.35 mass % butene(s).

* * * * *